United States Patent
Alexander et al.

(10) Patent No.: US 10,557,851 B2
(45) Date of Patent: Feb. 11, 2020

(54) SIGNALING CONJUGATES AND METHODS OF USE

(71) Applicant: VENTANA MEDICAL SYSTEMS, INC., Tucson, AZ (US)

(72) Inventors: Nelson Alexander, Marana, AZ (US); William Day, Tucson, AZ (US); Jerome W. Kosmeder, II, Tucson, AZ (US); Mark Lefever, Oro Valley, AZ (US); Larry Morrison, Oro Valley, AZ (US); Anne M. Pedata, Tucson, AZ (US); Stacey Stanislaw, Tucson, AZ (US)

(73) Assignee: Ventana Medical Systems, Inc., Tuscon, AZ (US)

( * ) Notice: Subject to any disclaimer, the term of this patent is extended or adjusted under 35 U.S.C. 154(b) by 0 days.

(21) Appl. No.: 16/038,389

(22) Filed: Jul. 18, 2018

(65) Prior Publication Data

US 2018/0328932 A1    Nov. 15, 2018

Related U.S. Application Data

(62) Division of application No. 13/849,160, filed on Mar. 22, 2013, now Pat. No. 10,041,950.
(Continued)

(51) Int. Cl.
*C12Q 1/68* (2018.01)
*G01N 33/58* (2006.01)
(Continued)

(52) U.S. Cl.
CPC .............. *G01N 33/581* (2013.01); *C12Q 1/68* (2013.01); *C12Q 1/682* (2013.01); *G01N 33/53* (2013.01); *G01N 33/542* (2013.01)

(58) Field of Classification Search
USPC .......... 435/6.1, 6.11, 7.1, 91.1; 436/94, 501; 536/23.1, 24.3; 530/300, 350
See application file for complete search history.

(56) References Cited

U.S. PATENT DOCUMENTS

| 5,196,306 A | 3/1993 | Bobrow et al. |
| 5,268,486 A | 12/1993 | Waggoner et al. |

(Continued)

FOREIGN PATENT DOCUMENTS

| EP | 0747700 | 12/1996 |
| EP | 0436597 | 4/1997 |

(Continued)

OTHER PUBLICATIONS

Adamczyk, Maciej; Buko, Alex; Chen, Yon-Yih; Fishpaugh, Jeffrey R; Gebler, John C; Johnson, Donald D. Characterization of protein-hapten conjugates. 1. Matrix-assisted laser desorption ionization mass spectrometry of immuno BSA-hapten conjugates and comparison with other characterization methods. Bioconjugate chemistry 1994; 5(6): 631-635.

(Continued)

*Primary Examiner* — Frank W Lu
(74) *Attorney, Agent, or Firm* — Robin L. Teskin; Baker, Donelson, Bearman, Caldwell & Berkowitz PC

(57) ABSTRACT

Disclosed herein are embodiments of a signaling conjugate, embodiments of a method of using the signaling conjugates, and embodiments of a kit comprising the signaling conjugate. The disclosed signaling conjugate comprises a latent reactive moiety and a chromogenic moiety that may further comprise a linker suitable for coupling the latent reactive moiety to the chromogenic moiety. The signaling conjugate may be used to detect one or more targets in a biological sample and are capable of being covalently deposited directly on or proximally to the target. Particular disclosed (Continued)

embodiments of the method of using the signaling conjugate comprise multiplexing methods.

19 Claims, 27 Drawing Sheets
(23 of 27 Drawing Sheet(s) Filed in Color)

Related U.S. Application Data

(60) Provisional application No. 61/778,093, filed on Mar. 12, 2013, provisional application No. 61/710,607, filed on Oct. 5, 2012, provisional application No. 61/616,330, filed on Mar. 27, 2012.

(51) Int. Cl.
  *C12Q 1/682* (2018.01)
  *G01N 33/53* (2006.01)
  *G01N 33/542* (2006.01)

(56) References Cited

U.S. PATENT DOCUMENTS

| | | |
|---|---|---|
| 5,486,616 A | 1/1996 | Waggoner et al. |
| 5,569,587 A | 10/1996 | Waggoner |
| 5,583,001 A | 12/1996 | Bobrow et al. |
| 5,585,089 A | 12/1996 | Queen et al. |
| 5,688,966 A | 11/1997 | Bobrow et al. |
| 5,731,158 A | 3/1998 | Bobrow et al. |
| 5,759,808 A | 6/1998 | Casterman et al. |
| 5,767,287 A | 6/1998 | Bobrow et al. |
| 5,800,988 A | 9/1998 | Casterman et al. |
| 5,839,091 A | 11/1998 | Rhett et al. |
| 5,840,526 A | 11/1998 | Casterman et al. |
| 5,863,748 A | 1/1999 | Bobrow |
| 5,874,541 A | 2/1999 | Casterman et al. |
| 5,902,727 A | 5/1999 | Roth et al. |
| 5,948,359 A | 9/1999 | Kalra et al. |
| 6,005,079 A | 12/1999 | Casterman et al. |
| 6,015,695 A | 1/2000 | Casterman et al. |
| 6,183,693 B1 | 2/2001 | Bogen et al. |
| 6,352,861 B1 | 3/2002 | Copeland et al. |
| 6,372,937 B1 | 4/2002 | Bobrow et al. |
| 6,593,100 B2 | 7/2003 | Bobrow et al. |
| 6,686,145 B1 | 2/2004 | Waggoner et al. |
| 6,696,246 B1 | 2/2004 | Huan et al. |
| 6,972,326 B2 | 12/2005 | Haugland et al. |
| 6,974,873 B2 | 12/2005 | Leung et al. |
| 6,977,305 B2 | 12/2005 | Leung et al. |
| 7,183,072 B1 | 2/2007 | Hainfeld |
| 7,252,955 B2 | 8/2007 | Pant et al. |
| 7,291,457 B2 | 11/2007 | Miller et al. |
| 7,465,810 B2 | 12/2008 | Diwu et al. |
| 7,566,790 B2 | 7/2009 | Leung et al. |
| 7,671,214 B2 | 3/2010 | Leung et al. |
| 7,695,929 B2 | 4/2010 | Kosmeder et al. |
| 7,741,045 B2 | 6/2010 | Gerdes et al. |
| 7,741,046 B2 | 6/2010 | Larsen et al. |
| 7,754,893 B2 | 7/2010 | Diwu et al. |
| 7,790,893 B2 | 9/2010 | Leung et al. |
| 7,820,783 B2 | 10/2010 | Diwu et al. |
| 7,820,824 B2 | 10/2010 | Leung et al. |
| 7,842,823 B2 | 11/2010 | Chang |
| 7,888,060 B2 | 2/2011 | Hainfeld et al. |
| 7,892,781 B2 | 2/2011 | Powell et al. |
| 7,927,830 B2 | 4/2011 | Leung et al. |
| 7,951,554 B2 | 5/2011 | Hainfeld et al. |
| 7,972,789 B2 | 7/2011 | Petersen |
| 7,985,552 B2 | 7/2011 | Diwu et al. |
| 8,021,850 B2 | 9/2011 | Guo |
| 8,034,927 B2 | 10/2011 | Diwu et al. |
| 8,036,833 B2 | 10/2011 | Rimm et al. |
| 8,071,288 B2 | 12/2011 | Gold et al. |
| 8,093,012 B2 | 1/2012 | Hamann et al. |
| 8,093,404 B2 | 1/2012 | Diwu et al. |
| 8,105,829 B2 | 1/2012 | Diwu et al. |
| 8,114,636 B2 | 2/2012 | Agnew et al. |
| 8,252,932 B2 | 8/2012 | Leung et al. |
| 8,257,926 B2 | 9/2012 | Diwu et al. |
| 8,258,292 B2 | 9/2012 | Diwu et al. |
| 8,290,236 B2 | 10/2012 | Lett et al. |
| 8,304,195 B2 | 11/2012 | Archer et al. |
| 8,304,560 B2 | 11/2012 | Diwu et al. |
| 8,309,059 B2 | 11/2012 | Corona et al. |
| 8,323,903 B2 | 12/2012 | Archer et al. |
| 8,435,735 B2 | 5/2013 | Lohse |
| 8,535,894 B2 | 9/2013 | Archer et al. |
| 8,569,506 B2 | 10/2013 | Leung et al. |
| 8,586,743 B2 | 11/2013 | Antoulinakis et al. |
| 8,614,302 B2 | 12/2013 | Leung et al. |
| 8,623,324 B2 | 1/2014 | Diwu et al. |
| 8,658,361 B2 | 2/2014 | Wu et al. |
| 8,791,258 B2 | 7/2014 | Chang |
| 8,871,442 B2 | 10/2014 | May et al. |
| 8,921,543 B2 | 12/2014 | Diwu et al. |
| 8,993,295 B2 | 3/2015 | Seed et al. |
| 9,091,691 B2 | 7/2015 | Loshe |
| 9,377,465 B2 | 6/2016 | Lohse et al. |
| 9,671,400 B2 | 6/2017 | Lohse |
| 10,041,950 B2 | 8/2018 | Alexander et al. |
| 2001/0039035 A1 | 11/2001 | Bobrow et al. |
| 2002/0064794 A1 | 5/2002 | Leung et al. |
| 2002/0077487 A1 | 6/2002 | Leung et al. |
| 2003/0073149 A1 | 4/2003 | Archer et al. |
| 2004/0018492 A1 | 1/2004 | Miller et al. |
| 2004/0110234 A1 | 6/2004 | Pant et al. |
| 2005/0069962 A1 | 3/2005 | Archer et al. |
| 2005/0186641 A1 | 8/2005 | Haugland et al. |
| 2005/0255475 A1 | 11/2005 | Kumar et al. |
| 2006/0004188 A1 | 1/2006 | Leung et al. |
| 2006/0099638 A1 | 5/2006 | Leung et al. |
| 2006/0121503 A1 | 6/2006 | Diwu et al. |
| 2007/0141658 A1 | 6/2007 | Chang |
| 2007/0154958 A1 | 7/2007 | Hamann et al. |
| 2007/0178511 A1 | 8/2007 | Leung et al. |
| 2007/0178512 A1 | 8/2007 | Leung et al. |
| 2007/0232805 A1 | 10/2007 | Leung et al. |
| 2007/0249014 A1 | 10/2007 | Agnew et al. |
| 2007/0269902 A1 | 11/2007 | Beechem et al. |
| 2008/0013816 A1 | 1/2008 | Rimm et al. |
| 2008/0050731 A1 | 2/2008 | Agnew et al. |
| 2008/0118934 A1 | 5/2008 | Gerdes et al. |
| 2008/0118944 A1 | 5/2008 | Larsen et al. |
| 2008/0160535 A1 | 7/2008 | Gold et al. |
| 2008/0182284 A1 | 7/2008 | Haugland et al. |
| 2008/0213783 A1 | 9/2008 | Hainfeld et al. |
| 2008/0268462 A1 | 10/2008 | Kosmeder et al. |
| 2008/0318249 A1 | 12/2008 | Powell et al. |
| 2009/0004753 A1 | 1/2009 | Antoulinakis et al. |
| 2009/0035809 A1 | 2/2009 | Leung et al. |
| 2009/0035810 A1 | 2/2009 | Leung et al. |
| 2009/0124511 A1 | 5/2009 | Archer et al. |
| 2009/0136935 A1 | 5/2009 | Petersen |
| 2009/0156799 A1 | 6/2009 | Diwu et al. |
| 2009/0215148 A1 | 8/2009 | Diwu et al. |
| 2009/0215643 A1 | 8/2009 | Aurich-Costa et al. |
| 2009/0246788 A1 | 10/2009 | Albert et al. |
| 2009/0258418 A1 | 10/2009 | Diwu et al. |
| 2010/0009394 A1 | 1/2010 | Guo |
| 2010/0022768 A1 | 1/2010 | Diwu et al. |
| 2010/0029954 A1 | 2/2010 | Diwu et al. |
| 2010/0055761 A1 | 3/2010 | Seed et al. |
| 2010/0075862 A1 | 3/2010 | Duffy et al. |
| 2010/0159446 A1 | 6/2010 | Haff et al. |
| 2010/0221727 A1 | 9/2010 | Hainfeld et al. |
| 2010/0240047 A1 | 9/2010 | Lohse |
| 2010/0240085 A1 | 9/2010 | Lohse |
| 2010/0248231 A1 | 9/2010 | Wei et al. |
| 2010/0261181 A1 | 10/2010 | Agnew et al. |
| 2010/0285467 A1 | 11/2010 | Lohse et al. |
| 2010/0317542 A1 | 12/2010 | Lim et al. |
| 2011/0045585 A1 | 2/2011 | Diwu et al. |
| 2011/0053162 A1 | 3/2011 | Corona et al. |

(56) References Cited

U.S. PATENT DOCUMENTS

| | | | |
|---|---|---|---|
| 2011/0070593 A1 | 3/2011 | Diwu et al. |
| 2011/0130306 A1 | 6/2011 | Chang |
| 2011/0171678 A1 | 7/2011 | Leung et al. |
| 2011/0230664 A1 | 9/2011 | Petersen |
| 2011/0235880 A1 | 9/2011 | Lett et al. |
| 2012/0045759 A1 | 2/2012 | Diwu et al. |
| 2012/0053332 A1 | 3/2012 | Diwu et al. |
| 2012/0070862 A1 | 3/2012 | Alexander et al. |
| 2012/0100540 A1 | 4/2012 | Wu et al. |
| 2012/0171668 A1 | 7/2012 | May et al. |
| 2012/0183954 A1 | 7/2012 | Diwu et al. |
| 2012/0238745 A1 | 9/2012 | Diwu et al. |
| 2012/0270242 A1 | 10/2012 | Loshe |
| 2012/0277109 A1 | 11/2012 | Singh et al. |
| 2012/0288871 A1 | 11/2012 | Leung et al. |
| 2012/0301894 A1 | 11/2012 | Agnew et al. |
| 2013/0072666 A1 | 3/2013 | Archer et al. |
| 2013/0109019 A1 | 5/2013 | Murillo et al. |
| 2013/0115594 A1 | 5/2013 | Wei et al. |
| 2013/0210113 A1 | 8/2013 | Diwu et al. |
| 2013/0260379 A1 | 10/2013 | Alexander et al. |
| 2014/0038169 A1 | 2/2014 | Lohse et al. |
| 2014/0141995 A1 | 5/2014 | Crisanti et al. |
| 2014/0147838 A1 | 5/2014 | Sempere et al. |
| 2014/0273088 A1 | 9/2014 | Winther |

FOREIGN PATENT DOCUMENTS

| | | |
|---|---|---|
| EP | 0747448 | 11/2002 |
| EP | 0368684 | 9/2004 |
| EP | 0623679 | 9/2004 |
| EP | 0589877 | 10/2005 |
| GB | 2089055 | 6/1982 |
| JP | H04-504206 | 10/1997 |
| JP | 2010/533842 | 10/2010 |
| JP | 2012-517814 | 8/2012 |
| WO | WO 9011523 | 10/1990 |
| WO | WO 1998/010290 | 3/1998 |
| WO | WO 99/43846 | 9/1999 |
| WO | WO 2000/014281 | 3/2000 |
| WO | WO 2000/067021 | 11/2000 |
| WO | WO 00/75237 | 12/2000 |
| WO | WO 2001/002861 | 1/2001 |
| WO | WO 2002/026891 | 4/2002 |
| WO | WO 2002/028841 | 4/2002 |
| WO | WO 2002/031203 | 4/2002 |
| WO | WO 03/002733 | 1/2003 |
| WO | WO 2003/014375 | 2/2003 |
| WO | WO 2003/020985 | 3/2003 |
| WO | WO 2003/030817 | 4/2003 |
| WO | WO 2003/070984 | 8/2003 |
| WO | WO 2003/076949 | 9/2003 |
| WO | WO 2004/042347 | 5/2004 |
| WO | WO 2004/048935 | 6/2004 |
| WO | WO 04/057307 | 7/2004 |
| WO | WO 04/057308 | 7/2004 |
| WO | WO 04/058404 | 7/2004 |
| WO | WO 04/058950 | 7/2004 |
| WO | WO 04/059284 | 7/2004 |
| WO | WO 04/059287 | 7/2004 |
| WO | WO 04/059288 | 7/2004 |
| WO | WO 04/059297 | 7/2004 |
| WO | WO 04/059441 | 7/2004 |
| WO | WO 04/065491 | 8/2004 |
| WO | WO 2004/077057 | 9/2004 |
| WO | WO 2004/106926 | 12/2004 |
| WO | WO 2005/012579 | 2/2005 |
| WO | WO 2005/021731 | 3/2005 |
| WO | WO 2005/024386 | 3/2005 |
| WO | WO 2005/047242 | 5/2005 |
| WO | WO 2005/047901 | 5/2005 |
| WO | WO 2005/056687 | 6/2005 |
| WO | WO 2005/056689 | 6/2005 |
| WO | WO 2005/123954 | 12/2005 |
| WO | WO 2006/031248 | 3/2006 |
| WO | WO 2006/047452 | 5/2006 |
| WO | WO 2007/015168 | 2/2007 |
| WO | WO 2007015168 | 2/2007 |
| WO | WO 2007/030521 | 3/2007 |
| WO | WO 2007/047450 | 4/2007 |
| WO | WO 2007/050810 | 5/2007 |
| WO | WO 2007/053837 | 5/2007 |
| WO | WO 2007/059779 | 5/2007 |
| WO | WO 2007/075891 | 7/2007 |
| WO | WO 2007/087582 | 8/2007 |
| WO | WO 2008/029281 | 3/2008 |
| WO | WO 2008/029295 | 3/2008 |
| WO | WO 2008/064067 | 5/2008 |
| WO | WO 2008063378 | 5/2008 |
| WO | WO 2008/101024 | 8/2008 |
| WO | WO 2008/109617 | 9/2008 |
| WO | WO 2008128352 | 10/2008 |
| WO | WO 2008/133728 | 11/2008 |
| WO | WO 2008/133729 | 11/2008 |
| WO | WO 2008133728 | 11/2008 |
| WO | WO 2008133729 | 11/2008 |
| WO | WO 2009012140 | 1/2009 |
| WO | WO 2009/018003 | 2/2009 |
| WO | WO 2009/026651 | 3/2009 |
| WO | WO 2009/036700 | 3/2009 |
| WO | WO 2009/036760 | 3/2009 |
| WO | WO 2009036760 | 3/2009 |
| WO | WO 2009/058867 | 5/2009 |
| WO | WO 2009/061402 | 5/2009 |
| WO | WO 2009/067603 | 5/2009 |
| WO | WO 2009/074882 | 6/2009 |
| WO | WO 2009/117138 | 9/2009 |
| WO | WO 2009/117139 | 9/2009 |
| WO | WO 2009/117140 | 9/2009 |
| WO | WO 2009/121550 | 10/2009 |
| WO | WO 2009/134327 | 11/2009 |
| WO | WO 2009/152102 | 12/2009 |
| WO | WO 2010/084284 | 7/2010 |
| WO | WO 2010/094283 | 8/2010 |
| WO | WO 2010/094284 | 8/2010 |
| WO | WO 2010094283 | 8/2010 |
| WO | WO 2010094284 | 8/2010 |
| WO | WO 2010/135480 | 11/2010 |
| WO | WO 2011/026085 | 3/2011 |
| WO | WO 2011/047680 | 4/2011 |
| WO | WO 2011/050069 | 4/2011 |
| WO | WO 2011047680 | 4/2011 |
| WO | WO 2012/003476 | 1/2012 |
| WO | WO 2012/012051 | 1/2012 |
| WO | WO 2012/012595 | 1/2012 |
| WO | WO 2012003476 | 1/2012 |
| WO | WO 2012/054795 | 4/2012 |
| WO | WO 2012/062318 | 5/2012 |
| WO | WO 2012062318 | 5/2012 |
| WO | WO 2012/092322 | 7/2012 |
| WO | WO 2012/143010 | 10/2012 |
| WO | WO 2012143010 | 10/2012 |

OTHER PUBLICATIONS

"Full width at half maximum" from Wikipedia, the free encyclopedia. Printed on Feb. 11, 2015.

Adams JC. Biotin Amplification of Biotin and Horseradish-Peroxidase Signals in Histochemical Stains. J Histochem Cytochem 1992;40: 1457-1463.

Adler K, Erickson T, Bobrow M. High sensitivity detection of HPV-16 in SiHa and CaSki cells utilizing FISH enhanced by TSA. Histochem Cell Biol 1997;108:321-324.

Afonso, A. M. Carlos, et al., "An Expedient Synthesis of Cationic Rhodamine fluorescent Probes Suitable for Conjugation to Amino Acids and Peptides." Synthesis, 2003, 17, 2647-2654.

Asif M, Khadim MT, Mushtaq S, Mamoon N, Akhtar F, Ali Z. Determination of her-2/neu by chromogenic in situ hybridization on borderline (2+) immunohistochemistry cases in carcinoma breast. Asian Pac J Cancer Prev. 2011;12(1):211-4.

Avivi C, Rosen O, Goldstein RS. New chromogens for alkaline phosphatase histochemistry: salmon and magenta phosphate are

(56) References Cited

OTHER PUBLICATIONS useful for single- and double-label immunohistochemistry. J Histochem Cytochem. 1994;42(4):551-4.
Beija, Mariana et al., "Synthesis and applications of Rhodamine derivatives at fluorescent probes." Chem Soc Rev, 2009, 38, 2410-2433.
Katikireddy KR, O'Sullivan F. Immunohistochemical and immunofluorescenee procedures for protein analysis. Methods Mol Biol. 2011;784:155-67.
Bobrow MN, Harris TD, Shaughnessy KJ, Litt GJ. Catalyzed reporter deposition, a novel method of signal amplification. Application to immunoassays. J Immunol Methods 1989;125:279-285.
Bobrow MN, Moen PT Jr. Tyramide signal amplification (TSA) systems for the enhancement of ISH signals in cytogenetics. Curr Protoc Cytom. 2000; Chapter 8(Unit 8.9):pp. 8.9.1-8.9.16.
Bobrow MN, Shaughnessy KJ, Litt GJ. Catalyzed reporter deposition, a novel method of signal amplification. II. Application to membrane immunoassays. J Immunol Methods 1991;137:103-112.
Branidey SM, Wang KK, Harwood AR, et al. The development of a fluorescence in situ hybridization assay for the detection of dysplasia and adenocarcinoma in Barrett's esophagus. J Mol Diagn 2006;8:260-267.
Bratthauer GL. The avidin-biotin complex (ABC) method and other avidin-biotin binding methods In: Immunocytochemical methods and protocols 2010 (pp. 257-270). Humana Press.
Chadwick CS, McEntergart MG, Nairn RC. Fluorescent protein tracers; a trial of new fluorochromes and the development of an alternative to fluorescein. Immunology 1958;1:315-327.
Chao J, DeBiasio R, Zhu Z, et al. Immunofluorescence signal amplification by the enzyme-catalyzed deposition of a fluorescent reporter substrate (CARD). Cytometry 1996;23:48-53.
Dandachi N, Dietze O, Hauser-Kronberger C. Chromogenic in situ hybridization: a novel approach to a practical and sensitive method for the detection of HER2 oncogene in archival human breast carcinoma. Lab Invest. 2002;82(8):1007-14.
Darnell DK, Kaur S, Stanislaw S, Davey S, Konieczka JH, Yatskievych TA, Antin PB. GEISHA: an in situ hybridization gene expression resource for the chicken embryo. Cytogenet Genome Res. 2007;117(1-4):30-5.
Gerami P, Jewell SS, Morrison LE, et al. Fluorescence in situ hybridization (FISH) as an ancillary diagnostic tool in the diagnosis of melanoma. Am J Surg Pathol 2009;33:1146-1156.
Good, N E., et al (1966) Hydrogen ion buffers for biological research Biochem. 5(2), 467-477.
Goto S, Nagahiro S, Ushio Y, Hofer W. A simple enhancement method for the silver-gold-intensified diaminobenzidine reaction in the light microscopic immunoperoxidase technique. J Histochem Cytochem. 1992;40(9):1423-5.
Hameau A, Fuchs S, Laurent R, et al. Synthesis of dye/fluorescent functionalized dendrons based on cyclotriphosphazene. Beilstein J Org Chem 2011;7:1577-1583.
Hoff K, Jørgensen JT, Müller S, Røngaard E, Rasmussen O, Schønau A. Visualization of FISH Probes by dual-color chromogenic in situ hybridization. American journal of clinical pathology. 2010;133(2):205-11.
Hopman AH, Ramaekers FC, Speel EJ. Rapid synthesis of biotin-, digoxigenin-, trinitrophenyl-, and fluorochrome-labeled tyramides and their application for In situ hybridization using CARD amplification. J Histochem Cytochem 1998;46:771-777.
Hoshino S, Ohkoshi N, Watanabe M, Shoji S. Immunohistochemical staining of dystrophin on formalin-fixed paraffin-embedded sections in Duchenne/Becker muscular dystrophy and manifesting carriers of Duchenne muscular dystrophy. Neuromuscul Disord. 2000;10(6):425-9.
Huang, Chusem, et al.; "Versatile Probes for the Selective Detection of Vicinal-Dithiol-Containing proteins: Design, Syntheses, and Applications in Living Cells". Chem. Eur. J. 2013, 19: 7739-7747.
Kerstens HMJ, Poddighe PJ, Hanselaar AGJM. A novel in situ hybridization signal amplification method based on the deposition of biotinylated tyramine. J Histochem Cytochem 1995;43: 347-352.

Kiernan JA. Indigo genie substrates for detection and localization of enzymes. Bioteeh Histoehem. 2007;82(2):73-103.
Kiernan JA. Stability and solubility of 3,3'-diaminobenzidine (DAB). Biotech Histochem. 2003;78(2):135.
Krieg R, Eitner A, Günther W, Halbhuber KJ. Optimization of heterocyclic 4-hydroxystyryl derivatives for histological localization of endogenous and immunobound peroxidase activity. Biotechnic & Histochemistry. 2007 :82(4-5):235-62.
Krieg R, Eitner A, Günther W, Schurer C, Lindenau J, Halbhuber KJ. N, N-Dialkylaminostyryl dyes: specific and highly fluorescent substrates of peroxidase and their application in histochemistry. Journal of molecular histology. 2008,39(2):169-91.
Krieg R, Halbhuber KJ. Detection of endogenous and immunobound peroxidase—the status quo in histochemistry. Prog Histochem Cytochem. 2010;45(2):81-139.
Krieg R, Halbhuber KJ. Novel oxidative self-anchoring fluorescent substrates for the histochemical localization of endogenous and immunobound peroxidase activity. Journal of molecular histology. 2004;35(5):471-87.
Lakos S, Basbaum AI. Benzidine dihydrochloride as a chromogen for single- and double-label light and electron microscopic immunocytochemical studies. J Histochem Cytochem. 1986;34(8):1047-56.
Lanciego JL, Goede PH, Witter MP, Wouterlood FG. Use of peroxidase substrate Vector VIP for multiple staining in light microscopy. J Neurosci Methods. 1997;74(1):1-7.
Lebanony et al., "Diagnostic Assay Based on has-MiR-205 Expression Distinguishes Squamous From Nonsquamous Non-Small-Cell Lung Carcinoma," Journal of Clinical Oncology 2009; 27(12):2030-2037.
Lee H, Mason JC, Achilefu S. Synthesis and spectral properties of near-infrared aminophenyl-, hydroxyphenyl-, and phenyl-substituted heptamethine cyanines. J Org Chem. 2007;73(2):723-5.
Lin J-K, Chang J-Y. Chromophoric labeling of amino acids with 4-dimethylaminoazobenzene-4'-sulfonyl chloride. Analyt Chem 1975;47(9):1634-1638.
Li-Ning-T E, Ronchetti R, Torres-Cabala C, Merino MJ. Role of chromogenic in situ hybridization (CISH) in the evaluation of HER2 status in breast carcinoma: comparison with immunohistochemistry and FISH. Int J Surg Pathol. 2005; 13(4):343-51.
Liu et al., A quantitative evaluation of peroxidase inhibitors for tyramide signal amplification mediated cytochemistry and histochemistry. Histochem. Cell Biol., 2006; 126: 283-291.
Macville MV, Van der Look JA, Speel EJ, Katzir N, Garini Y, Soenksen D, McNamara G, de Wilde PC, Hanselaar AG, Hopman AH, Ried T. Spectral imaging of multi-color chromogenic dyes in pathological specimens. Anal Cell Pathol. 2001;22(3):133-42.
Mason DY, Sammons R. Alkaline phosphatase and peroxidase for double immunoenzymatic labelling of cellular constituents. J Clin Pathol 1978;31:454-460.
Mayr D, Heim S, Weyrauch K, Zeindl-Eberhart E, Kunz A, Engel J, Kirchner T. Chromogenic in situ hybridization for Her-2/neu-oncogene in breast cancer: comparison of a new dual-colour chromogenic in situ hybridization with immunohistochemistry and fluorescence in situ hybridization. Histopathology. 2009;55(6):716-23.
Meguro R, Asano Y, Iwatsuki H, Shoumura K. Perfusion-Perls and -Turnbull methods supplemented by DAB intensification for nonheme iron histochemistry: demonstration of the superior sensitivity of the methods in the liver, spleen, and stomach of the rat. Histochem Cell Biol. 2003;120(1):73-82.
Mollerup J, Henriksen U, Müller S, Schønau A. Dual color chromogenic in situ hybridization for determination of HER2 status in breast cancer: a large comparative study to current state of the art fluorescence in situ hybridization. BMC clinical pathology. 2012;12(1):3.
Henriksen U, Müller S, Schønau A. Dual color CISH and FISH to CISH conversion. Teoksessa Kumar, GL & Rudbeck, L.(Ed.). Dako Education Guide Immunohistocal Staining Methods Fifth Edition. Carpinteria. CA: Dako. 2009:97-101.
Nakane PK, Pierce GB. Enzyme-labeled antibodies: Preparation and application for the localization of antigens. Journal of Histochemistry and Cytochemistry 1966;14:929-931.

(56) References Cited

OTHER PUBLICATIONS

Nakata T, Suzuki N. Chromogen-based immunohistochemical method for elucidation of the coexpression of two antigens using antibodies from the same species. J Histochem Cytochem. 2012;60(8):611-9.
Nguyen T. et al., "Practical synthetic route to rhodamine dyes", Org. Lett. 2003, 18, 3245-48.
Norgren RB Jr, Lehman MN. A new chrome gen for use in HRP-tract tracing and double-label immunocytochemistry. Brain Res Bull. 1990;25(3):393-6.
Ntoulia M, Kaklamanis L, Valavanis C, Kafousi M, Stathopoulos E, Arapantoni P, Mavroudis D, Georgoulias V, Lianidou ES. HER-2 DNA quantification of paraffin-embedded breast carcinomas with LightCycler real-time PCR in comparison to immunohistochemistry and chromogenic in situ hybridization. Clin Biochem. 2006;39(9):942-6.
Öztürk; N; Song; S-H; Özgür, S; Selby, CP; Morrison, L; Parteh; C; Zhong; D; Sanear; A. Structure and function of animal cryptochromes. Cold Spring Harbor Symposia on Quantitative Biology 2007;72:119-131.
Petersen KH. Novel horseradish peroxidase substrates for use in immunohistochemistry. J Immunol Methods. 2009;340(1):86-9.
Petrovic A, Abramovic M, Mihailovic D, Gligorijevic J, Zivkovic V, Mojsilovic M, Ilic I. Multicolor counterstaining for immunohistochemistry—a modified Movat's pentachrome. Biotech Histochem. 2011;86(6):429-35.
Pinaud R, Jeong JK. Duplex in situ hybridization in the study of gene co-regulation in the vertebrate brain. Methods Mol Biol. 2010; 611: 115-29.
Pirnik Z, Kiss A. Detection of oxytocin mRNA in hypertonic saline Fos-activated PVN neurons: comparison of chromogens in dual immunocytochemical and in situ hybridization procedure. Endocr Regul. 2002;36(1):23-30.
Plummer TB, Sperry AC, Xu HS, Lloyd RV. In situ hybridization detection of low copy nucleic acid sequences using catalyzed reporter deposition and its usefulness in clinical human papillomavirus typing. Diagn Mol Pathol. 1998;7(2):76-84.
Punnonen EL, Fages C, Wartiovaara J, Rauvala H. Ultrastructural localization of beta-actin and amphoterin mRNA in cultured cells: application of tyramide signal amplification and comparison of detection methods. J Histochem Cytochem. 1999;47(1):99-112.
Questions and Answers About Tyramide Signal Amplification (TSA) from PerkinElmer, Inc. Printed on Aug. 15, 2015.
Raap AK, van de Corput MP, Vervenne RA, et al. Ultra-sensitive FISH using peroxidase-mediated deposition of biotin- or fluorochrome tyramides. Hum Mol Genet 1995;4:529-534.
Raj A, Peskin CS, Tranchina D, et al. Stochastic mRNA synthesis in mammalian cells. PLoS Biol 2006;4:e309.
Richter B, Fragner K, Weissenböck H. Simultaneous detection of protozoa in the tissues of snakes by double in situ hyindization. Microsc Res Tech. 2008;71(4):257-9.
Sauer T, Beraki K, Noren T, Garred O, Naess O. EGFR gene copy number heterogeneity in fine-needle aspiration cytology from breast carcinomas determined by chromogenic in situ hybridization. Diagn Cytopathol. 2005; 33(4):228-32.
Scorpio, Angelo; Chabot, Donald J; Day, William A; Hoover, Timothy A; Friedlander, Arthur M. Capsule depolymerase overexpression reduces Bacillus anthracis Virulence. Microbiology 2010, 156(5): 1459-1467.
Sholl LM, John Iafrate A, Chou YP, Wu MT, Goan YG, Su L, Huang YT, Christiani DC, Chirieac LR. Validation of chromogenic in situ hybridization for detection of EGFR copy number amplification in nonsmall cell lung carcinoma. Mod Pathol. 2007;20(10):1028-35.
Sokolova IA, Bubendorf L, O'Hare A, et al. A fluorescence in situ hybridization-based assay for improved detection of lung cancer cells in bronchial washing specimens. Cancer 2002;96:306-315.
Speel EJ, Ramaekers FC, Hopman AH. Sensitive multicolor fluorescence in situ hybridization using catalyzed reporter deposition (CARD) amplification. J Histochem Cytochem 1997;45:1439-1446.
Tanner M, Gancberg D, Di Leo A, Larsimont D, Rouas G, Piccart MJ, Isola J. Chromogenic in situ hybridization: a practical alternative for fluorescence in situ hybridization to detect HER-2/neu oncogene amplification in archival breast cancer samples. Am J Pathol. 2000;157(5):1467-72.
Telser, Joshua; Cruickshank; Kenneth A; Morrison; Larry E; Netzel; Thomas L. Synthesis and characterization of DNA oligomers and duplexes containing covalently attached molecular labels: comparison of biotin; fluorescein; and pyrene labels by thermodynamic and optical spectroscopic measurements. Journal of the American Chemical Society 1989; 111(18): 6966-6976.
Thomas MA, Lemmer B. HistoGreen: a new alternative to 3,3'-diaminobenzidine-tetrahydrochloride-dihydrate (DAB) as a peroxidase substrate in immunohistochemistry? Brain Res Protoc. 2005;14(2):107-18.
Trojanowski JQ, Obrocka MA, Lee VM. A comparison of eight different chromogen protocols for the demonstration of immunoreactive neurofilaments or glial filaments in rat cerebellum using the peroxidase-antiperoxidase method and monoclonal antibodies. J Histochem Cytochem. 1983; 31(10): 1217-23.
TSA Signal Amplification (TSA) Systems from PerkinElmer, Inc., pp. 1-16, 2007.
Tyramide Signal Amplification Kits from Molecular Probes, pp. 1 and 2, 2001.
Van der Loos CM. Chromogens in multiple immunohistochemical staining used for visual assessment and spectral imaging: the colorful future. J Histotechnol 2010;33:31-40.
Van der Loos, "User Protocol: Practical Guide to Multiple Staining", Cambridge Research & Instrumentation, Inc. (2009), pp. 1-16.
Van Gijlswijk RP, Zijlmans HJ, Wiegant J, Bobrow MN, Erickson TJ, Adler KE, Tanke HJ, Raap AK. Fluorochrome-labeled tyramides: use in immunocytochemistry and fluorescence in situ hybridization. J Histochem Cytochem. 1997,45(3):375-82.
Van Rijk A, Svenstroup-Poulsen T, Jones M, Cabecadas J, Cigudosa JC, Leoncini L, Mottok A, Bergman CC, Pouliou E, Dutoit SH, van Krieken HJ. Double-staining chromogenic in situ hybridization as a useful alternative to split-signal fluorescence in situ hybridization in lymphoma diagnostics. Haematologica. Feb. 2010,95(2):247-52. Epub Sep. 22, 2009.
Von Bohlen und Halbach O, Kiernan JA. Diaminobenzidine induces fluorescence in nervous tissue and provides intrinsic counterstaining of sections prepared for peroxidase histochemistry. Biotech Histochem. 1999;74(5):236-43.
Xi Chen et al., "An efficient and versatile approach for the preparation of a rhodamine B ester bioprobe library." Dyes and Pigments 2012; 94: 296-303.
Yoo SB, Lee HJ, Park JO, Choe G, Chung DH, Seo JW, Chung JH. Reliability of chromogenic in situ hybridization for epidermal growth factor receptor gene copy number detection in non-small-cell lung carcinomas: a comparison with fluorescence in situ hybridization study. Lung Cancer. Mar. 2010,67(3):301-5. Epub Jun. 7, 2009.
Zhao J, Wu R, Au A, Marquez A, Yu Y, Shi Z. Determination of HERZ gene amplification by chromogenic in situ hybridization (CISH) in archival breast carcinoma. Mod Pathol. 2002;15(6):657-65.
Ochs, Robert L. Methods Used to Study Structure and Function of the Nucleolus. In: Methods in Cell Biology, vol. 53 (1998) pp. 303-321.
Bystryak, S.M. et al., "Photochemical amplification for horseradish peroxidase-mediated immunosorbent assay," Anal. Biochem., 1992, vol. 202, pp. 390-393.
Chao, J. et al., "Immunofluorescence signal amplification by the enzyme-catalyzed deposition of a fluorescent reporter substrate (CARD)," Cytometry, 1996, vol. 23, pp. 48-53.
Mujumdar, R.B. et al., "Cyanine dye labeling reagents containing isothiocyanate groups," Cytometry, 1989, vol. 10, pp. 11-19.
Noland, W.E. et al., "Nitration of indoles. III. Polynitration of 2-alkylindoles," J. Am. Chem. Soc., 1990, vol. 30, pp. 3457-3469.
Pham, W. et al., "Synthesis and application of a water-soluble near-infrared dye for cancer detection using optical imaging," Bioconjugate Chem., 2005, vol. 16, pp. 735-740.
Self, C.H., "Enzyme amplification—a general method applied to provide an immunoassisted assay for placental alkaline phosphatase," J. Immunol. Methods, 1985, vol. 76, pp. 389-393.

(56) References Cited

OTHER PUBLICATIONS

Shragina, L. et al., "Searching for photochromic liquid crystals: Spironaphthoxazine substituted with a mesogenic group," Liquid Crystals, 1990, vol. 7, pp. 643-655.
Crowther, J. "Enzyme-Linked Immunosorbent Assay (ELISA)", in: Molecular Biomethods Handbook, 2nd ed. (2008), pp. 657-682.
Piris, J. et al., "An Immunoperoxidase Technique for the Identification of Gastrin Producing Cells," J. Clin. Path, 1974; 27:798-799.
Figueroa-Espinoza, M. et al., "Oxidative Cross-Linking of Pentosans by a Fungal Laccase and Horseradish Peroxidase: Mechanism of Linkage Between Femloylated Arabinoxylans," Cereal Chem., 1998; 75: 259-265.
Lohse, A. et al., "Solid-Phase Oligosaccharide Tagging (SPOT): Validation on Glycolipid-Derived Structures," Ang. Chemie, 2006; 45: 4167-4172.
Odinot PT, Meis JF. Hoogkamp-Korstanje JA, Melchers WJ. In situ localisation of Yersinia entercolitica by catalysed reported deposition signal amplification. Journal of clinical pathology. 1998;51(6):444-9.
Speel EJ, Hopman AH, Komminoth P. Amplification methods to increase the sensitivity of in situ hybridization: play card (s). Journal of Histochemistry & Cytochemistry. 1999;47(3):281-8.
Shi, S. et al., "Antigen Retrieval Immunohistochemistry: Past, Present and Future," J. Histochem. & Cytochem., 45(3):327-343, (1997).
Kohler, G. et al., "Continuous Cultures of Fused Cells Secreting Antibody of Predefined Specificity," Nature, 256:495-497, (1975).
McCafferty, J., et al., "Phage Antibodies: Filamentous Phage Displaying Antibody Variable Domains," Nature, 348:552-554, (1990).
Kang, S., et al., "Linkage of Recognition and Replication Functions by Assembling combinatorial Antibody Fab Libraries Along Phage Surfaces," Proc. Natl. Acad. Sci., 88:4363-4366, (1991).
Marks, J., et al., "By-Passing Immunization: Building High Affinity Human Antibodies by chain Shuffling," Biotechnology, 10:779-783, (1992).
Waterhouse, P. et al., "Combinatorial Infection and In Vivo Recombination: A Strategy for Making Large Phage Antibody Repertoires," Nucleic Acids Res. 21(9):2265-2266, (1993).
Nielsen, P. "Peptide Nucleic Acid: A Versatile Tool in Genetic Diagnostics and Molecular Biology," Curr Opin Biotech. 12:16-20 (2001).
Sorensen, M., et al., "Functionalized LNA (locked nucleic acid): High-Affinity Hybridization of Oligonucleotides Containing N-Acylated and N-Alkylated 2'-Amino-LNA Monomers," Chem. Commun., 2130-2131, (2003).
Altschul, S., et al., "Gapped BLAST and PSI-BLAST: A new Generation of Protein Database Search Programs," Nucleic Acids Res., 25(17):3389-3402, (1997).

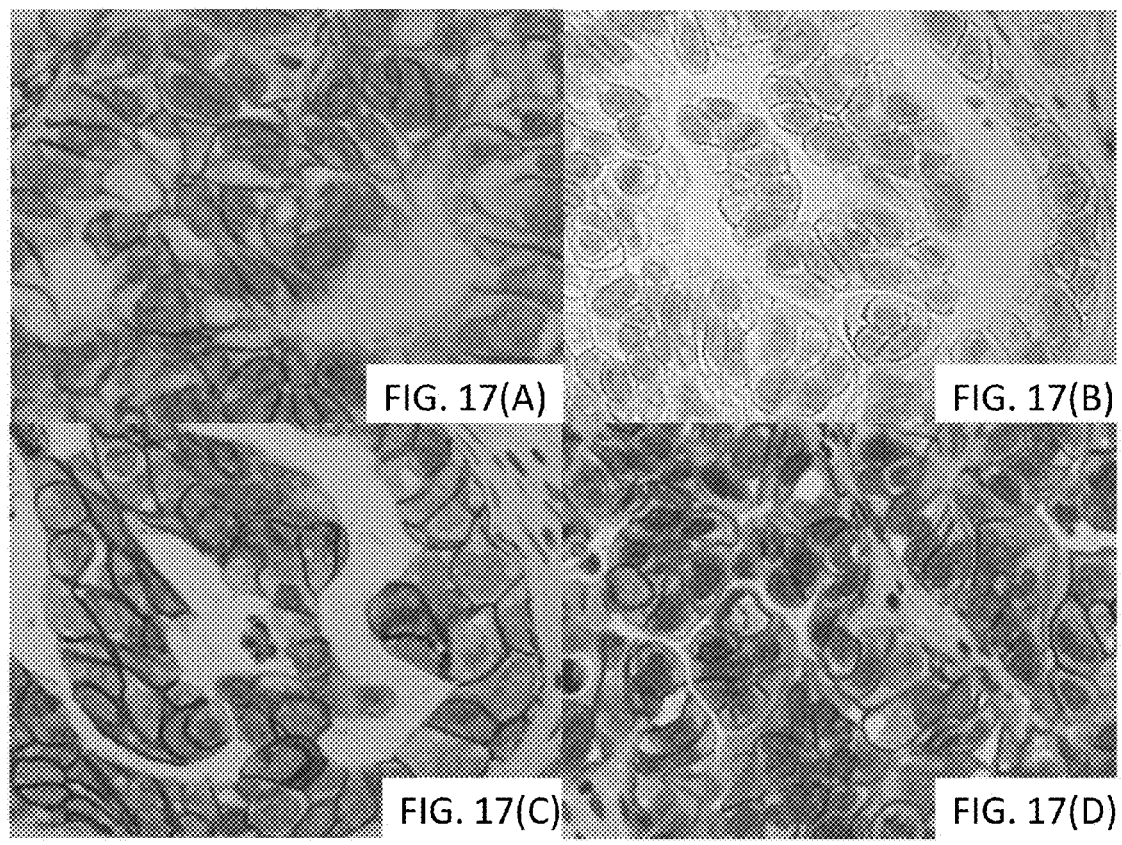
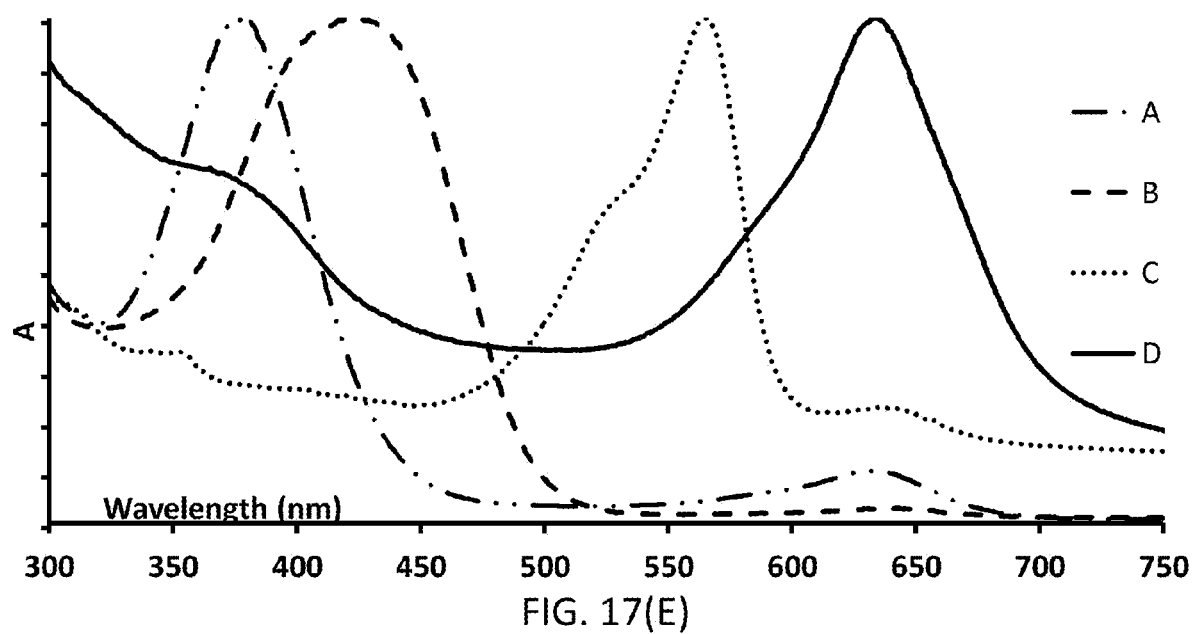
FIG. 17(E)

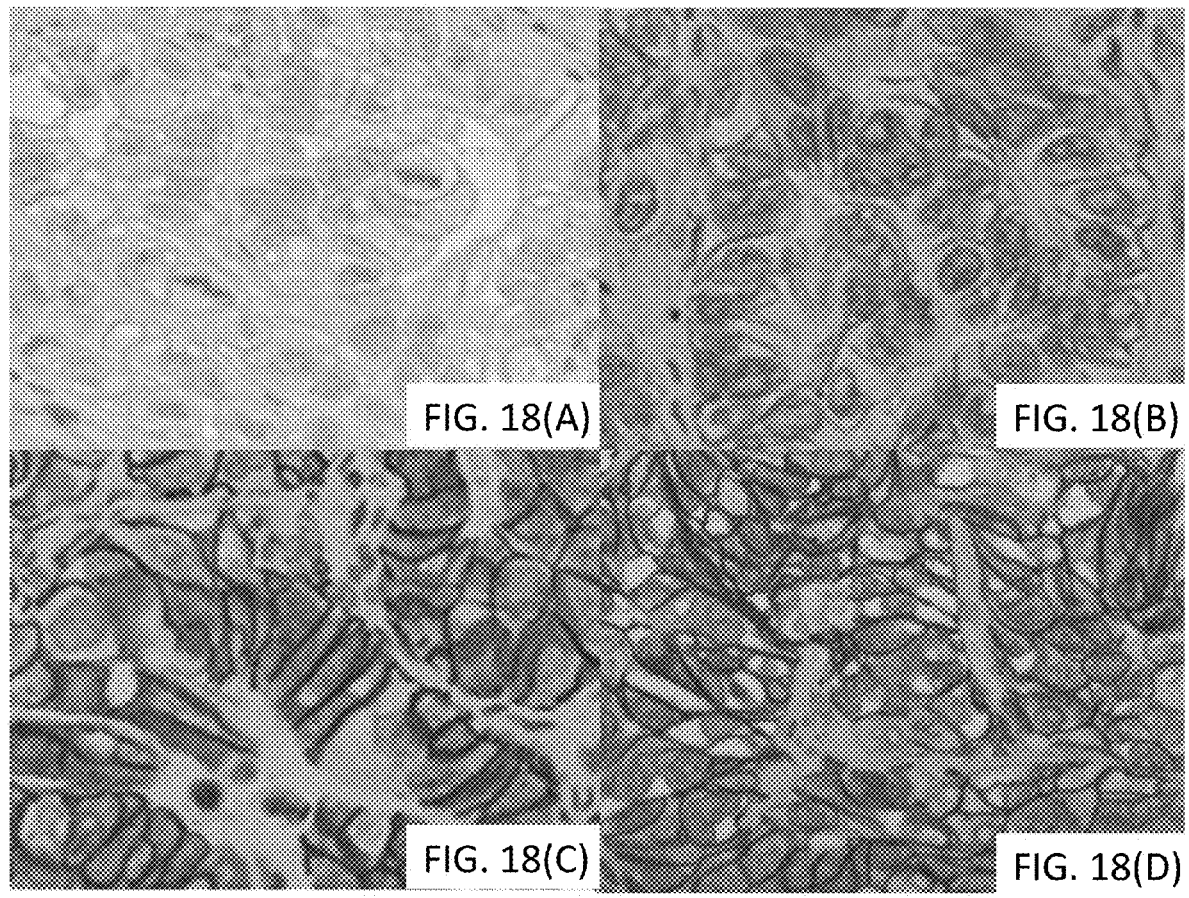
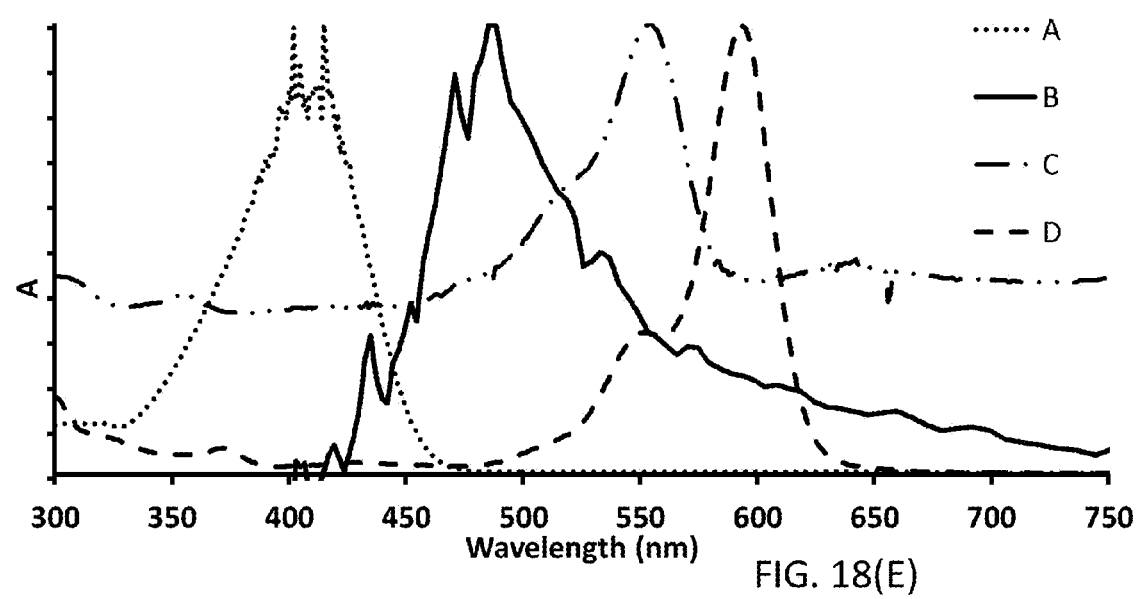
FIG. 18(E)

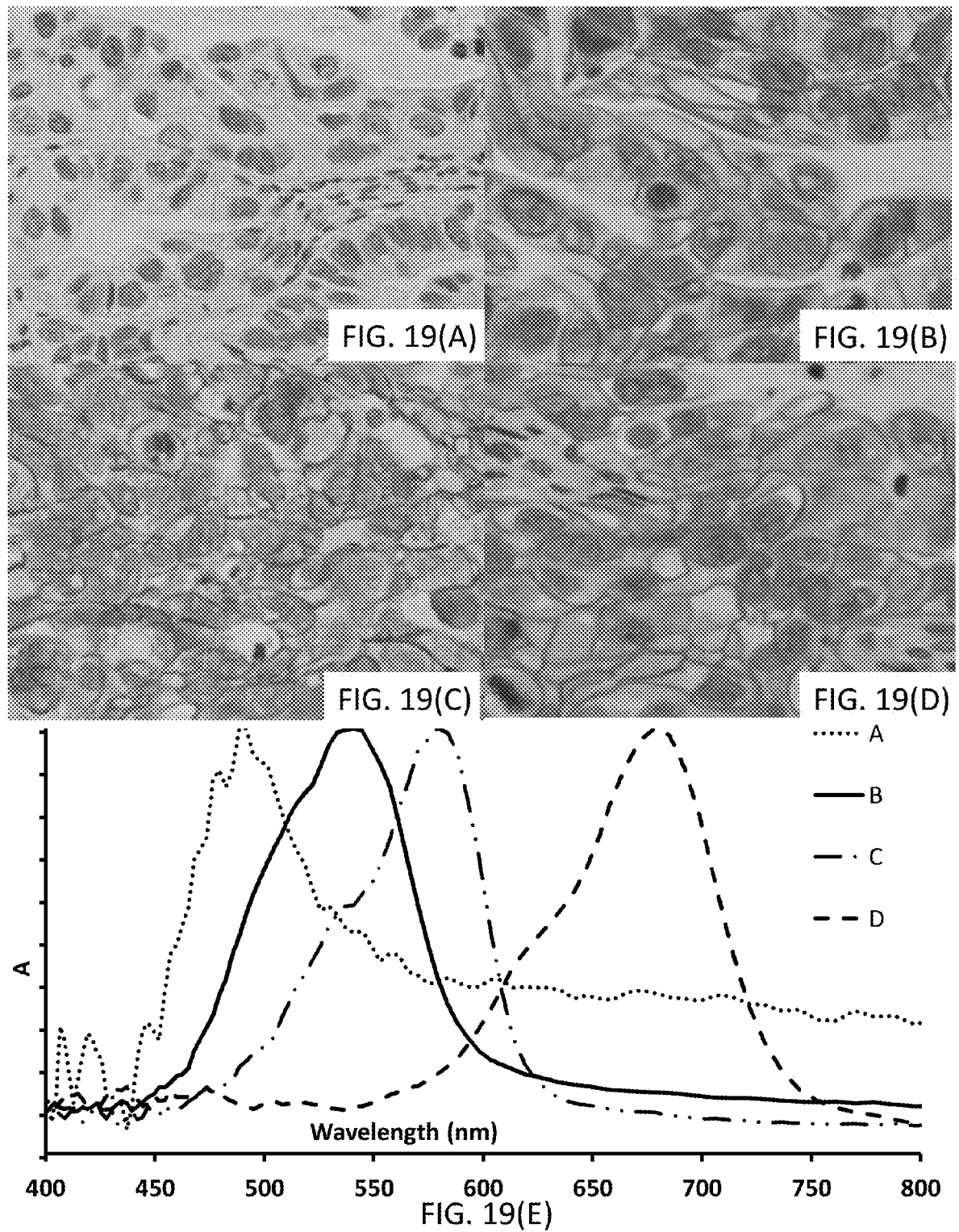

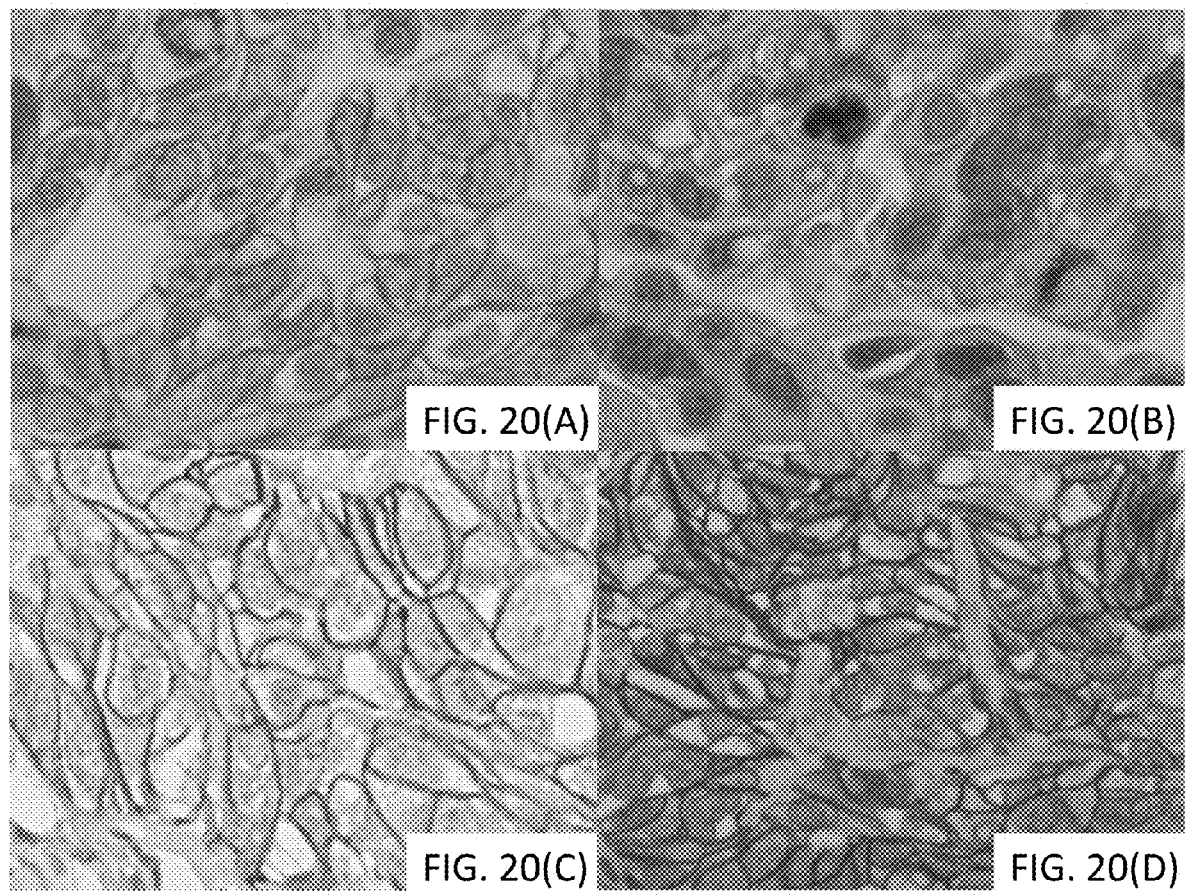
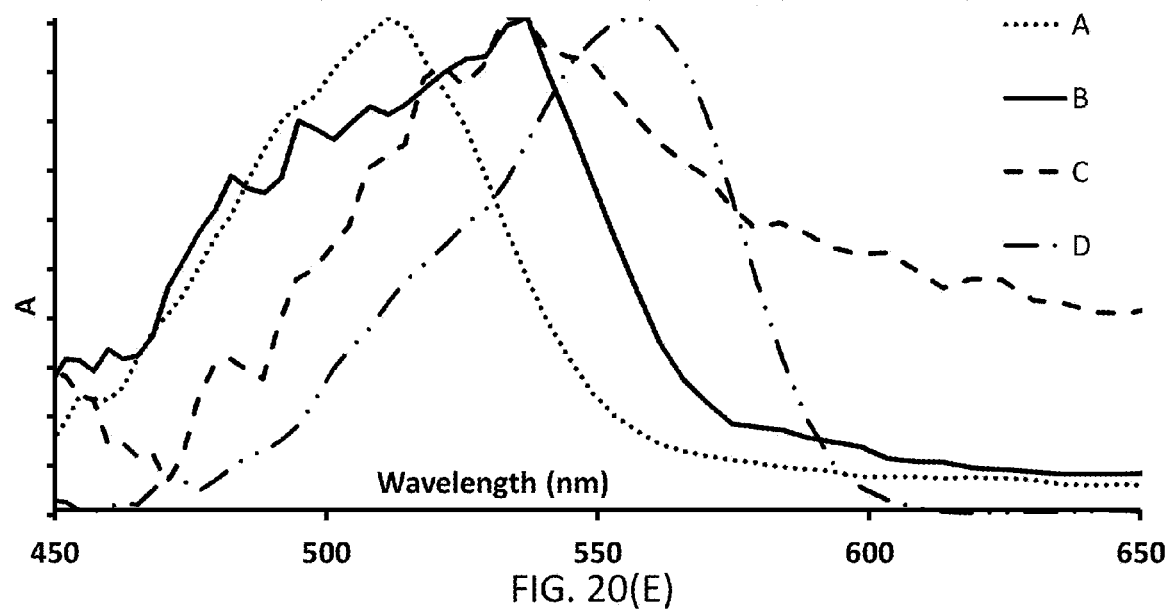
FIG. 20(E)

| Block Lab ID# | HER2 DNA Copy Number | Her2 Protein (IHC) Status | HER2 ACTB Ratio (qPCR) | ACTB mRNA-ISH Signal | HER2 mRNA-ISH Signal |
|---|---|---|---|---|---|
| 26 | Normal | 0 | 0.00 | Positive | 0+ |
| 28 | Normal | 0 | 0.42 | Positive | 0+ |
| 32 | Amplified | 3+ | 3.14 | Negative | 0+ |
| 35 | Normal | 0 | 0.52 | Positive | 1/2+ |
| 36 | Normal | 1+ | 0.94 | Positive | 1/2+ |
| 48 | Amplified | 1+ | 0.06 | Positive | 1/2+ |
| 20 | Amplified | 3+ | 94.59 | Negative | 1/2+ |
| 40 | Normal | 2+ | 4.81 | Positive | 1/2+ |
| 41 | Normal | 2+ | 2.65 | Positive | 1/2+ |
| 43 | Normal | 2+ | 2.99 | Positive | 1/2+ |
| 54 | Normal | 0 | 0.33 | Positive | 1/2+ |
| 7 | Normal | 3+ | 7.41 | Positive | 3+ |
| 8 | Amplified | 3+ | 93.38 | Positive | 3+ |
| 23 | Amplified | 3+ | 0.81 | Positive | 3+ |
| 27 | Amplified | 3+ | 34.68 | Positive | 3+ |
| 30 | Amplified | 3+ | 7.78 | Positive | 3+ |
| 33 | Amplified | 3+ | 7.48 | Positive | 3+ |
| 51 | Amplified | 1+ | 8.19 | Positive | 3+ |
| 56 | Amplified | 3+ | 4.78 | Positive | 3+ |
| 57 | Amplified | 3+ | 5.47 | Positive | 3+ |

FIG. 27

SIGNALING CONJUGATES AND METHODS OF USE

CROSS REFERENCE TO RELATED APPLICATION

This application is a divisional of U.S. Utility application Ser. No. 13/849,160, filed Mar. 22, 2013, now U.S. Pat. No. 10,041,950, which in turn claims the benefit of U.S. Provisional Patent Application No. 61/616,330, filed on Mar. 27, 2012, U.S. Provisional Patent Application No. 61/710,607, filed on Oct. 5, 2012, and U.S. Provisional Patent Application No. 61/778,093, filed on Mar. 12, 2013, all of which are incorporated herein by reference.

FIELD

The present disclosure concerns conjugates, compositions, methods, and kits useful in performing assays for detecting one or more targets within a biological sample.

BACKGROUND

Immunohistochemistry, or IHC, refers to the process of detecting, localizing, and quantifying antigens, such as a protein, in a biological sample, such as a tissue, and using specific binding moieties, such as antibodies specific to the particular antigens. This detection technique has the advantage of being able to show exactly where a given protein is located within the tissue sample. It is also an effective way to examine the tissues themselves. In situ hybridization, or ISH, refers to the process of detecting, localizing, and quantifying nucleic acids. Both IHC and ISH can be performed on various biological samples, such as tissue (e.g., fresh frozen, formalin fixed paraffin embedded) and cytological samples. Upon recognition of the targets, whether the targets be nucleic acids or antigens, the recognition event can be detected through the use of various labels (e.g., chromogenic, fluorescent, luminescent, radiometric).

In situ hybridization (ISH) on tissue includes detecting a nucleic acid by applying a complementary strand of nucleic acid to which a reporter molecule is coupled. Visualization of the reporter molecule allows an observer to localize specific DNA or RNA sequences in a heterogeneous cell population, such as a histological, cytological, or environmental sample. Presently available ISH techniques include silver in situ hybridization (SISH), chromogenic in situ hybridization (CISH) and fluorescence in situ hybridization (FISH).

Interrogation of gene expression in tissue sections using PCR or microarrays has been successfully used to classify patients' likelihood of tumor recurrence and identify those who may benefit from specific therapies. However, tissue specificity and cellular context, which improve the value of tissue-based assays, are lost during the mRNA extraction for PCR or microarray analysis. Moreover, false positive or negative results may be generated from the presence of "contaminating" non-tumor cells in the section. As such, there is a need for automated in situ hybridization assays which target mRNA (mRNA-ISH) that enables robust and reproducible evaluation of biomarker expression while preserving tissue context and specificity, as well as cell-cell relationships.

Chromogenic substrates have been used widely for immunohistochemistry for many years and for in situ hybridization more recently. Chromogenic detection offers a simple and cost-effective method of detection. Traditionally, chromogenic substrates precipitate when activated by the appropriate enzyme. That is, the traditional chromogenic substance is converted from a soluble reagent into an insoluble, colored precipitate upon contacting the enzyme. The resulting colored precipitate requires no special equipment for processing or visualizing. There are several qualities that successful IHC or ISH chromogenic substrates share. First, the substance should precipitate to a colored substance, preferably with a very high molar absorptivity. The enzyme substrate should have high solubility and reagent stability, but the precipitated chromogen products should be very insoluble, preferably in both aqueous and alcohol solutions. Enzyme turnover rates should be very high so as to highly amplify the signal from a single enzyme in a short amount of time. Particular limitations of current chromogenic techniques include the ability to multiplex, incompatibility towards post-staining processing (e.g., solvent washes, drying, subsequent staining), and limited color options.

For in situ assays, such as ISH assays and IHC assays, of tissue and cytological samples, especially multiplexed assays of such samples, it is highly desirable to identify and develop methods that provide desirable results without background interference. Tyramide Signal Amplification (TSA) is a known method based on catalyzed reporter deposition (CARD). U.S. Pat. No. 5,583,001 discloses a method for detection or quantitation of an analyte using an analyte-dependent enzyme activation system relying on catalyzed reporter deposition to amplify the reporter signal enhancing the catalysis of an enzyme in a CARD or TSA method by reacting a labeled phenol molecule with an enzyme. While tyramide signal amplification is known to amplify the visibility of targets, it is also associated with elevated background staining (e.g., amplification of non-specific recognition events).

SUMMARY

Disclosed herein are signaling conjugates, particularly chromogen conjugates and methods of using the signaling conjugates to detect targets within samples. The disclosed chromogen-containing compositions and kits including the same, may be used to detect targets in various analyses or assays. In preferred embodiments, the targets are from a biological sample. Illustrative targets include proteins and nucleic acids being analyzed in the context of anatomical pathology or cytology. One aspect of the disclosure is that the chromogen conjugates are fully compatible with automated slide staining instruments and processes. The chromogen conjugates enable previously unattainable detection sensitivity and multiplexing capability, amongst various other advantages, thus representing a significant advancement to the state of the art.

In illustrative embodiments, a method of detecting a target in a biological sample includes contacting the biological sample with a detection probe, contacting the biological sample with a labeling conjugate, and contacting the biological sample with a signaling conjugate. The labeling conjugate includes an enzyme. The signaling conjugate includes a latent reactive moiety and a chromogenic moiety. The enzyme catalyzes conversion of the latent reactive moiety into a reactive moiety which covalently binds to the biological sample proximally to or directly on the target. The method further includes illuminating the biological sample with light and detecting the target through absorbance of the light by the chromogenic moiety of the signaling conjugate. In one embodiment, the reactive moiety reacts with a tyrosine residue of the biological sample, the enzyme conjugate, the detection probe, or combinations thereof.

In illustrative embodiments, the detection probe is an oligonucleotide probe or an antibody probe. In further illustrative embodiments, the labeling conjugate includes an antibody coupled to the enzyme. Exemplary enzymes include oxidoreductases or peroxidases. An exemplary antibody for the labeling conjugate would be an anti-species or an anti-hapten antibody. The detection probe may include a hapten selected from the group consisting an oxazole hapten, pyrazole hapten, thiazole hapten, nitroaryl hapten, benzofuran hapten, triterpene hapten, urea hapten, thiourea hapten, rotenoid hapten, coumarin hapten, cyclolignan hapten, di-nitrophenyl hapten, biotin hapten, digoxigenin hapten, fluorescein hapten, and rhodamine hapten. In other examples, the detection probe is monoclonal antibody derived from a second species such as goat, rabbit, mouse, or the like. The labeling conjugate is configured, through its inclusion of an anti-species or an anti-hapten antibody to bind selectively to the detection probe.

One aspect of the present disclosure is that the signaling conjugates disclosed herein may be configured to absorb light more selectively than traditionally available components, such as traditional chromogens. Detection is realized by absorbance of the light by the signaling conjugate; for example, absorbance of at least about 5% of incident light would facilitate detection of the target. In other darker stains, at least about 20% of incident light would be absorbed. Non-uniform absorbance of light within the visible spectrum results in the chromophore moiety appearing colored. The signaling conjugates disclosed herein may appear colored due to their absorbance; the signaling conjugates may appear to provide any color when used in the assay, with certain particular colors including red, orange, yellow, green, indigo, or violet depending on the spectral absorbance associated with the chromophore moiety contained therein. According to another aspect, the chromophore moieties may have narrower spectral absorbances than those absorbances of traditionally used chromogens (e.g., DAB, Fast Red, Fast Blue). In illustrative embodiments, the spectral absorbance associated with the first chromophore moiety of the first signaling conjugate has a full-width half-max (FWHM) of between about 30 nm and about 250 nm, between about 30 nm and about 150 nm, between about 30 nm and about 100 nm, or between about 20 nm and about 60 nm.

Narrow spectral absorbances enable the signaling conjugate chromophore moiety to be analyzed differently than traditional chromogens. While having enhanced features compared to traditionally chromogens, detecting the signaling conjugates remains simple. In illustrative embodiments, detecting comprises using a bright-field microscope or an equivalent digital scanner. The narrow spectral absorbances enable chromogenic multiplexing at level beyond the capability of traditional chromogens. For example, traditional chromogens are somewhat routinely duplexed (e.g., Fast Red and Fast Blue, Fast Red and Black (silver), Fast Red and DAB). However, triplexed or three-color applications, or greater, are atypical, as it becomes difficult to discern one chromophore from another. In illustrative embodiments of the presently disclosed technology, the method includes detecting from two to at least about six different targets using different signaling conjugates or combinations thereof. In one embodiment, illuminating the biological sample with light comprises illuminating the biological sample with a spectrally narrow light source, the spectrally narrow light source having a spectral emission with a second full-width half-max (FWHM) of between about 30 nm and about 250 nm, between about 30 nm and about 150 nm, between about 30 nm and about 100 nm, or between about 20 nm and about 60 nm. In another embodiment, illuminating the biological sample with light includes illuminating the biological sample with an LED light source. In another embodiment, illuminating the biological sample with light includes illuminating the biological sample with a filtered light source.

In illustrative embodiments, detecting targets within the sample includes contacting the biological sample with a first amplifying conjugate that is covalently deposited proximally to or directly on the first labeling conjugate. The first amplifying conjugate may be followed by contacting the biological sample with a secondary labeling conjugate. Illustratively, the amplification of signal using amplifying conjugates enhances signaling conjugate deposition. The enhanced signaling conjugate deposition enables easier visual identification of the chromogenic signal, that is, the amplification makes the color darker and easier to see. For low expressing targets, this amplification may result in the signal becoming sufficiently dark to be visible, whereas without amplification, the target would not be apparent. In one embodiment, the signaling conjugate is covalently deposited proximally to the target at a concentration of greater than about $1 \times 10^{11}$ molecules per $cm^2 \cdot \mu m$ to about $1 \times 10^{16}$ molecules per $cm^2 \cdot \mu m$ of the biological sample. In one embodiment, the first target and the second target are genetic nucleic acids. Detecting the first target through absorbance of the light by the first signaling conjugate includes detecting, in an exemplary embodiment, a first colored signal selected from red, orange, yellow, green, indigo, or violet, the first colored signal associated with spectral absorbance associated with the first chromogenic moiety of the first signaling conjugate. Detecting the second target through absorbance of the light by the second signaling conjugate includes detecting, in an exemplary embodiment, a second colored signal selected from red, orange, yellow, green, indigo, or violet, the second colored signal associated with spectral absorbance associated with the second chromogenic moiety of the second signaling conjugate. Detecting also may comprise viewing an overlap in proximity through absorbance of the light by the first signaling conjugate overlapping in proximity with the second signaling conjugate so that a third colored signal associated with overlapping spectral absorbance of the first spectral absorbance and the second spectral absorbance. According to one example, this third colored signals a normal genetic arrangement and the first and second colors signal a genetic rearrangement or translocation.

Also disclosed herein are compositions comprising a biological sample comprising one or more enzyme-labeled targets and a plurality of signaling conjugates comprising a chromogenic moiety. The signaling conjugates are configured to bind proximally to or directly on the one or more targets in the biological sample and are configured to provide a bright-field signal.

In particular disclosed embodiments of the composition, "configured to provide a bright-field signal" comprises absorbing 5% or more of incident light. In another embodiment of the composition, "configured to provide a bright-field signal" comprises absorbing 20% or more of incident light. In particular disclosed embodiments of the composition, "configured to provide a bright-field signal" comprises having an absorbance peak with a $\lambda_{max}$ of between about 350 nm and about 800 nm. In one embodiment, "configured to provide a bright-field signal" comprises having an absorbance peak with a $\lambda_{max}$ of between about 400 nm and about 750 nm. In another embodiment, "configured to provide a bright-field signal" comprises having an absorbance peak with a $\lambda_{max}$ of between about 400 nm and about 700 nm. In yet another embodiment, "configured to provide a bright-field signal" comprises having a first absorbance peak with a first $\lambda_{max}$ of between about 350 nm and about 500 nm, and a second absorbance peak with a second $\lambda_{max}$ of between about 500 nm and about 800 nm. In another embodiment, "configured to provide a bright-field signal" comprises having a first absorbance peak with a first $\lambda_{max}$ of between about 400 nm and about 500 nm, and a second absorbance peak with a second $\lambda_{max}$ of between about 500 nm and about 750 nm. In yet another embodiment, "configured to provide a bright-field signal" comprises having a first absorbance peak with a first $\lambda_{max}$ of between about 350 nm and about 450 nm, and a second absorbance peak with a second $\lambda_{max}$ of between about 450 nm and about 600 nm. In another embodiment, "configured to provide a bright-field signal" comprises having a first absorbance peak with a first $\lambda_{max}$ of between about 350 nm and about 450 nm, and second absorbance peak with $\lambda_{max}$ of between about 600 nm and about 800 nm.

The composition also may comprise a plurality of signaling conjugates configured to have an absorbance peak with a full-width half-max (FWHM) of between about 30 nm and about 250 nm. In one embodiment, a plurality of signaling conjugates is configured to have an absorbance peak with a full-width half-max (FWHM) of between about 30 nm and about 150 nm. In another embodiment, a plurality of signaling conjugates is configured to have an absorbance peak with a full-width half-max (FWHM) of between about 30 nm and about 100 nm. In yet another embodiment, a plurality of signaling conjugates is configured to have an absorbance peak with a full-width half-max (FWHM) of between about 20 nm and about 60 nm.

The composition also may comprise signaling conjugates wherein at least a portion of the plurality of signaling conjugates has an average molar absorptivity of greater than about 5,000 $M^{-1}$ $cm^{-1}$ to about 90,000 $M^{-1}$ $cm^{-1}$. In one embodiment, at least a portion of the plurality of signaling conjugates has an average molar absorptivity of greater than about 10,000 $M^{-1}$ $cm^{-1}$ to greater than about 80,000 $M^{-1}$ $cm^{-1}$. In another embodiment, at least a portion of the plurality of signaling conjugates has an average molar absorptivity of greater than about 20,000 $M^{-1}$ $cm^{-1}$ to greater than about 80,000 $M^{-1}$ $cm^{-1}$. In yet another embodiment, at least a portion of the plurality of signaling conjugates has an average molar absorptivity of greater than about greater than about 40,000 $M^{-1}$ $cm^{-1}$ to greater than about 80,000 $M^{-1}$ $cm^{-1}$.

In particular disclosed embodiments, the composition may comprise a plurality of signaling conjugates wherein at least a portion of the plurality of signaling conjugates has a solubility in water of at least about 0.1 mM to about 1 M. In one embodiment, at least a portion of the plurality of signaling conjugates has a solubility in water of at least about 1 mM to about 1 M. In another embodiment, at least a portion of the plurality of signaling conjugates has a solubility in water of at least about 10 mM to about 1 M. In yet another embodiment, at least a portion of the plurality of signaling conjugates has a solubility in water of at least about 100 mM to about 1M.

The disclosed composition also may comprise a plurality of signaling conjugates that are stable against precipitation in an aqueous buffered solution for greater than about 1 month to about 30 months. In one embodiment, a plurality of signaling conjugates is stable against precipitation in an aqueous buffered solution for greater than 12 months.

In particular disclosed embodiments, a plurality of signaling conjugates are configured to provide an optically apparent color under bright-field illumination. The optically apparent color in exemplary embodiments is selected from red, orange, yellow, green, indigo, violet, and mixtures thereof. In particular disclosed embodiments, "configured to provide a bright-field signal" comprises imparting a first optically distinct color and a second optically distinct color. In one embodiment, configured to provide a bright-field signal comprises imparting a third color optically distinct from the first optically distinct color and the second optically distinct color. In yet another embodiment, configured to provide the bright-field signal comprises imparting a fourth color optically distinct from the first optically distinct color, the second optically distinct color, and the third optically distinct color.

In particular disclosed embodiments of the composition, the biological sample is a tissue or cytology sample. The tissue or cytology sample, such as a formalin-fixed, paraffin embedded sample, may be mounted on a glass microscope slide for use with an automated slide staining instrument.

In certain embodiments, the biological sample comprises a first target and the plurality of signaling conjugates are located proximally to the first target. The biological sample also may further comprise a second target and a second population of the plurality of signaling conjugates that are located proximally to the second target, wherein the first target and the second target are different. In one embodiment, a first detection probe is used to detect a first target and a second detection probe is used to detect the second target.

Also disclosed herein are embodiments of a kit comprising a signaling conjugate having a latent reactive moiety and a chromogenic moiety as disclosed herein. In one embodiment, the kit further comprises a peroxide solution. In another embodiment, the kit further comprises an amplifying conjugate and an enzyme conjugate.

The present disclosure contains information related to the International Application entitled "Signaling Conjugates and Methods of Use," filed on Mar. 22, 2013. The entirety of this international application is incorporated herein by reference.

The foregoing and other objects, features, and advantages of the presently disclosed technology will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2(A-B) are schematic diagrams of embodiments of two signaling conjugates.

FIGS. 3(A-F) are schematic diagrams illustrating a manner in which a target on a sample is detected.

FIGS. 5(A-B) are schematics showing the differences between signals obtained with chromogens and signals obtained with fluorophores.

FIGS. 6(A-B) are images illustrating the color characteristics discussed herein.

FIGS. 7(A-B) are images illustrating results from a particular embodiment of the disclosed method.

FIGS. 8(A-B) are images illustrating results obtained from a particular embodiment of the disclosed method.

FIGS. 9(A-B) are graphs of absorbance versus wavelength and illustrate the two sets of traces provided in FIG. 8(B). FIG. 9(A) illustrates the traces obtained from tissue samples, whereas

FIGS. 10(A-B) are images and a schematic illustrating the difference between a dual ISH chromogenic detection, where

FIGS. 13(A-B) are photomicrographs, where

FIGS. 14(A-B) are photomicrographs showing a sample stained with a signaling conjugate, where

FIGS. 17(A-E) show photomicrographs (FIG. 17(A-D)) of tissues stained with signaling conjugates having different chromogenic moieties, and FIG. 17(E) shows UV-Vis spectra with traces corresponding to the absorbance of the signaling conjugates, the traces corresponding to the associated photomicrograph.

FIGS. 18(A-E) show (A-D) photomicrographs of tissues stained with signaling conjugates having different chromogenic moieties. FIG. 18(E) shows UV-Vis spectra with traces corresponding to the absorbance of the signaling conjugates, the traces corresponding to the associated photomicrograph.

FIGS. 19(A-E) show (A-D) photomicrographs of tissues stained with signaling conjugates having different chromogenic moieties. FIG. 19(E) shows UV-Vis spectra with traces corresponding to the absorbance of the signaling conjugates, the traces corresponding to the associated photomicrograph.

FIGS. 20(A-E) show (A-D) photomicrographs of tissues stained with signaling conjugates having different chromogenic moieties. FIG. 20(E) shows UV-Vis spectra with traces corresponding to the absorbance of the signaling conjugates, the traces corresponding to the associated photomicrograph.

FIGS. 21(A-B) are photomicrographs of a tonsil tissue sample comprised of normal non-cancerous B cells, where

FIGS. 23(A-B) are photomicrographs, where

FIGS. 25(A-B) are photomicrographs of breast tissue, where

FIGS. 26(A-C) are photomicrographs of breast tissue samples showing dual staining of ACTB, where

FIG. 27 is data from a number of tissue blocks comparing the results of HER2 ISH analysis, HER2 IHC analysis, and HER2 mRNA two-color ISH.

FIGS. 28(A-B) are photomicrographs illustrating direct detection of the gene PTEN using a DNA ISH assay incorporating direct deposition of a Rhod-tyramide conjugate.

FIGS. 35(A-C) are photomicrographs illustrating direct detection of gene targets in Calu-3 cells using an mRNA ISH assay.

DETAILED DESCRIPTION

I. Definitions and Abbreviations

Figure 1:
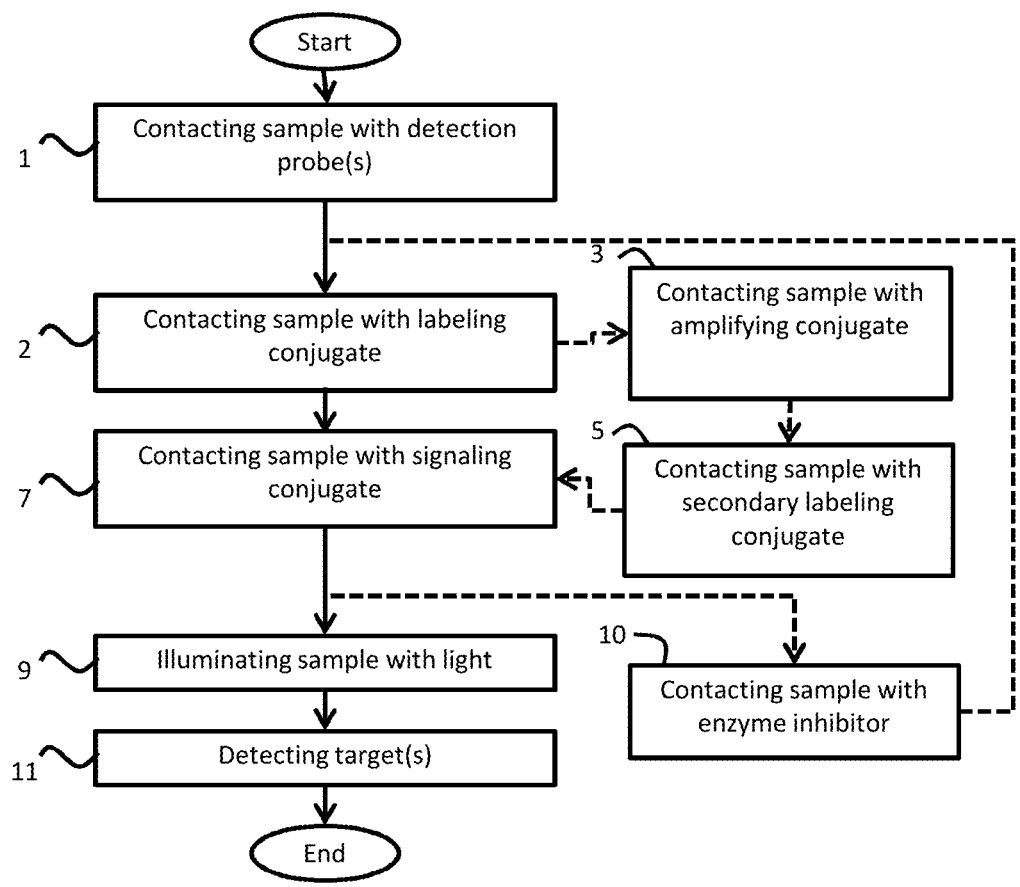
FIG. 1 is a flowchart providing the steps of one embodiment of the method.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Disclosed herein are one or more generic chemical formulas. For the general formulas provided herein, if no substituent is indicated, a person of ordinary skill in the art will appreciate that the substituent is hydrogen. A bond that is not connected to an atom, but is shown, for example, extending to the interior of a ring system, indicates that the position of such substituent is variable. A curved line drawn through a bond indicates that some additional structure is bonded to that position, typically a linker or the functional group or moiety used to couple two moieties together (e.g., a chromophore and a tyramide or tyramide derivative). Moreover, if no stereochemistry is indicated for compounds having one or more chiral centers, all enantiomers and diasteromers are included. Similarly, for a recitation of aliphatic or alkyl groups, all structural isomers thereof also are included. Unless otherwise stated, R groups (e.g., $R^1$-$R^{24}$) in the general formulas provided below independently are selected from: hydrogen; acyl; aldehyde; alkoxy; aliphatic, particularly lower aliphatic (e.g., $C_{1-10}$alkyl, $C_{1-10}$alkylene, $C_{1-10}$alkyne); substituted aliphatic; heteroaliphatic (e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl); substituted alkyl, such as alkyl halide (e.g., —$CX_3$ where X is a halide, and combinations thereof, either in the chain or bonded thereto); oxime; oxime ether (e.g., methoxyimine, $CH_3$—O—N=); alcohols (i.e., aliphatic or alkyl hydroxyl, particularly lower alkyl hydroxyl); amido; amino; amino acid; aryl; alkyl aryl, such as benzyl; carbohydrates; monosaccharides, such as glucose and fructose; disaccharides, such as sucrose and lactose; oligosaccharides; polysaccharides; carbonyl; carboxyl; carboxylate (including salts thereof, such as Group I metal or ammonium ion carboxylates); cyclic; cyano (—CN); ester, such as alkyl ester; ether; exomethylene; halogen; heteroaryl; heterocyclic; hydroxyl; hydroxylamine; keto, such as aliphatic ketones; nitro; sulfhydryl; sulfonyl; sulfoxide; exomethylene; and combinations thereof.

"Absorbance" or "Absorption" refers to the logarithmic ratio of the radiation incident upon a material ($P_0$), to the radiation transmitted through a material (P). The absorbance A of a material varies with the light path length through it (z) according to Equation 1.

$$A = \log\frac{P_0}{P} = -(\log T) = \varepsilon l c \qquad \text{Equation 1}$$

$P_0$ and P are the incident and transmitted light intensities, T is the optical transmission, and c is the molar extinction coefficient ($M^{-1}$ $cm^{-1}$), l is the length or depth of illuminated area (cm), and c is the concentration of the absorbing molecule.

"Amplification" refers to the act or result of making a signal stronger.

"Amplifying conjugate" refers to a molecule comprising a latent reactive species coupled to a hapten, such as, for example, a hapten-tyramide conjugate. The amplifying conjugate may serve as a member of a specific binding pair, such as, for example, an anti-hapten antibody specifically binding to the hapten. The amplification aspect relates to the latent reactive species being enzymatically converted to a reactive species so that a single enzyme can generate a multiplicity of reactive species. Reference is made to U.S. Pat. No. 7,695,929, which is hereby incorporated by reference, in its entirety.

"Antibody," occasionally abbreviated "Ab", refers to immunoglobulins or immunoglobulin-like molecules (including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least 103 M-1 greater, at least 104 M-1 greater or at least 105 M-1 greater than a binding constant for other molecules in a biological sample. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art. Antibody fragments include proteolytic antibody fragments [such as F(ab')2 fragments, Fab' fragments, Fab'-SH fragments and Fab fragments as are known in the art], recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079, 5,874,541; 5,840,526; 5,800,988; and 5,759,808). The term "antibody" includes monoclonal antibody which are characterized by being produced by a single clone of B lymphocytes or by a cell into which the light and heavy chain genes of a single antibody have been transfected. Monoclonal antibodies are produced by methods known to those of skill in the art. Monoclonal antibodies include humanized monoclonal antibodies.

"Antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

"Chromophore" refers to a molecule or a part of a molecule responsible for its color. Color arises when a molecule absorbs certain wavelengths of visible light and transmits or reflects others. A molecule having an energy difference between two different molecular orbitals falling within the range of the visible spectrum may absorb visible light and thus be aptly characterized as a chromophore. Visible light incident on a chromophore may be absorbed thus exciting an electron from a ground state molecular orbital into an excited state molecular orbital.

"Conjugate" refers to two or more molecules that are covalently linked into a larger construct. In some embodiments, a conjugate includes one or more biomolecules (such as peptides, nucleic acids, proteins, enzymes, sugars, polysaccharides, lipids, glycoproteins, and lipoproteins) covalently linked to one or more other molecules, such as one or more other biomolecules. In other embodiments, a conjugate includes one or more specific-binding molecules (such as antibodies and nucleic acid sequences) covalently linked to one or more detectable labels (haptens, enzymes and combinations thereof). In other embodiments, a conjugate includes one or more latent reactive moieties covalently linked to detectable labels (haptens, chromophore moieties, fluorescent moieties).

"Conjugating," "joining," "bonding," "coupling" or "linking" are used synonymously to mean joining a first atom or molecule to another atom or molecule to make a larger molecule either directly or indirectly.

"DABSYL" refers to 4-(dimethylamino)azobenzene-4'-sulfonamide, a yellow-orange chromophore.

"Derivative" refers to a compound that is derived from a similar compound by replacing one atom or group of atoms with another atom or group of atoms.

"Enhanc(e/er/ement/ing)" An enhancer or enhancing reagent is any compound or any combination of compounds sufficient to increase the catalytic activity of an enzyme, as compared to the enzyme activity without such compound(s). Enhancer(s) or enhancing reagent(s) can also be defined as a compound or combination of compounds that increase or accelerate the rate of binding an activated conjugate to a receptor site. Enhanc(e/ement/ing) is a process by which the catalytic activity of an enzyme is increased by an enhancer, as compared to a process that does not include such an enhancer. Enhanc(e/ement/ing) can also be defined as increasing or accelerating the rate of binding of an activated conjugate to a receptor site. Enhanc(e/ement/ing) can be measured visually, such as by scoring by a pathologist. In particular embodiments, scores range from greater than 0 to greater than 4, with the higher number indicating better visual detection. More typically, scores range from greater than 0 to about 4++, such as 1, 1.5, 2, 2.5, 3, 3.5, 3.75, 4, 4+, and 4++. In addition, enhanc(e/ement/ing) can be measured by determining the apparent $V_{max}$ of an enzyme. In particular embodiments, the term encompasses apparent $V_{max}$ values (measured as optical density/minute) ranging from greater than 0 mOD/min to about 400 mOD/min, such as about 15 mOD/min, 18 mOD/min, about 20 mOD/min, about 40 mOD/min, about 60 mOD/min, about 80 mOD/min, about 100 mOD/min, about 120 mOD/min, about 140 mOD/min, about 160 mOD/min, about 200 mOD/min, about 250 mOD/min, about 300 mOD/min, about 350 mOD/min, and about 400 mOD/min. More typically, the Vmax ranges from greater than 0 mOD/min to about 160 mOD/min, such as about 20 mOD/min, about 40 mOD/min, about 60 mOD/min, about 80 mOD/min, about 100 mOD/min, about 120 mOD/min, about 140 mOD/min, and about 160 mOD/min. In addition, enhancement can occur using any concentration of an enhancer greater than 0 mM. Reference is made to US Pat. Publ. No. 2012/0171668, which is hereby incorporated by reference in its entirety, for disclosure related to enhancers useful within the present disclosure.

"Epitope" refers to an antigenic determinant. These are particular chemical groups or contiguous or non-contiguous peptide sequences on a molecule that are antigenic, that is, that elicit a specific immune response. An antibody binds a particular antigenic epitope.

"Functional group" refers to a specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), and disulfide.

"FWHM" refers to the full width of an absorbance peak at the half maximum absorbance.

"Hapten" refers to a molecule, typically a small molecule, which can combine specifically with an antibody, but typically is substantially incapable of being immunogenic on its own.

"Linker" refers to a molecule or group of atoms positioned between two moieties. For example, a signaling conjugate may include a chemical linker between the chromophore moiety and a latent reactive moiety. Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker.

"MG" refers to Malachite green.

"Moiety" refers to a fragment of a molecule, or a portion of a conjugate.

"Molecule of interest" or "Target" each refers to a molecule for which the presence, location and/or concentration is to be determined. Examples of molecules of interest include proteins and nucleic acid sequences.

"Multiplex, -ed, -ing" refers to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

"Proximal" refers to being situated at or near the reference point. As used herein, proximal means within about 5000 nm, within about 2500 nm, within about 1000 nm, within about 500 nm, within about 250 nm, within about 100 nm, within about 50 nm, within about 10 nm, or within about 5 nm of the reference point.

"Reactive groups" refers to a variety of groups suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

"Rhod" refers to Rhodamine, a chromophore.

"Sample" refers to a biological specimen containing genomic DNA, RNA (including mRNA), protein, or combinations thereof, obtained from a subject. Examples include, but are not limited to, peripheral blood, urine, saliva, tissue biopsy, surgical specimen, amniocentesis samples and autopsy material.

"Specific binding moiety" refers to a member of a specific-binding pair. Specific binding pairs are pairs of molecules that are characterized in that they bind each other to the substantial exclusion of binding to other molecules (for example, specific binding pairs can have a binding constant that is at least 103 $M^{-1}$ greater, 104 $M^{-1}$ greater or 105 $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A), nucleic acid sequences, and protein-nucleic acids. Specific binding moieties can also include the molecules (or portions thereof) that are specifically bound by such specific binding proteins. Exemplary specific binding moieties include, but are not limited to, antibodies, nucleotides, oligonucleotides, proteins, peptides, or amino acids.

"TAMRA" refers to Carboxytetramethylrhodamine, a pink rhodamine chromophore.

"TMR" refers to Tetramethylrhodamine, a red rhodamine chromophore.

"TSA" refers to tyramide signal amplification.

"TYR" refers to tyramine, tyramide, tyramine and/or tyramide derivatives.

II. Methods for Detecting a Target in a Sample

Disclosed herein are embodiments of a method for using disclosed exemplary conjugates for detecting one or more targets in a biological sample. In particular disclosed embodiments, one or more of the conjugates are used in standard assays, such as in situ hybridization (ISH), immunocytochemical, and immunohistochemical (IHC) detection schemes. In particular disclosed embodiments, any one of these assays may be combined with signal amplification, and/or the assays may concern multiplexing wherein multiple different targets may be detected. Particular disclosed embodiments may also include one or more enhancers. Embodiments of the method also may be combined. For example, a method using an IHC detection scheme may be combined with an ISH detection scheme. Exemplary embodiments of the disclosed method may be used for determining cell clonality (e.g., a cell expresses either one of two biomarkers, but not both), predicting response of cancer patients to cancer therapy (e.g., detecting predictive biomarkers to determine whether a particular patient will respond to treatment), simultaneous analysis of biomarker expression and internal control gene expression to monitor assay performance and sample integrity, and combinations thereof.

Methods may be used on a biological sample having a solid phase, such as protein components of cells or cellular structures that are immobilized on a substrate (e.g., a microscope slide). In illustrative embodiments, the sample is a tissue or cytology sample, such as a formalin-fixed paraffin embedded sample, mounted on a glass microscope slide. In one embodiment, the method is particularly for an automated slide staining instrument.

A person of ordinary skill in the art will appreciate that numerous types of targets may be detected using the disclosed method. In certain disclosed embodiments, the target may be a particular nucleic acid sequence, a protein, or combinations thereof. For example, the target may be a particular sequence of RNA (e.g., mRNA, microRNA, and siRNA), DNA, and combinations thereof. The sample may be suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc. Samples can include multiple targets that can be specifically bound by one or more detection probes. Throughout this disclosure when reference is made to a target protein, it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

In some embodiments, the disclosed method may be used to detect microRNA (miRNA or miR). MicroRNAs are small, non-coding RNAs that negatively regulate gene expression, such as by translation repression. For example, miR-205 regulates epithelial to mesenchymal transition (EMT), a process that facilitates tissue remodeling during embryonic development. However, EMT also is an early step in tumor metastasis. Down-regulation of microRNAs, such as miR-205, may be an important step in tumor progression. For instance, expression of miR-205 is down-regulated or lost in some breast cancers. MiR-205 also can be used to stratify squamous cell and non-small cell lung carcinomas (*J. Clin Oncol.*, 2009, 27(12):2030-7). Other microRNAs have been found to modulate angiogenic signaling cascades. Down-regulation of miR-126, for instance, may exacerbate cancer progression through angiogenesis and increased inflammation. Thus, microRNA expression levels may be indicative of a disease state. For microRNA within the scope of the present disclosure, reference is made to PCT Application No. PCT/EP2012/073984, which is hereby incorporated by reference in its entirety.

In a particular disclosed embodiment, the disclosed method may be used to analyze clinical breast cancer FFPE tissue blocks that have been characterized for HER2 gene copy number and Her2 protein expression using INFORM HER2 Dual ISH and IHC assays (Ventana Medical Systems, Inc., "VMSI"), respectively. HER2 mRNA expression levels relative to ACTB (β-actin) can be determined using qPCR according to known methods. Results of the gene copy, protein expression, and qPCR analyses can be compared to results obtained through mRNA-ISH detection of HER2 and ACTB mRNA using the method disclosed herein to analyze FFPE samples. Further results from this method are discussed subsequently herein.

In another embodiment, the disclosed method may be used to identify monoclonal proliferation of certain types of cells. Cancer results from uncontrolled growth of a cell population; this population may arise from a single mutant parent cell and, therefore, comprise a clonal population. An example of cancer derived from a clonal population is B-cell non-Hodgkin lymphomas (B-NHL) which arise from monoclonal proliferation of B cells. Clonal expansion of a specific B cell population can be detected by sole expression of either KAPPA or LAMBDA light chain mRNA and protein as part of their B cell receptor antibody. Accordingly, one embodiment of the method disclosed herein concerns identifying monoclonal proliferation of B cells using chromogenic dual staining of KAPPA and LAMBDA mRNA.

Uniform expression of either light chain by malignant B cells enables differentiation of monoclonal B cell lymphomas from polyclonal KAPPA and LAMBDA light chain expressing B cell populations that result during the normal immune response. Determining light chain mRNA expression patterns is complicated by the copy number range of light chain mRNA and antibody protein expressed by B cell neoplasms derived from a variety of B cell stages (naïve and memory cells: 10-100 copies per cell; plasma cells: ~100 thousand copies per cell).

Methods

In illustrative embodiments, a method of detecting a target in a biological sample includes contacting the biological sample with a detection probe, contacting the biological sample with a labeling conjugate, and contacting the biological sample with a signaling conjugate FIG. 1 is a flowchart providing the steps of one exemplary embodiment of a method according to the present disclosure. In particular, the method includes a step 1 of contacting the sample with a detection probe(s). The step can include either a single detection probe or a plurality of detection probes specific to a plurality of different targets. A subsequent step 2 includes contacting the sample with a labeling conjugate. A further subsequent step 7 includes contacting the sample with a signaling conjugate. Dashed lines to step 3, contacting sample with an amplifying conjugate, and step 5, contacting sample with a secondary labeling conjugate, represent that these steps are optional. Dashed lines to step 10 of contacting sample with an enzyme inhibitor indicates that an optional loop can be used to detect multiple targets according to a multiplexed approach. In particular disclosed embodiments, one or more steps may be used wherein an enzyme inhibitor is added to the biological sample. For example, in embodiments wherein two or more signaling conjugates are added to the sample, an enzyme inhibitor (e.g., a peroxidase inhibitor) can be added in order to prevent any enzymatic activity after one signaling conjugate has been covalently deposited and before a second, different signaling conjugate is added.

In illustrative embodiments, detecting targets within the sample includes contacting the biological sample with a first amplifying conjugate that associates with the first labeling conjugate. For example, the amplifying conjugate may be covalently deposited proximally to or directly on the first labeling conjugate. The first amplifying conjugate may be followed by contacting the biological sample with a secondary labeling conjugate. Illustratively, the amplification of signal using amplifying conjugates enhances the deposition of signaling conjugate. The enhanced deposition of signaling conjugate enables easier visual identification of the chromogenic signal, that is, the amplification makes the color darker and easier to see. For low expressing targets, this amplification may result in the signal becoming sufficiently dark to be visible, whereas without amplification, the target would not be apparent. In embodiments wherein an amplification step is used, the biological sample may first be contacted with the detection probe and labeling conjugate and then subsequently contacted with one or more amplifying conjugates. In particular disclosed embodiments, the amplifying conjugate comprises a latent reactive moiety coupled with a detectable label. For example, a tyramine moiety (or a derivative thereof) may be coupled with a hapten, directly or indirectly, such as with a linker. The amplifying conjugate may be covalently deposited by the enzyme of the enzyme conjugate, typically using conditions described herein or are known to a person of ordinary skill in the art that are suitable for allowing the enzyme to perform its desired function. The amplifying conjugate is then covalently deposited on or proximal to the target.

Conditions suitable for introducing the signaling conjugates with the biological sample are used, and typically include providing a reaction buffer or solution that comprises a peroxide (e.g., hydrogen peroxide), and has a salt concentration and pH suitable for allowing or facilitating the enzyme to perform its desired function. In particular disclosed embodiments, this step of the method is performed at temperatures ranging from about 35° C. to about 40° C. These conditions allow the enzyme and peroxide to react and promote radical formation on the latent reactive moiety of the signaling conjugate. The latent reactive moiety, and therefore the signaling conjugate as a whole, will deposit covalently on the biological sample, particularly at one or more tyrosine residues proximal to the immobilized enzyme conjugate, tyrosine residues of the enzyme portion of the enzyme conjugate, and/or tyrosine residues of the antibody portion of the enzyme conjugate. The biological sample is then illuminated with light and the target may be detected through absorbance of the light produced by the chromogenic moiety of the signaling conjugate.

Depending on the level of multiplexing, the optional loop can be repeated one, two, three, four, five, six, seven, eight, or more times depending on the number of targets that are to be detected in the sample. During subsequent detection steps, the labeling conjugate can be the same or different depending on the blocking reagents used. An example of different labeling conjugates would be a first enzyme-anti-hapten antibody conjugate and a second enzyme-anti-hapten antibody conjugate, wherein the first anti-hapten antibody and the second anti-hapten antibody are specific to different haptens. According to another example, the difference could involve different anti-species antibodies, wherein the targets were detected using primary antibodies derived from different species. During subsequent detections, the signaling conjugate used for each target would typically be different. For example, the different targets could be detected as different colors.

While step 1 of contacting the sample with detection probe(s) is shown in FIG. 1 to be the simultaneous detection of multiple targets during one step, multiplexing may also be performed sequentially. A sequential method would include adding a first detection probe followed by carrying out the various subsequent method steps (i.e., steps 2, 7, optionally 3, and 5). A second detection probe may then be added after the first signaling conjugate has been covalently deposited on or proximal to the first target, thereby providing the ability to detect a second target. This process may then be iteratively repeated using a different signaling conjugate comprising a chromophore moiety that differs from the others deposited.

The method also comprises a step 9 of illuminating sample with light and a detecting target(s) step 11. The signal produced by the signaling conjugate is detected, thereby providing the ability to detect a particular target. In particular disclosed embodiments, the signal produced by the signaling conjugate may be fluorescent, chromogenic, or combinations thereof. Exemplary embodiments concern detecting a chromogenic signal. The signal may be detected using suitable methods known to those of ordinary skill in the art, such as chromogenic detection methods, fluorogenic detection methods, and combinations thereof. For example, the signal may be detected using bright-field detection techniques or dark-field detection techniques.

Figure 2A:
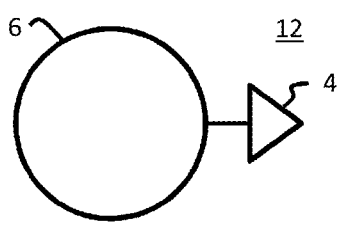
FIG. 2(A) illustrates a signaling conjugate comprising a latent reactive moiety and a chromophore moiety.
Figure 2B:
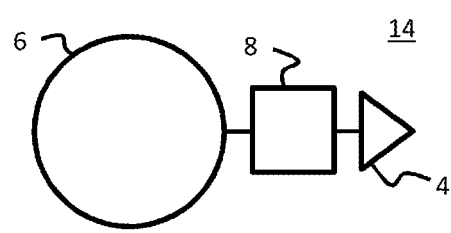
FIG. 2(B) illustrates an alternative signaling conjugate further comprising a linker.

FIGS. 2(A-B) are schematic diagrams of two embodiments of signaling conjugates. FIG. 2(A) illustrates a signaling conjugate 12 comprising a latent reactive moiety 4 and a chromophore moiety 6. FIG. 2(B) illustrates an alternative signaling conjugate 14, comprising chromophore moiety 6, latent reactive moiety 4, and further comprising a linker 8.

FIGS. 3(A-F) are schematic diagrams illustrating an embodiment of a method for detecting a target 17 on a sample 16. FIG. 3(A) shows a detection probe 18, which is shown illustratively to be a nucleic acid molecule with a hapten 19, binding to target 17, which, in this case, would be a nucleic acid target. FIG. 3(B) shows a labeling conjugate 20 binding to detection probe 18. Labeling conjugate 20 is depicted as an anti-hapten antibody specific to hapten 19 conjugated to two enzymes, which are depicted as circles containing an "E." While illustrated as being a conjugate of one antibody and two enzyme molecules, the number of enzymes per antibody can be altered and optimized for particular applications by a person of ordinary skill in the art. In particular, the number of enzymes could be modified from about 1 to about 10, depending on various factors, including the size of the antibody and the size of the enzymes. FIG. 3(C) shows signaling conjugate 12 being enzymatically deposited onto sample 16. In particular, enzymes "E," part of labeling conjugate 20, catalyze conversion of the first latent reactive moiety of signaling conjugate 12 into a first reactive species 13. This catalysis is represented by a first large arrow 21 directing signaling conjugate 12 to enzymes "E" and a second large arrow 22 emanating from enzymes "E" to reactive species 13, which is made of chromophore moiety 6 and a reactive moiety, which is represented by the dot replacing the arrow as shown on signaling conjugate 6. Reactive species 13 covalently binds to the biological sample proximally to or directly on the first target, to form a covalently bound chromophore 15. FIG. 3(D) shows an alternative embodiment in which an antibody-based detection probe 28 is used to detect a protein target 27. FIG. 3(D) is included to show that the steps of detecting either nucleic acid target 17 and/or protein target 27 are analogous except that detection probe 28 is represented as an antibody as opposed a nucleic acid (e.g., detection probe 18). Detection probe 28 is shown as not being haptenated, implying that labeling conjugate 30 is an anti-species antibody conjugated to enzymes "E." However, in alternative embodiments, detection probe 28 could be haptenated and labeling conjugate 30 could include an anti-hapten antibody.

Figure 3A:
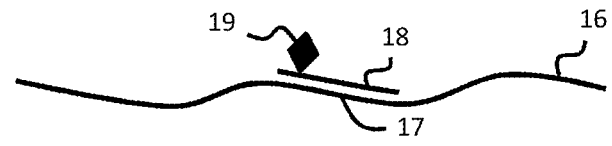
FIG. 3(A) shows a detection probe binding to the target.
Figure 3B:
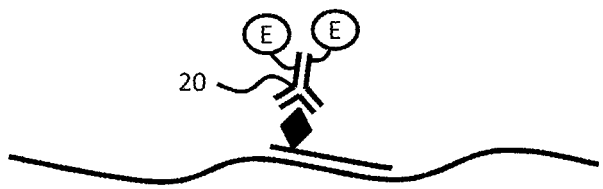
FIG. 3(B) shows a labeling conjugate binding to the detection probe.
Figure 3C:
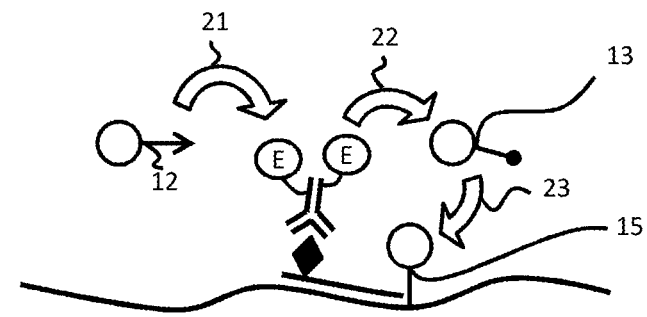
FIG. 3(C) shows a signaling conjugate being enzymatically deposited onto the sample.
Figure 3D:
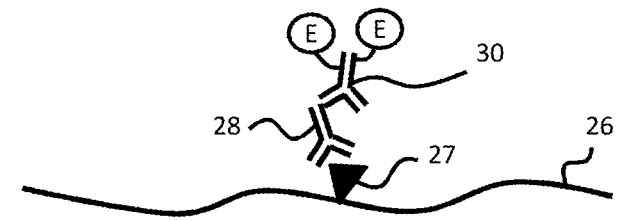
FIG. 3(D) shows an alternative embodiment in which an antibody-based detection probe is used to detect a different target.
Figure 3E:
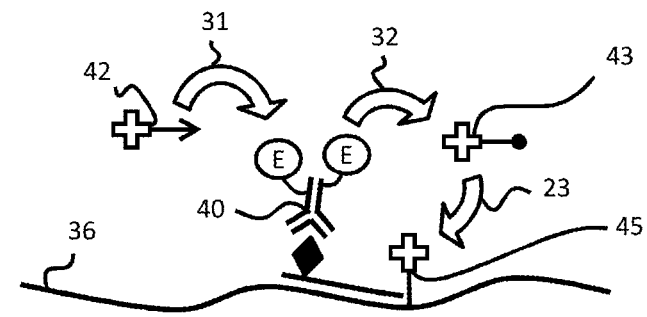
FIG. 3(E) shows an approach for detecting a target using an amplifying conjugate.
Figure 3F:
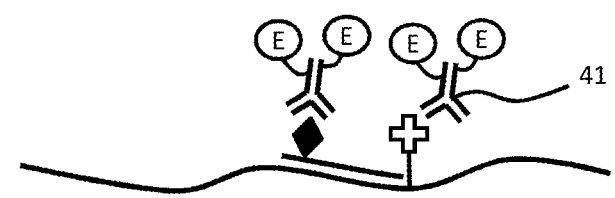
FIG. 3(F) shows that the amplifying conjugate was bound to the sample and was labeled with a secondary labeling conjugate.

FIG. 3(E) shows an approach to detecting the target that uses an amplifying conjugate 42. In particular, amplifying conjugate 42 is enzymatically deposited onto a sample 36. In particular, enzymes "E," part of labeling conjugate 40, catalyze conversion of the first latent reactive moiety of amplifying conjugate 42 into a first reactive species 43. This catalysis is represented by a first large arrow 31 directing amplifying conjugate 42 to enzymes "E" and a second large arrow 32 emanating from enzymes "E" to reactive species 43, which is made of a hapten (shown as a cross) and a reactive moiety, which is represented by the dot replacing the arrow as shown on amplifying conjugate 42. Reactive species 43 covalently binds to the biological sample proximally to or directly on the first target, to form a covalently bound hapten 45. The scheme depicted in FIG. 3(E) is shown here to make apparent the similarities between the scheme of FIG. 3(E) and the scheme of FIG. 3(C). In particular, the schemes are nearly identical except for the substitution of the chromophore moiety of signaling conjugate 12 for the hapten of amplifying conjugate 42. FIG. 3(F) shows that the amplifying conjugate bound to the sample (covalently bound hapten 45 as seen in FIG. 3(E)) can be labeled with a secondary labeling conjugate 41. While not shown, the scheme shown in FIG. 3(C) can then be used to form a covalently bound chromophore, as deposition of amplifying conjugate 42 onto the sample provides a larger number of enzyme molecules (i.e., enzymes from labeling conjugate 40 and secondary labeling conjugate 41 are shown proximally to the target in FIG. 3(F)).

Figure 4A:
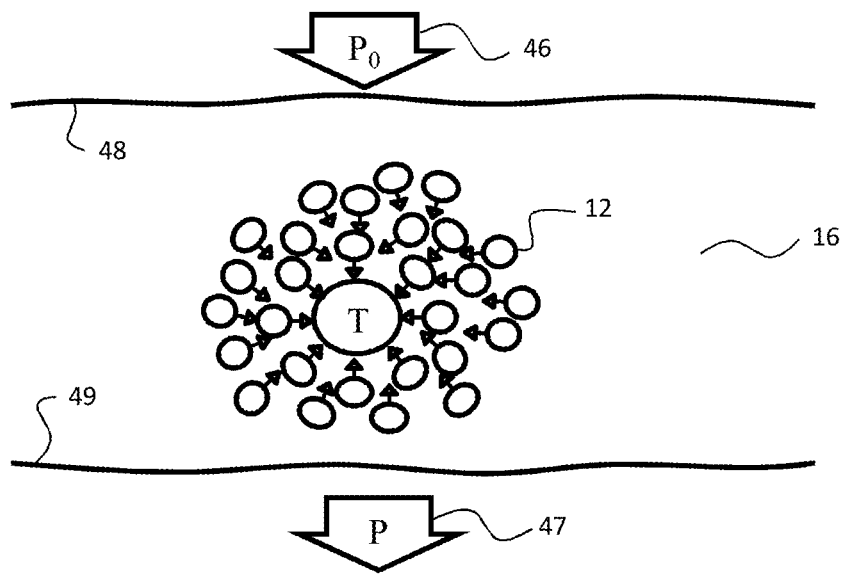
FIGS. 4(A-B) are schematic diagrams illustrating (A) a cross-sectional depiction of distribution of labeling conjugates proximally to target (T); and (B) a graph depicting the relationship between power of incident radiation ($P_0$) across the sample shown in (A) and power of transmitted radiation (P) through the sample, the y-axis representing radiation power and the x-axis representing linear distance across the sample.
Figure 4B:
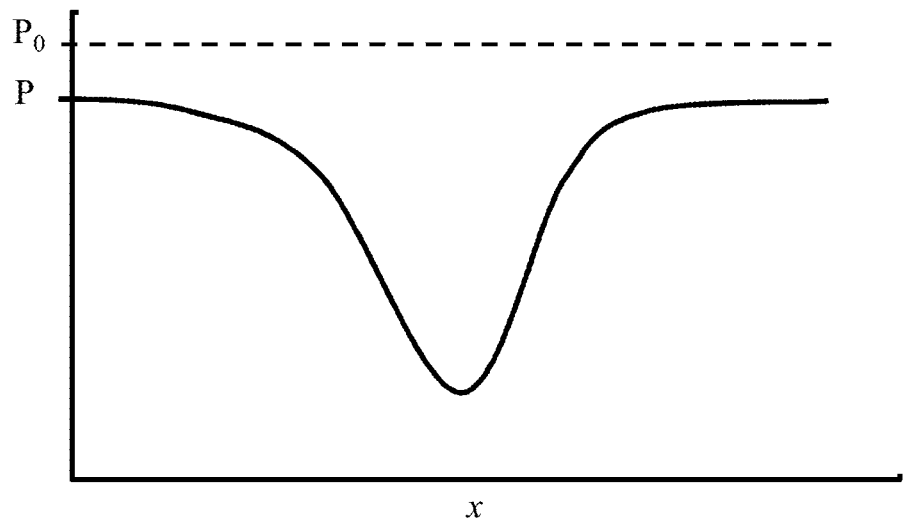

In particular disclosed embodiments, the signaling conjugate is detected using bright-field detection methods. An overview of this process is illustrated in FIGS. 4(A-B). FIG. 4(A) is a schematic of a cross-sectional view of sample 16 including an upper surface 48 and a lower surface 49 in which a plurality of the signaling conjugates 12 are located proximally to a target (T); the sample is shown having a first arrow 46 representing incident radiation directed towards upper surface 48 and a second arrow 47 representing transmitted radiation emanating from lower surface 49. FIG. 4(B) is a graph depicting the relationship between power of incident radiation ($P_O$) across sample 16 shown in FIG. 4(A) and power of transmitted radiation (P) through the sample, the y-axis being radiation power and the x-axis being linear distance across the sample. FIGS. 4(A-B) portray how a target could be visualized using signaling conjugate 12. Equation 1 provides the mathematical relationship between the power of the incident and transmitted radiation.

The disclosed method steps may be carried out in any suitable order, and are not limited to those described herein. In particular disclosed embodiments, the method may comprise steps wherein the labeling conjugates are added to the biological sample, followed by the signaling conjugate. In other disclosed embodiments, the method may comprise steps wherein the labeling conjugates are added to the biological sample, followed by an amplifying conjugate, an additional enzyme conjugate, and the signaling conjugate. The conjugates disclosed herein may be added simultaneously, or sequentially. The conjugates may be added in separate solutions or as compositions comprising two or more conjugates. Also, each class of conjugates used in the disclosed method may comprise the same or different conjugate components. For example, when multiple signaling conjugates are added to the sample, the conjugates may comprise the same or different chromogenic moieties and/or latent reactive moieties. Solely by way of example, one signaling conjugate may comprise a coumarin chromophore coupled to a tyramine moiety and another signaling conjugate may comprise a rhodamine chromophore coupled to a tyramine derivative moiety. The number of signaling conjugates suitable for use in the disclosed multiplexing assay may range from one to at least six, or more typically from two to five. In particular disclosed embodiments, the method is used to detect from three to five different targets using from three to five different signaling conjugates. Multiple targets may be detected in a single assay using the method disclosed herein. In another embodiment, any one or more of the steps disclosed herein for the method are performed by an automated slide staining instrument.

Chromogenic vs. Fluorescence

Figure 5A:
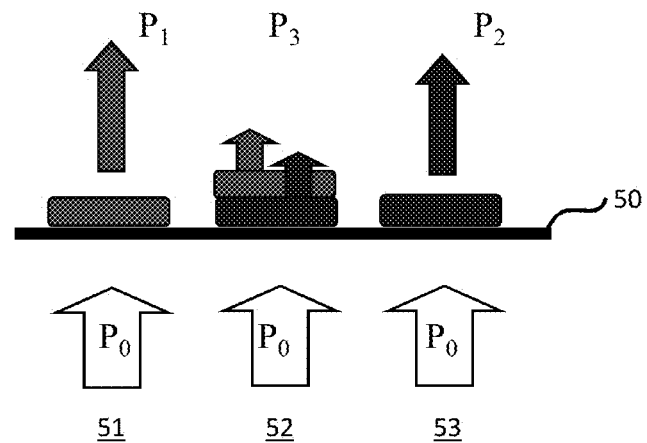
FIG. 5(A) illustrates detection of a chromogen wherein the transmitted light is detected.
Figure 5B:
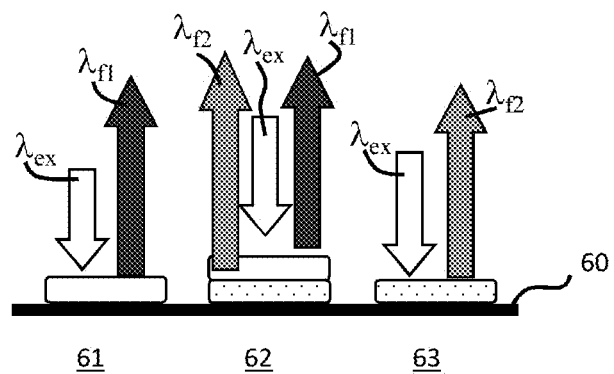
FIG. 5(B) illustrates the detection of a fluorophore wherein the emitted light is detected.

Historically, break-apart analysis has been done using FISH; however, the present disclosure provides a three-color, break-apart assay using chromogenic ISH. The differences between chromogenic detection and fluorescence detection are pictorially illustrated in FIGS. 5(A) and 5(B). FIG. 5(A) shows a red chromogen example 51, a blue chromogen example 53, and a red and blue multiplexed chromogen example 52. When chromogens are exposed to light (i.e., exposed to light having an incident power of $P_0$), which typically is white light, the chromogens absorb various wavelengths. The transmitted light will have a particular power (FIG. 5(A), indicated as $P_1$, $P_2$, and $P_3$) depending on the absorbance of the chromogen and the amount of chromogen present. The better detection event results in more chromogen being deposited, which absorbs more light and makes the observed signal smaller. Even for colored chromogens, a reduction of the transmitted light will eventually cause the chromogen to appear black as no light is transmitted. Multiplexing exacerbates this effect, as shown in red and blue multiplexed chromogen example 52. When a traditional red chromogen and a blue chromogen overlap in space, the absorbance is broad and the detection event appears blackish and dark, as illustrated by the $P_3$ signal being smaller than $P_1$ and $P_2$. Essentially, chromogenic detection with overlapping signals will result in a subtractive effect. This is in contrast to fluorescence which is illustrated in FIG. 5(B). With reference to FIG. 5(B), a purple fluor example 61, a green fluor example 63, and a purple and green multiplexed fluor example 62 are shown. The excitation light (shown as $\lambda_{ex}$ in the figure) can be the same across the three examples and example 61 exhibits $\lambda_{f1}$ (purple fluorescence), example 63 exhibits $\lambda_{f2}$ (green fluorescence), and example 62 exhibits $\lambda_{f1}$ (purple fluorescence) and $\lambda_{f2}$ (green fluorescence). As more fluor is deposited on the sample a stronger fluorescence signal is generated. Similarly, in a multiplexed scenario, there is an additive affect for the fluorophores, whereas a subtractive effect occurs with the chromophores. This subtractive versus additive feature significantly compounds the difficulty of multiplexing using chromogens. As such, multiplexing with traditional chromogens has not been broadly accepted. The current disclosure provides signaling conjugates with narrow wavelength absorbance bands, which enable combinations of colors heretofore not possible. As such, the present disclosure provides unprecedented chromogenic multiplexing despite the inherent disadvantages that chromogenic multiplexing has when compared to fluorescent multiplexing.

Detecting & Illuminating

The signaling conjugate is configured to provide a variety of characteristics that facilitate providing a detectable signal. In particular disclosed embodiments, the signaling conjugate comprises an appropriate chromophore moiety to provide a bright-field signal. For example, the chromophore disclosed herein may be selected to produce an optical signal suitable for detecting the target disclosed herein. In particular disclosed embodiments, the chromophore has optical properties, such as those discussed below, that allow the signaling conjugate to be configured to provide the desired signal.

Figure 6A:
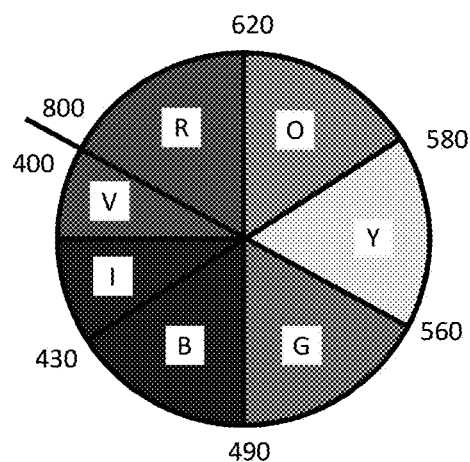
FIG. 6(A) is a color wheel depicting the relationship between an observed color and FIG. 6(B) is an image of absorbed radiation for the signaling conjugate.
Figure 6B:
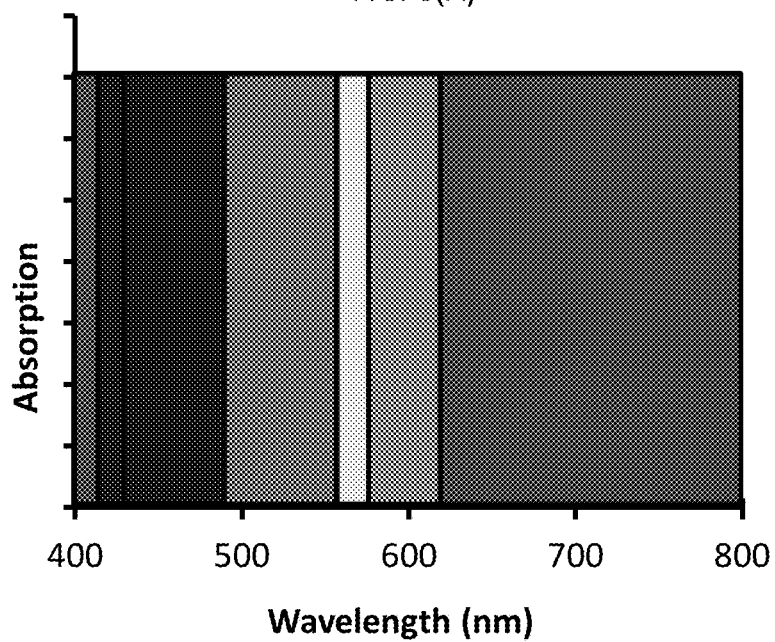

When light (i.e., visible electromagnetic radiation) passes through or is reflected by a colored substance, a characteristic portion of the spectral wavelength distribution is absorbed. The absorption of this characteristic portion imparts on the object a complementary color corresponding to the remaining light. FIGS. 6(A) and 6(B) show a color wheel (FIG. 6(A)) that illustrates the relationship between an observed color and absorbed radiation. The color wheel includes a number of pie pieces representing colors (R) Red, (O) Orange, (Y) Yellow, (G) Green, (B) Blue, (I) Indigo, and (V) Violet. Each color is shown as a separate pie piece from the next color with a series of lines terminating at numbers outside the wheel. These numbers designate the wavelength of light in nanometers (nm) of those wavelengths traditionally considered to be the transition points between colors. FIG. 6(B) shows the same distribution of colors on a linear graph having the wavelength of light on the x-axis. That is, the region from 620 to 800 nm is shown colored red as those wavelengths are "red" light wavelengths. Typically, colors are perceived preferentially and some colors are perceived only for a very narrow span of wavelengths. For example, a laser having emission anywhere from 490 nm to 560 nm would be perceived as green (a 70 nm span). To be perceived as orange, the laser would have to emit light in the range of 580 nm and 620 nm (40 nm). The graph is provided for representation only, and a person of ordinary skill in the art appreciates that the electromagnetic spectrum is continuous in nature and not discrete as shown. However, the color classifications delineated herein facilitate an understanding of the technology, as claimed herein.

As described herein, when a substance absorbs a particular wavelength, the substance appears to be the complementary color, that color corresponding to the remaining light. The color wheel of FIG. 6(A) shows complementary colors diametrically opposed to each other. According to the color wheel, absorption of 420-430 nm light imparts a yellow color to the substance (425 nm is opposite to that portion of the wheel that is yellow). Similarly, absorption of light in the range of 500-520 nm imparts a red color to the substance since the red pie area is opposite the numerical range of 500-520 nm. Green is unique in that absorption close to 400 nm as well as absorption near 800 nm can impart a green color to the substance.

The concept that the absorption of light at wavelengths between 420-430 nm results in the substance appearing yellow is an over-simplification of many of the absorption phenomena described herein. In particular, the absorption spectral profile has a strong influence on the observed color. For example, a substance that is black absorbs strongly throughout the range of 420-430 nm, yet the black substance does not appear yellow. In this case, the black absorber will absorb light across the entire visible spectrum, including 420-430 nm. Thus, while absorption of light at a particular wavelength is important, absorption characteristics across the visible spectra (i.e., spectral absorption) also are important.

Figure 7A:
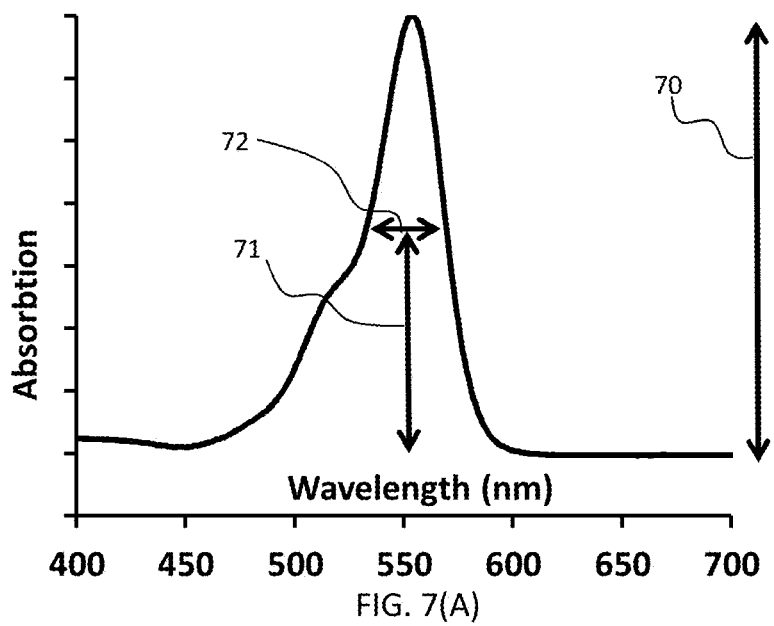
FIG. 7(A) is a graph illustrating the absorption spectrum of a 5-TAMRA-tyramide conjugate.
Figure 7B:
FIG. 7(B) is a photomicrograph illustrating a biological sample having targets detected by this particular signaling conjugate.

Spectral absorption can be characterized according to several measurable parameters. The wavelength at which the maximum fraction of light is absorbed by a substance is referred to as $\lambda_{max}$. Because this wavelength is absorbed to the greatest extent, it is typically referred to as the absorbance wavelength. FIG. 7(A) is an absorption spectrum of a particular signaling conjugate, and FIG. 7(B) illustrates a photomicrograph of a protein stained using the signaling conjugate producing the absorption spectrum of FIG. 7(A). FIG. 7(A) includes a first arrow (70) illustrating the magnitude of the maximum absorbance. A second arrow (71) shows the magnitude of half of the maximum. A third arrow (72) shows the width of the peak at half of the maximum absorbance. For this exemplary signaling conjugate, $\lambda_{max}$ is 552 nm and the full width of the peak at the half maximum absorbance (e.g., FWHM) is approximately 40 nm. While $\lambda_{max}$ designates the wavelength of maximum absorption, the FWHM designates the breadth of the spectral absorbance. Both factors are important in describing the chromophore's color because broad absorption spectra do not appear to have a color as would be expected from their $\lambda_{max}$. Rather, they appear to be brown, black, or gray. Referring to FIG. 7(B), deposition of the signaling conjugate is clearly evident in those locations that would be expected for positive staining (HER2 (4B5) IHC in Calu-3 xenografts). Referring back to the color wheel (FIG. 6(A)), a $\lambda_{max}$ of 552 nm should correspond to a complementary color of red or red-violet. This matches the color observed in the tissue sample shown in FIG. 7(B) (note that the sample further includes hematoxylin nuclear counterstaining that is blue). Because the counterstain is confined to the nucleus, it does not appear to interfere or substantially affect the cell-membrane based HER2 staining.

Preferred chromophores have strong absorbance characteristics. In some embodiments, the chromophores are non-fluorescent or weakly fluorescent. By virtue of its absorbance characteristics, a chromophore is a species capable of absorbing visible light. A preferred chromophore is capable of absorbing a sufficient quantity of visible light with sufficient wavelength specificity so that the chromophore can be visualized using bright-field illumination. In another embodiment, the chromophore has an average molar absorptivity of greater than about 5,000 $M^{-1}$ $cm^{-1}$ to about 90,000 $M^{-1}$ $cm^{-1}$. For example, the average molar absorptivity may be greater than about 5,000 $M^{-1}$ $cm^{-1}$, greater than about 10,000 $M^{-1}$ $cm^{-1}$, greater than about 20,000 $M^{-1}$ $cm^{-1}$, greater than about 40,000 $M^{-1}$ $cm^{-1}$, or greater than about 80,000 $M^{-1}$ $cm^{-1}$. Strong absorbance characteristics are preferred to increase the signal, or color, provided by the chromophore.

The deposition of signaling conjugates in the vicinity of the target creates absorption of the incident light. Because the absorption occurs non-uniformly across the sample, the location of the target, within the sample, can be identified.

Certain aspects, or all, of the disclosed embodiments can be automated, and facilitated by computer analysis and/or image analysis system. In some applications, precise color ratios are measured. In some embodiments, light microscopy is utilized for image analysis. Certain disclosed embodiments involve acquiring digital images, which can be done by coupling a digital camera to a microscope. Digital images obtained of stained samples are analyzed using image analysis software. Color can be measured in several different ways. For example, color can be measured as red, blue, and green values; hue, saturation, and intensity values; and/or by measuring a specific wavelength or range of wavelengths using a spectral imaging camera.

Illustrative embodiments involve using bright-field imaging with the signaling conjugates. White light in the visible spectrum is transmitted through the chromophore moiety. The chromophore absorbs light of certain wavelengths and transmits other wavelengths. This changes the light from white to colored depending on the specific wavelengths of light transmitted.

The narrow spectral absorbances enable chromogenic multiplexing at a level beyond the capability of traditional chromogens. For example, traditional chromogens are somewhat routinely duplexed (e.g., Fast Red and Fast Blue, Fast Red and Black (silver), Fast Red and DAB). However, triplexed or three-color applications are atypical. In illustrative embodiments, the method includes detecting from two to about six different targets, such as three to six, or three to five, using different signaling conjugates or combinations thereof. In one embodiment, illuminating the biological sample with light comprises illuminating the biological sample with a spectrally narrow light source, the spectrally narrow light source having a spectral emission with a second full-width half-max (FWHM) of between about 30 nm and about 250 nm, between about 30 nm and about 150 nm, between about 30 nm and about 100 nm, or between about 20 run and about 60 nm. In another embodiment, illuminating the biological sample with light includes illuminating the biological sample with an LED light source. In another embodiment, illuminating the biological sample with light includes illuminating the biological sample with a filtered light source.

The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

In one embodiment, the signaling conjugate is covalently deposited proximally to the target at a concentration suitable for producing a detectable signal, such as at a concentration greater than about $1\times10^{11}$ molecules per $cm^2 \cdot \mu m$ to at least about $1\times10^{16}$ molecules per $cm^2 \cdot \mu m$ of the biological sample. One of ordinary skill in the art could calculate the number of molecules per $cm^2 \cdot \mu m$ of the biological sample by using Equation 1 and absorbance measurements across the sample, taking care to subtract the absorbance corresponding to the sample. In one embodiment of the disclosed method, such as a multiplexing method, detecting one signal includes detecting an absorbance of 5% or more of incident light compared to a background, and detecting a different, separate signal includes detecting an absorbance of 5% or more of incident light compared to the background. In another embodiment, detecting one signal includes detecting an absorbance of 20% or more of incident light compared to a background, and detecting a different, separate signal includes detecting an absorbance of 20% or more of incident light compared to the background.

In one embodiment, the first target and the second target are genetic nucleic acids. Detecting the first target through absorbance of the light by the first signaling conjugate includes detecting a first colored signal selected from red, orange, yellow, green, indigo, or violet. The first colored signal is associated with spectral absorbance associated with the first chromogenic moiety of the first signaling conjugate. Detecting the second target through absorbance of the light by the second signaling conjugate includes detecting a second colored signal selected from red, orange, yellow, green, indigo, or violet. The second colored signal is associated with spectral absorbance associated with the second chromogenic moiety of the second signaling conjugate. An overlap in proximity through absorbance of the light by the first signaling conjugate overlapping in proximity with the second signaling conjugate so that a third colored signal can be detected that is associated with overlapping spectral absorbance of the first spectral absorbance and the second spectral absorbance. According to one example, this third colored signals a normal genetic arrangement and the first and second colors signal a genetic rearrangement or translocation.

ISH Three-Color Break Apart Probe

Figure 8A:
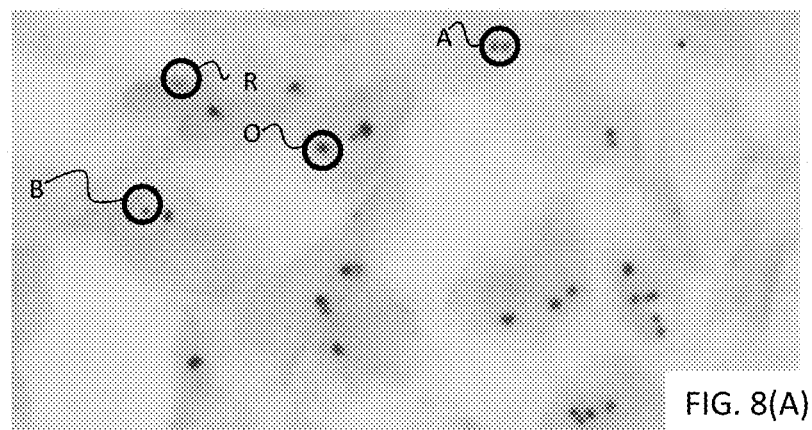
FIG. 8(A) is a photomicrograph of a dual stain of two gene probes on a lung tissue section testing for ALK rearrangements associated with non-small cell lung cancer.
Figure 8B:
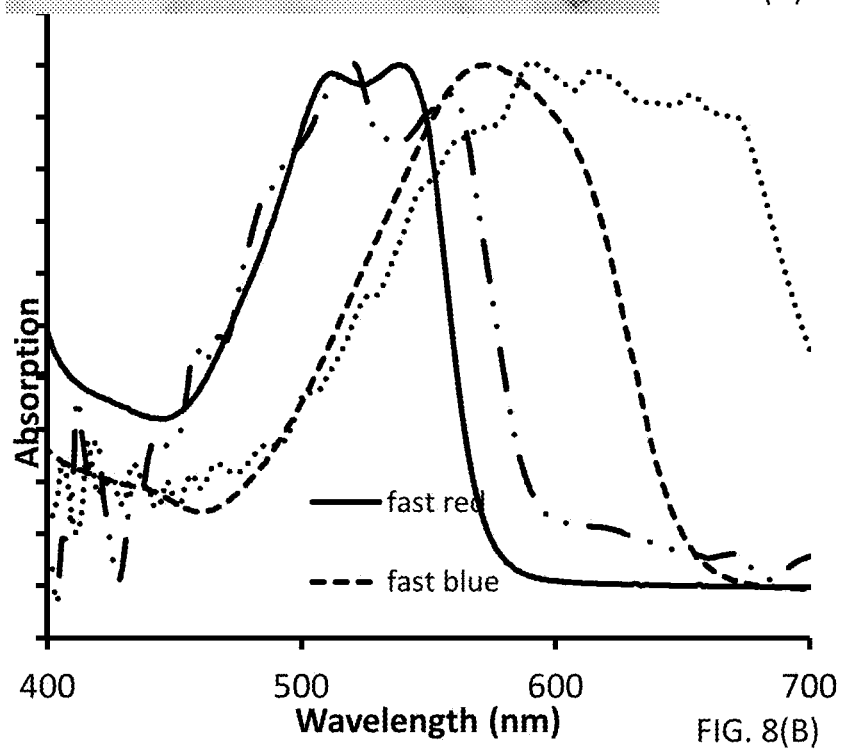
FIG. 8(B) is a UV-Vis spectra of fast red and fast blue in ethyl acetate solutions as well as traces obtained from tissue samples.
Figure 9A:
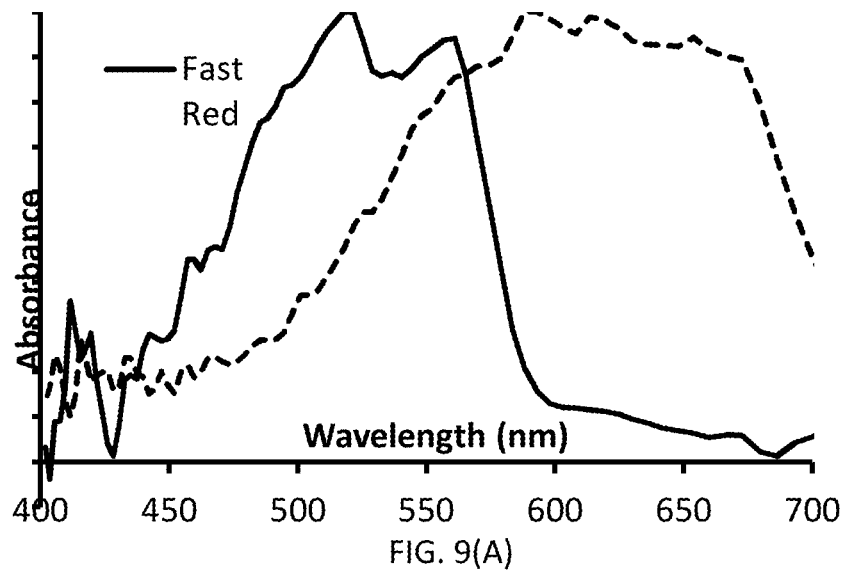
Figure 9B:
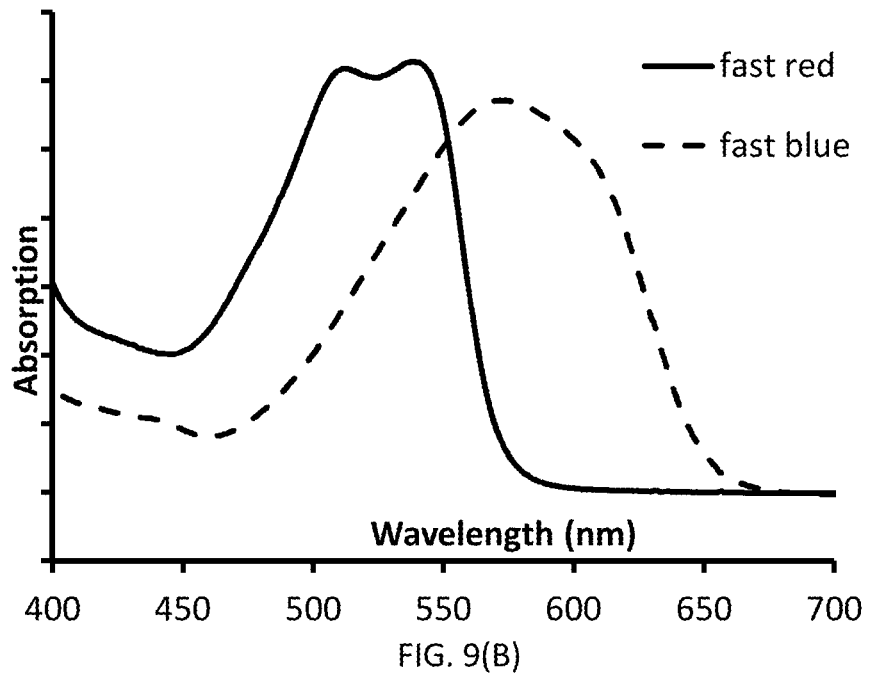
FIG. 9(B) illustrates traces obtained from ethyl acetate solutions of Fast Red and Fast Blue.

While providing a range of new colors for the recognition of targets within biological samples is useful alone, the presently disclosed signaling conjugates are particularly useful in multiplexed assays, as well as assays using translocation probes. FIG. 8(A) is a photomicrograph of a dual stain of two gene probes on section of lung tissue testing for ALK rearrangements associated with non-small cell lung cancer. FIG. 8(B) illustrates UV-Vis spectra of fast red and fast blue in ethyl acetate solutions. The 3' probe was detected using fast red and the 5' probe was detected using fast blue. FIGS. 9(A) and 9(B) illustrate the traces of FIG. 8(B) separately. FIG. 8(B) shows that fast red and fast blue have broad and well-defined spectral absorption characteristics. Fast red shows strong absorption between about 475 nm and about 560 nm. Comparing this range to the color wheel, the expected color corresponding to the spectral absorption characteristic would be either red or orange. The range of absorption is so large it essentially covers all of those wavelengths one would expect to result in a red or an orange color. Fast blue exhibits strong absorption between about 525 nm and about 625 nm, a range even broader than fast red. Again, referring to the color wheel in FIG. 6(A), the absorption from 525-625 nm covers nearly half of the color wheel with blue, indigo, and violet being complementary.

Referring now to FIG. 8(A), a fast red spot is highlighted by the circle (R), a fast blue spot is highlighted by the circle (B), a set of spots, one fast red spot and one fast blue spot, are labeled as adjacent by the circle (A), and a fast red spot and a fast blue spot overlapping each other is labeled by the circle (O). As predicted, the fast red spot (A) is red, and the fast blue spot (B) appears a dark bluish color one would expect from the mixture of blue, indigo and violet. The adjacent spots within circle (A) can be clearly distinguished from each other as separate red and blue spots. However, the spot that includes an overlapping red and blue spot results in an ambiguous color. It appears somewhat bluish and has a red fringe on one side. The color of the spot is difficult to distinguish and difficult to characterize. For an overlapping spot, the absorption of the fast red and the fast blue would be additive and the spectral absorption profile would span from about 475 nm to about 625 and have $\lambda_{max}$ of around 550 nm. Referring again to the color wheel (FIG. 6(A)), this range of wavelengths covers nearly the entire wheel. Broad based absorption covering the entire spectra typically gives a black or brown appearance with a tint of those colors absorbed least, in this case indigo and violet. A pathologist considering the photomicrograph in FIG. 8(A) may have difficulty distinguishing between a blue to indigo spot (B) and the overlapping spot (O).

Figures 10A, 10B:
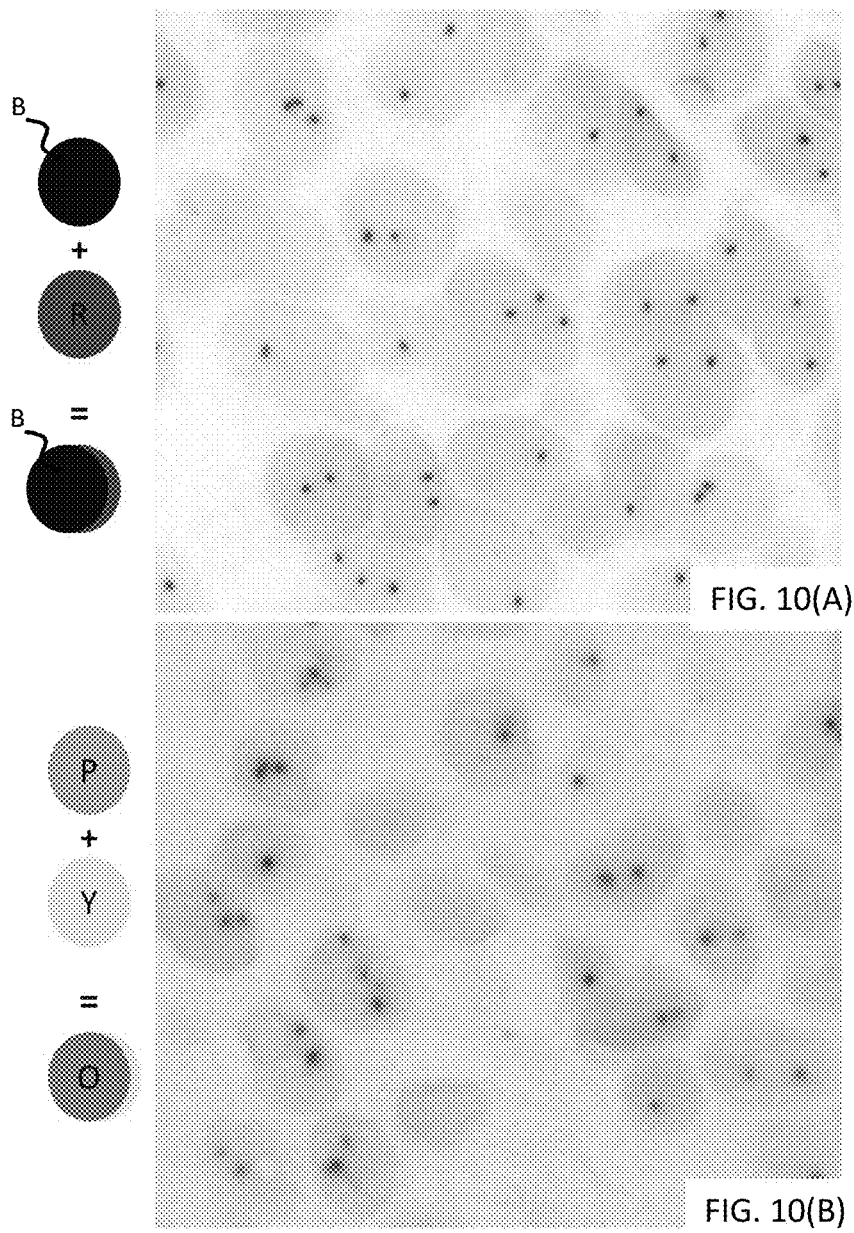
FIG. 10(A) shows a SISH/Red combined detection protocol.
FIG. 10(B) shows a purple and yellow signaling conjugate as described herein. The signal produced by combining these two chromogens is detected as a third, unique color.
Figure 11A:
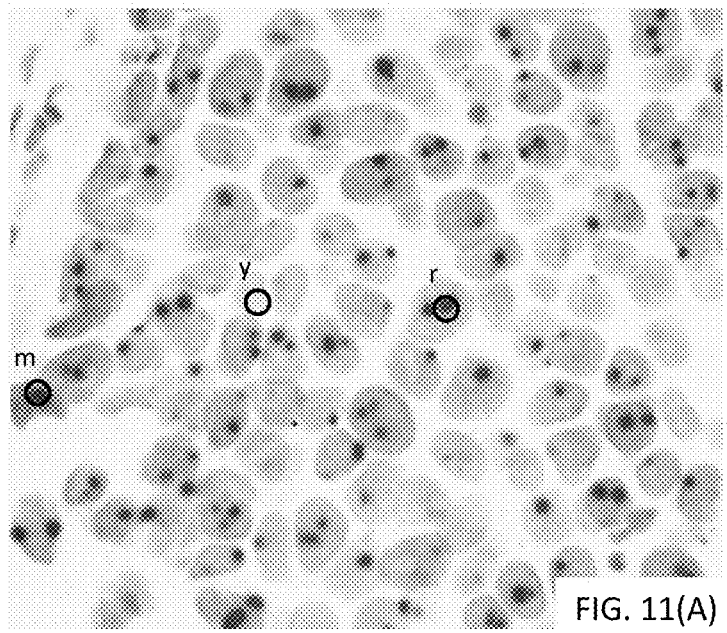
FIGS. 11(A-B) are photomicrographs showing two examples of depositing two colors proximally to create a visually distinct third color.
Figure 11B:
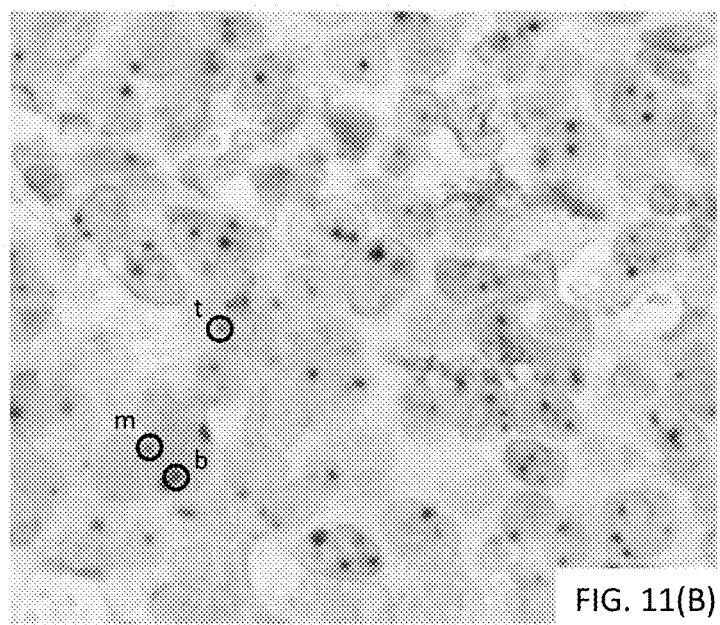

Accordingly, certain disclosed embodiments provide the ability to choose different signaling conjugates that address this issue. For example, different signaling conjugates can be purposefully selected and made to comprise chromogenic moieties that produce light at opposing ends of the UV-vis spectrum. FIGS. 10(A) and 10(B) illustrate how the disclosed signaling conjugates and method can be used for resolving the issue associated with probes comprising two different chromogenic moieties. With reference to FIG. 10(A), a chromogenic moiety capable of producing a black color ("B") is used in combination with a chromogenic moiety that produces a red color ("R"). When the two signaling conjugates overlap, it is unclear as two whether the observed black color ("B") is produced by the black chromogenic moiety or if it is produced by the overlap between the red and black chromogenic moieties. However, referring to FIG. 10(B), this problem can be solved by using two chromogenic moieties that, when combined, produce a third unique color. For example, a purple chromogenic moiety ("P") may be used in combination with a yellow chromogenic moiety ("Y"). The overlap between the two is readily observed, as an orange signal ("O") is produced. FIGS. 11(A-B) further show how two colors can be deposited proximally to create a visually distinct third color. In particular, FIG. 11(A) shows a yellow signal, shown with a letter "y", combined with magenta signal, shown with a letter "m", to create a vibrant cherry red color, shown with a letter "r". FIG. 11(B) shows a magenta signal, indicated by the letter "m," and a turquoise signal, indicated by the letter "t," combine to create a dark blue signal, shown with a letter "b".

Illumination

In particular disclosed embodiments, a traditional white source and filter system may be used, such as those typically used by persons of ordinary skill in the art. In other disclosed embodiments, an LED light source may be used in the detection step in order to generate narrower illumination light. Such light sources may be used in embodiments wherein one or more different signaling conjugates are used, particularly when three or more different conjugates are used.

The method disclosed herein provides improved detection in terms of the signal produced as well as the means by which the signal is detected. Traditional detection techniques typically comprise using narrow absorbing dyes with spectral filtering wherein the dye absorbs only a narrow range of light having a certain wavelength, and the filter passes only a small range of wavelengths. Accordingly, combining the filter with such absorbance produces a black spot in an otherwise bright-field, or other chromogens may have absorbances that are within the spectral absorbance ranges of the filter and therefore are not even apparent under bright-field detection. This type of detection technique typically is deconvulated into separate images or may further use an overlaid image having false coloring. Using embodiments of the method disclosed herein, bright-field detection may be used without the problems typically associated with this particular technique in analyzing chromogenic signals. The variety of signaling conjugates contemplated by the present disclosure provides the ability to analyze the biological sample in the bright-field and visually detect the color signal(s) emitted without further manipulation. Furthermore, the ability to use LED light sources with the disclosed method provides flexibility in the range of wavelength that can be absorbed by the disclosed signaling conjugate. In particular disclosed embodiments, the signaling conjugates can be visualized independently by illuminating the specimen with light of a wavelength where the chromogen absorbs, thus causing the chromogen to appear dark against a light background (light is absorbed by the chromogen, reducing the light intensity at that spot). In particular disclosed embodiments, illuminating the specimen with light that is not absorbed by the chromogen causes the chromogen to "disappear" because the intensity of the light is not altered (absorbed) as it passes through the chromogen spot. Solely by way of example, illuminating a biological sample slide with green light causes the rhodamine chromogens to appear dark, whereas the Cy5 chromogen disappears. Conversely, illuminating the slide with red light causes the Cy5 chromogen to appear dark and the rhodamine chromogens to disappear.

Slides stained using certain disclosed signaling conjugates were illuminated using a multi-LED illuminator that was adapted to Olympus BX-51 light microscope. Two LED illuminators were used: 1) a homebuilt 3-LED illuminator comprising a Lamina RGB light engine (EZ-43F0-0431) with 3 LEDdynamics BuckPlus current regulated drivers with potentiometers and switches to permit on off control and variation of the red, green, and blue LED intensities independently; and 2) a TOFRA, Inc. RGBA Computer-Controlled LED Illuminator for Upright Microscopes modified for manual LED switching. To visualize only the tyramide chromogens, illuminating the specimen with light of a wavelength where the chromogen absorbs causes the chromogen to appear dark against a light background (light is absorbed by the chromogen, reducing the light intensity at that spot). Illuminating the specimen with light that is not absorbed by the chromogen causes the chromogen to "disappear" because the intensity of the light is not altered (absorbed) as it passes through the chromogen spot.

Figure 12A:
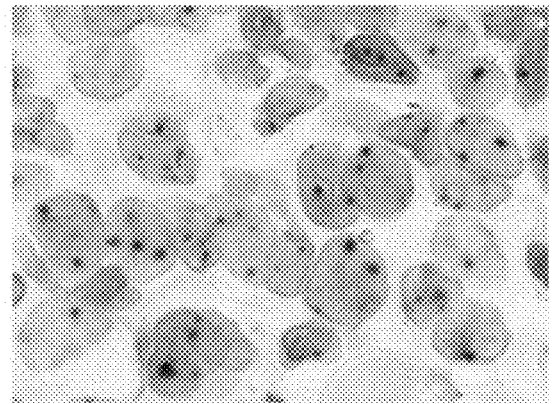
FIG. 12(A) shows white light illumination, FIG. 12 (B) shows green light illumination and FIG. 12 (C) shows red light illumination.
Figure 12B:
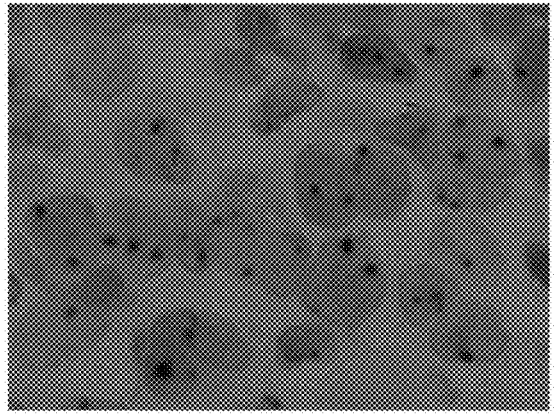
FIGS. 12(A-C) are photomicrographs showing the use of LED illumination to separate the signal from a chromogenic dual stain, where
Figure 12C:
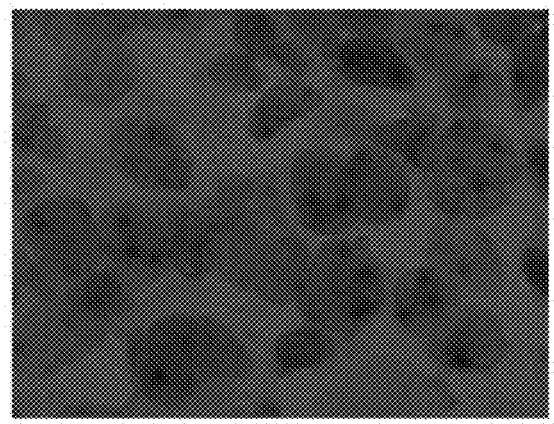

FIGS. 12(A-B) are photomicrographs of a sample that has been dual stained with a turquoise and magenta signaling conjugate under (A) white light illumination, (B) green light illumination, and (C) red light illumination. Illuminating the slide with green light causes the turquoise signaling conjugates to appear dark, whereas the magenta signaling conjugate disappears. Conversely, illuminating the slide with red light causes the magenta signaling conjugate to appear dark and the turquoise signaling conjugate to disappear. Overlap between the magenta and the turquoise signaling conjugates are dark in white light illumination, green light illumination, and red light illumination. One of the perceived benefits of fluorescence microscopy is the ability to use filters to switch between the individual probe signals. Using the signaling conjugates described herein, it is possible to enable switching using chromogenic compounds. Matching the LED emission wavelength with the absorbance wavelength of the tyramide dye causes the matched chromogen signal to "disappear." LED power sources can be easily added to a light microscope by replacing the condenser. The emission wavelength of the LED can be switched between colors by the user, with the push of a button.

Tyrosine Enhancement

Tyramide signal amplification and the signaling conjugates described herein react with tyrosine residues available from the sample and or the molecules/conjugates used to detect and label the targets. The amount of protein surrounding the biomarker to be detected is variable based on the natural variation between tissue samples. When detecting biomarkers present at high levels, or when detecting the co-localization of multiple biomarkers, the amount of protein to which the tyramide molecules can attach may be a limiting reactant in the deposition process. An insufficient amount of protein in the tissue can result in the diffusion of tyramide based detection, the potential to under-call the expression level of biomarkers, and the inability to detect co-localized biomarkers. One solution to these problems is to provide more protein binding sites (i.e., tyrosine) by coating the tissue with a proteinaceous solution and permanently cross-linking the protein to the tissue using formalin, or other fixatives.

The majority of work with TSA has been done in the context of fluorescent detection. Fluorescent TSA detection is accomplished by a single tyramide deposition of a fluorophore, and the deposition times are typically quite short because the sensitivity of the fluorescent detection is high, whereas the background associated with traditional TSA becomes problematic with longer deposition times. In contrast, chromogenic TSA detection may include multiple depositions of tyramide conjugates with extended deposition times. As such, the fluorescent TSA art does not suggest solutions to chromogenic TSA problems because the nature of the problem is so different. In particular, the saturation of a sample's tyrosine binding sites by tyramide reactive species is thought to be a unique problem particular to the detection chemistries described herein. Enhancements to TSA originating from the TSA fluorescence research typically addressed the diffusion of the reactive tyramide moieties and the lack of TSA signal. Solutions to these problems have been described in the art. For example, an increase in the viscosity of the reaction solution through the addition of soluble polymers was described for decreasing diffusion and HRP activity was enhanced through the addition of vanillin and/or iodophenol. These solutions were not sufficient to address some of the problems observed for the detection chemistries described herein.

Through various studies, it was discovered that the severity of the identified problem varies depending on the sample used. For example, it was found that breast cancer tissues and prostate cancer tissues included different levels of available tyramide binding sites. It is also known that there are differences in protein content in the cellular compartments (nucleus, cell membrane, cytoplasm, etc.) that are targeted in various IHC and/or ISH tests. Hence, in addition to being necessary for TSA co-localization, the proposed invention will normalize protein content (e.g., tyramide binding sites) and reduce variation between and across samples. In illustrative embodiments, the addition of a tyrosine enhancement agent may increase inter- and intra-sample reproducibility of assays described herein.

When using amplifying conjugates, as described herein, especially in conjunction with the signaling conjugates described herein, the amount of protein surrounding the target or targets may be insufficient. When detecting biomarkers present at high levels, or when detecting the co-localization of multiple biomarkers, the amount of protein in the sample to which the tyramide-based detection reagents can attach may be the limiting reagent. An insufficiency in tyramide binding sites can cause a reduced reaction rate, allow the tyramide reactive molecules to diffuse away from the target, and generally results in a weaker response due to lower quantities of the signaling conjugates reacting in the vicinity of the target. It was discovered that providing more binding sites to the sample enhanced the detection as described herein. One approach to enhancing the available binding sites was to introduce a protein solution to the sample. So that the protein remains through various washes and so that the protein does not diffuse during or after subsequent detection steps, the protein was cross-linked to the sample using a fixative (e.g., formalin).

In illustrative embodiments, an additional amount of a tyrosine-containing reagent, such as a protein, may be incubated with and fixed to the biological sample in order to provide additional binding sites for multiple signaling or amplifying conjugates, such as in multiplexing or amplification. For example, when a translocation probe is used, clearer three-color staining may be obtained by adding an additional amount of protein to the biological sample. Additionally, non-specific probe binding can be decreased using this additional step. Exemplary embodiments concern adding BSA to the biological sample, followed by fixing the protein using a cross-linking agent, such as a fixative (e.g., 10% NBF).

Figure 13A:
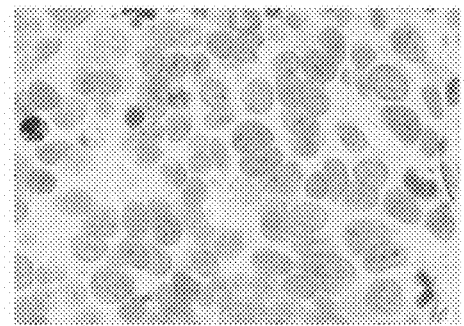
FIG. 13(A) shows a control slide to which no BSA-BF was added.
Figure 13B:
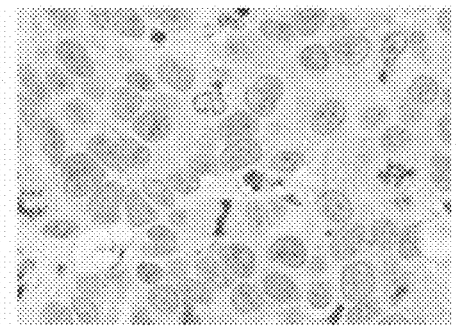
FIG. 13(B) shows a slide to which the BSA-BF had been attached to the sample.

To demonstrate the efficacy of the solution, it was first established that exogenous proteins can be fixed to a sample, (e.g., a histologically prepared paraffin-embedded tissue sample). To demonstrate that additional protein can be covalently attached to paraffin tissue sections, bovine serum albumin (BSA) was functionalized with a hapten (2,1,3-Benzoxadiaole-carbamide, "BF"). The BSA-BF was added to the tissue following a hybridization step where no probe was added, and all experiments were completed on a Benchmark XT automated slide stainer (Ventana Medical Systems, Tucson Ariz.). 10 µg of the BSA-BF conjugate was added to the slide and incubated for 16 minutes. BF-labeled BSA protein was then covalently fixed to the tissue by adding 100 µl of 4% paraformaldehyde, and incubating for 16 minutes. The presence of covalently attached BSA-BF was detected by adding an anti-BF monoclonal antibody that was functionalized with the horseradish peroxidase (HRP) enzyme. FIGS. 13(A-B) show a photomicrograph (FIG. 13(A)) of a control slide to which no BSA-BF was added, and FIG. 13(B) is a photomicrograph of the slide to which the BSA-BF had been used. The HRP enzyme catalyzed the deposition of tyramide-TAMRA, which stains the slide with a pink chromogen where the BSA-BF was attached to the tissue. Without the presence of the BSA-BF, under the same experimental conditions, no pink chromogen is deposited (FIG. 13(A)), suggesting that exogenously added BSA protein can be permanently fixed into paraffin embedded tissue sections.

Figure 14A:
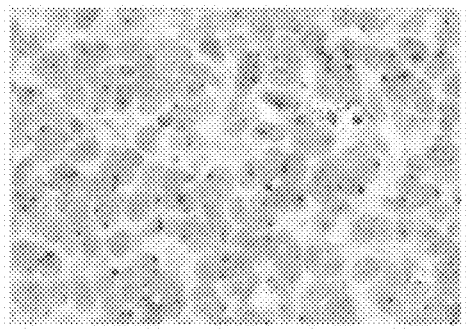
FIG. 14(A) is without tyrosine enhancement and FIG. 14(B) is with tyrosine enhancement.
Figure 14B:
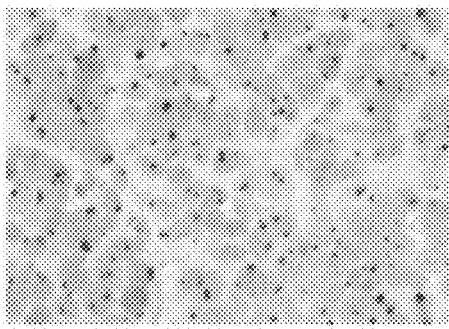

It was discovered that applying a signaling conjugate, as described herein, for certain embodiments is more efficient using a tyrosine enhancement agent following non-staining tyramide deposition cycles. To confirm this hypothesis, tissue samples were subjected to multiple rounds of TSA with a tyramide-hapten conjugate. FIGS. 14(A-B) are photomicrographs of a first sample (FIG. 14(A)) to which a signaling conjugate, as described herein, was deposited and FIG. 14(B) is a second sample in which a tyrosine enhancement solution was used prior to detection with the signaling conjugate. The difference between FIG. 14(A) and FIG. 14(B) supports the hypothesis that the availability of protein within the sample is diminished by TSA depositions and that the addition of the tyrosine-containing enhancers can provide more robust staining. In the absence of protein fixation (FIG. 14(A)) the subsequent deposition of the signaling conjugate produced a low level of chromogenic signal. When the exogenous protein was fixed into the tissue section using paraformaldehyde (FIG. 14(B)), the signaling conjugate produced signals significantly more intense and numerous. The data suggests that fixation of exogenous protein to tissue sections enhances tyramide signal amplification by providing additional protein binding sites for the tyramide reagents to covalently attach.

One disclosed embodiment of a method for detecting a target in a sample comprises: contacting the sample with a detection probe specific to the target; contacting the sample with a tyrosine enhancer; contacting the sample with a cross-linking agent; contacting the sample with a tyramide-based detection reagent; and detecting the target in the sample; wherein the cross-linking reagent covalently attaches the tyrosine enhancer to the sample. In one embodiment, the method further comprises contacting the sample with a labeling conjugate. In another embodiment, the method further comprises contacting the sample with an amplifying conjugate. In one embodiment, the method further comprises detecting a second target, wherein contacting the sample with the tyrosine enhancer occurs subsequent to contacting the sample with the tyramide-based detection reagents for the first target and prior to contacting the sample with tyramide-based detection reagents for the second target. In one embodiment, the tyrosine enhancer includes a protein. In another embodiment, the tyrosine enhancer is a polymer containing tyrosine residues. In one embodiment, the cross-linking agent is formalin or formaldehyde. In another embodiment, the crosslinking agent is neutral buffered formalin (NBF). In another embodiment the cross-linking agent is an imidoester, a dimethyl suberimidate, or a N-Hydroxysuccinimide-ester (NHS ester). In another embodiment, the cross-linking agent is light radiation. In one embodiment, the cross-linking agent is UV light or X-ray radiation. In one embodiment, detecting the target in the sample includes imaging at least one of the tyramide-based detection reagents. In another embodiment, detecting the target includes fluorescently imaging at least one of the tyramide-based detection reagents. In another embodiment, detecting the target includes imaging at least one of the tyramide-based detection reagents, the tyramide-based detection reagents yielding a chromogenic signal detectable using bright-field light microscopy. In another embodiment, detecting the target includes imaging a signaling conjugate. In another embodiment, detecting the target includes imaging a chromogen that was deposited in the vicinity of at least one of the tyramide-based detection reagents.

Counterstaining

Counterstaining is a method of post-treating the samples after they have already been stained with agents to detect one or more targets, such that their structures can be more readily visualized under a microscope. For example, a counterstain is optionally used prior to cover-slipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. In some examples, more than one stain can be mixed together to produce the counterstain. This provides flexibility and the ability to choose stains. For example, a first stain can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain. One aspect of the present disclosure is that the counterstaining methods known in the art are combinable with the disclosed methods and compositions so that the stained sample is easily interpretable by a reader.

III. Conjugates

Disclosed herein are various different conjugates suitable for use in the disclosed method. The various classes of conjugates contemplated by the present disclosure are described below.

A. Detection Probes

The present disclosure concerns particular detection probes that may be used to detect a target in a sample, for example a biological sample. The detection probes include a specific binding moiety that is capable of specifically binding to the target. Detection probes include one or more features that enable detection through a labeling conjugate. Representative detection probes include nucleic acid probes and primary antibody probes.

In illustrative embodiments, the detection probe is an oligonucleotide probe or an antibody probe. As described herein, detection probes may be indirect detection probes. Indirect detection probes are not configured to be detected directly. In particular, the probes are not configured for the purpose of direct visualization. Instead, detection probes will generally be one of two types, although these are not mutually exclusive types. The first type of detection probe is haptenated and the second type of detection probes are based on a particular species of antibody. Other types of detection probes are known in the art and within the scope of the current disclosure, but these are less commonly implemented, for example aptamer-labeled probes or antibodies, nucleic acid tagged probes or antibodies, antibodies that are covalently bound to other antibodies so as to provide dual-binding capabilities (e.g., through coupling techniques or through fusion proteins). While not configured as such, some of the detection probes may have properties that enable their direct detection. For example, using haptens fluorophores is within the scope of the present disclosure. According to one embodiment, the detection probe includes a hapten label. Those of ordinary skill in the art appreciate that a detection probe can be labeled with one or more haptens using various approaches. The detection probe may include a hapten selected from the group consisting an oxazole hapten, pyrazole hapten, thiazole hapten, nitroaryl hapten, benzofuran hapten, triterpene hapten, urea hapten, thiourea hapten, rotenoid hapten, coumarin hapten, cyclolignan hapten, di-nitrophenyl hapten, biotin hapten, digoxigenin hapten, fluorescein hapten, and rhodamine hapten. In other examples, the detection probe is monoclonal antibody derived from a second species such as goat, rabbit, mouse, or the like. For labeling a hapten-labeled detection probe, the labeling conjugate would include an anti-hapten antibody. For labeling a species-based detection probe, the labeling conjugate may be configured with an anti-species antibody.

In illustrative embodiments, the present disclosure describes nucleic acid probes which hybridize to one or more target nucleic acid sequences. The nucleic acid probe preferably hybridizes to a target nucleic acid sequence under conditions suitable for hybridization, such as conditions suitable for in situ hybridization, Southern blotting, or Northern blotting. Preferably, the detection probe portion comprises any suitable nucleic acid, such as RNA, DNA, LNA, PNA or combinations thereof, and can comprise both standard nucleotides such as ribonucleotides and deoxyribonucleotides, as well as nucleotide analogs. LNA and PNA are two examples of nucleic acid analogs that form hybridization complexes that are more stable (i.e., have an increased Tm) than those formed between DNA and DNA or DNA and RNA. LNA and PNA analogs can be combined with traditional DNA and RNA nucleosides during chemical synthesis to provide hybrid nucleic acid molecules than can be used as probes. Use of the LNA and PNA analogs allows modification of hybridization parameters such as the Tm of the hybridization complex. This allows the design of detection probes that hybridize to the detection target sequences of the target nucleic acid probes under conditions that are the same or similar to the conditions required for hybridization of the target probe portion to the target nucleic acid sequence.

Suitable nucleic acid probes can be selected manually, or with the assistance of a computer implemented algorithm that optimizes probe selection based on desired parameters, such as temperature, length, GC content, etc. Numerous computer implemented algorithms or programs for use via the internet or on a personal computer are available. For example, to generate multiple binding regions from a target nucleic acid sequence (e.g., genomic target nucleic acid sequence), regions of sequence devoid of repetitive (or other undesirable, e.g., background-producing) nucleic acid sequence are identified, for example manually or by using a computer algorithm, such as RepeatMasker. Methods of creating repeat depleted and uniquely specific probes are found in, for example, US Patent Publication No. 2012/0070862, which is hereby incorporated by reference in its entirety. Within a target nucleic acid sequence (e.g., genomic target nucleic acid sequence) that spans several to several-hundred kilobases, typically numerous binding regions that are substantially or preferably completely free of repetitive (or other undesirable, e.g., background-producing) nucleic acid sequences are identified.

In some embodiments, a hapten is incorporated into the nucleic acid probe, for example, by use of a haptenylated nucleoside. Methods for conjugating haptens and other labels to dNTPs (e.g., to facilitate incorporation into labeled probes) are well known in the art. Indeed, numerous labeled dNTPs are available commercially, for example from Invitrogen Detection Technologies (Molecular Probes, Eugene, Oreg.). A label can be directly or indirectly attached to a dNTP at any location on the dNTP, such as a phosphate (e.g., $\alpha$, $\beta$ or $\gamma$ phosphate) or a sugar. The probes can be synthesized by any suitable, known nucleic acid synthesis method. In some embodiments, the detection probes are chemically synthesized using phosphoramidite nucleosides and/or phosphoramidite nucleoside analogs. For example, in some embodiments, the probes are synthesized by using standard RNA or DNA phosphoramidite nucleosides. In some embodiments, the probes are synthesized using either LNA phosphoramidites or PNA phosphoramidites, alone or in combination with standard phosphoramidite nucleosides. In some embodiments, haptens are introduced on a basic phosphoramidites containing the desired detectable moieties. Other methods can also be used for detection probe synthesis. For example, a primer made from LNA analogs or a combination of LNA analogs and standard nucleotides can be used for transcription of the remainder of the probe. As another example, a primer comprising detectable moieties is utilized for transcription of the rest of the probe. In still other embodiments, segments of the probe produced, for example, by transcription or chemical synthesis, may be joined by enzymatic or chemical ligation.

A variety of haptens may be used in the detectable moiety portion of the detection probe. Such haptens include, but are not limited to, pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by podophyllotoxin and podophyllotoxin derivatives; and combinations thereof. Fluorescein derivatives (FITC, TAMRA, Texas Red, etc.), Digoxygenin (DIG), 5-Nitro-3-pyrozole-carbamide (nitropyrazole, NP), 4,5,-Dimethoxy-2-nitrocinnamide (nitrocinnamide, NCA), 2-(3,4-Dimethoxyphenyl)-quinoline-4-carbamide (phenylquinolone, DPQ), 2,1,3-Benzoxadiazole-5-carbamide (benzofurazan, BF), 3-Hydroxy-2-quinoxalinecarbamide (hydroxy quinoxaline, HQ), 4-(Dimethylamino)azobenzene-4'-sulfonamide (DABSYL), Rotenone isoxazoline (Rot), (E)-2-(2-(2-oxo-2,3-dihydro-1H-benzo[b][1,4]diazepin-4-yl)phenozy)acetamide (benzodiazepine, BD), 7-(diethylamino)-2-oxo-2H-chromene-3-carboxylic acid (coumarin 343, CDO), 2-Acetamido-4-methyl-5-thiazolesulfonamide (thiazolesulfonamide, TS), and p-Mehtoxyphenylpyrazopodophyllamide (Podo). These haptens and their use in probes are described in more detail in U.S. Pat. No. 7,695,929, which is hereby incorporated herein by reference in its entirety.

B. Labeling Conjugates & Secondary Labeling Conjugates

In illustrative embodiments, the labeling conjugate specifically binds to the detection probe and is configured to label the target with an enzyme. As described above, detection probes configured from a second species or to include a hapten can be detected by either an anti-species antibody or an anti-hapten antibody. One approach to configuring a labeling conjugate has been to directly couple an enzyme to the anti-species or anti-hapten antibody. Conjugates of this kind, which may or may not include various linkers, are also described in U.S. Pat. No. 7,695,929. The labeling conjugate includes one or more enzymes. Exemplary enzymes include oxidoreductases or peroxidases. The signaling conjugate includes a latent reactive moiety and a chromogenic moiety. The enzyme catalyzes conversion of the latent reactive moiety into a reactive moiety which covalently binds to the biological sample proximally to or directly on the target.

The secondary labeling conjugate is used in connection with the amplifying conjugates, as described herein. Secondary labeling conjugates are configured in the same manner as labeling conjugates except that they are configured to label haptens deposited through an amplification process instead of haptens conjugated to detection conjugates. In illustrative embodiments, a secondary labeling conjugate comprises an anti-hapten antibody conjugated to an enzyme. In one embodiment, the enzyme is an oxidoreductase or a peroxidase.

C. Signaling Conjugate

Another type of conjugate disclosed herein is a signaling conjugate. The signaling conjugate provides the detectable signal that is used to detect the target, according to the methods disclosed herein. In particular disclosed embodiments, the signaling conjugate comprises a latent reactive moiety and a chromophore moiety.

One aspect of the present disclosure is that the signaling conjugates may be configured to absorb light more selectively than traditionally available chromogens. Detection is realized by absorbance of the light by the signaling conjugate; for example, absorbance of at least about 5% of incident light would facilitate detection of the target. In other darker stains, at least about 20% of incident light would be absorbed. Non-uniform absorbance of light within the visible spectra results in the chromophore moiety appearing colored. The chromogen conjugates disclosed herein may appear colored due to their absorbance; the chromogen conjugates may appear red, orange, yellow, green, indigo, or violet depending on the spectral absorbance associated with the chomophore moiety. According to another aspect, the chromophore moieties may have narrower spectral absorbances than those absorbances of traditionally used chromogens (e.g., DAB, Fast Red, Fast Blue). In illustrative embodiments, the spectral absorbance associated with the first chromophore moiety of the first signaling conjugate has a full-width half-max (FWHM) of between about 30 nm and about 250 nm, between about 30 nm and about 150 nm, between about 30 nm and about 100 nm, or between about 20 nm and about 60 nm.

Narrow spectral absorbances enable the signaling conjugate chromophore moiety to be analyzed differently than traditional chromogens. While having enhanced features compared to traditionally chromogens, detecting the signaling conjugates remains simple. In illustrative embodiments, detecting comprises using a bright-field microscope or an equivalent digital scanner.

An embodiment of the disclosed signaling conjugate is illustrated in FIGS. 2(A) and 2(B). Referring to FIGS. 2(A-B), the signaling conjugate 12 comprises a latent reactive moiety 4 and a chromophore moiety 6; in another embodiment, an alternative signaling conjugate 14 may include a linker 8 for conjugating chromophore moiety 6 to latent reactive moiety $\lambda_{max}$ In particular disclosed embodiments, the signaling conjugate has the following general Formula 1:

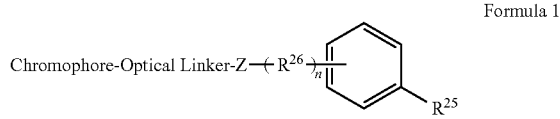

Formula 1

The disclosed signaling conjugate typically comprises a latent reactive moiety as described herein. For example, the latent reactive moiety may be the same or different from that of the disclosed amplification conjugate; however, each latent reactive moiety is capable of forming a reactive radical species and has the general formula provided herein. As shown in Formula 1, the signaling conjugate may comprise an optional linker. If a linker is used, it may be selected from any of the linkers disclosed herein. In particular disclosed embodiments, the linker is selected to improve hydrophilic solution solubility of the signaling conjugate, and/or to improve conjugate functionality on the biological sample. In particular disclosed embodiment, the linker is an alkylene oxide linker, such as a polyethylene glycol linker; however, any of the linkers disclosed herein may be used for the signaling conjugate.

1. Chromophore Moiety

A chromophore moiety is generally described as the part of a molecule responsible for its color. Colors arise when a molecule absorbs certain wavelengths of visible light and transmits or reflects others. The chromophore is a region in the molecule where the energy difference between two different molecular orbitals falls within the range of the visible spectrum, wherein visible light interacting with that region can be absorbed. The absorbance is usually associated with an electron transition from its ground state to an excited state. Molecules having ground state to excited state energy differences within the visible spectrum are often conjugated carbon structures. In these compounds, electrons transition between energy levels that are extended pi-orbitals, created by a series of alternating single and double bonds, often in aromatic systems. Common examples include various food colorings, fabric dyes (azo compounds), pH indicators, lycopene, β-carotene, and anthocyanins. The structure of the molecule imparts the characteristic of the pi-orbitals which result in the energy level. Typically, lengthening or extending a conjugated system with more unsaturated (multiple) bonds in a molecule will tend to shift absorption to longer wavelengths. Woodward-Fieser rules can be used to approximate ultraviolet-visible maximum absorption wavelength in organic compounds with conjugated pi-bond systems.

In illustrative embodiments, metal complexes can be chromophores. For example, a metal in a coordination complex with ligands will often absorb visible light. For example, chlorophyll and hemoglobin (the oxygen transporter in the blood of vertebrate animals) are chromophores that include metal complexes. In these two examples, a metal is complexed at the center of a porphyrin ring: the metal being iron in the heme group of hemoglobin, or magnesium in the case of chlorophyll. The highly conjugated pi-bonding system of the porphyrin ring absorbs visible light. The nature of the central metal can also influence the absorption spectrum of the metalloporphyrin complex or properties such as excited state lifetime.

In illustrative embodiments, the chromophore moiety is a coumarin or coumarin derivative. A general formula for coumarin and coumarin derivatives is provided below.

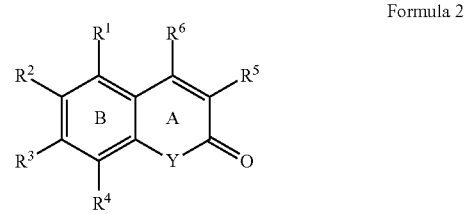

Formula 2

With reference to Formula 2, $R^1$-$R^6$ are defined herein. At least one of the $R^1$-$R^6$ substituents also typically is bonded to a linker or the latent reactive moiety (e.g., a tyramide or tyramide derivative). Certain working embodiments have used the position indicated as having an $R^5$ substituent for coupling to a linker or latent reactive moiety (e.g., a tyramide or tyramide derivative). Substituents other than hydrogen at the 4 position are believed to quench fluorescence, but are useful within the scope of the present disclosure. Y is selected from oxygen, nitrogen or sulfur. Two or more of the $R^1$-$R^6$ substituents available for forming such compounds also may be atoms, typically carbon atoms, in a ring system bonded or fused to the compounds having the illustrated general formula. Exemplary embodiments of these types of compounds include:

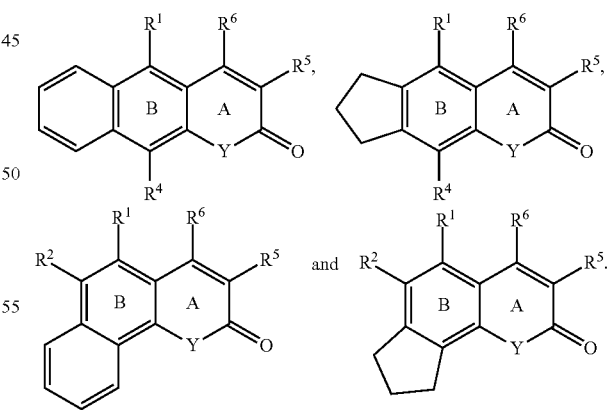

A person of ordinary skill in the art will appreciate that the rings also could be heterocyclic and/or heteroaryl.

Working embodiments typically comprise fused A-D ring systems having at least one linker, tyramide, or tyramide derivative coupling position, with one possible coupling position being indicated below:

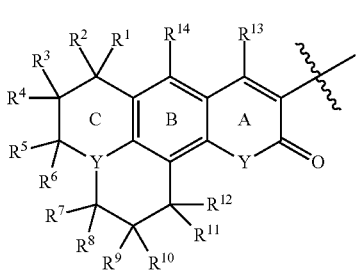

Formula 3

With reference to Formula 3, the R and Y variable groups are as stated herein. Most typically, $R^1$-$R^{14}$ independently are hydrogen or lower alkyl. Particular embodiments of coumarin-based chromophores include 2,3,6,7-tetrahydro-11-oxo-1H,5H,11H-[1]benzopyrano[6,7,8-ij]quinolizine-10-carboxylic acid

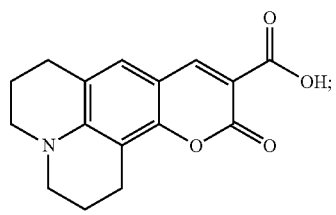 [SMILES: O=C(O)c1cc2cc3c4c(c2oc1=O)CCCN4CCC3]

and 7-(diethylamino)coumarin-3-carboxylic acid

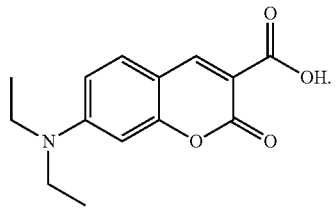 [SMILES: CCN(CC)c1ccc2cc(C(=O)O)c(=O)oc2c1]

Another class of chromogenic moieties suitable for use herein include diazo-containing chromogens. These particular chromophores may have a formula as illustrated below.

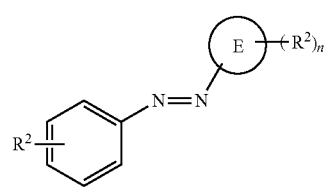

With respect to this formula, ring E may be selected from phenyl, imidazole, pyrazole, oxazole, and the like. Each $R^2$ independently may be selected from those groups recited herein. In particular disclosed embodiments, each $R^2$ independently is selected from amine, substituted amine, phenyl, hydroxyl, sulfonyl chloride, sulfonate, carboxylate, and combinations thereof; and n may range from zero to 5. Particular disclosed embodiments may be selected from the following diazo chromophores: DABSYL, which has a $\lambda_{max}$ of about 436 nm and has the following chemical structure

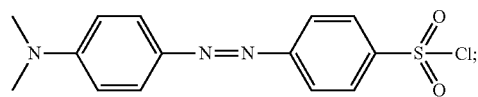

and

Tartrazine, which has a $\lambda_{max}$ of about 427 nm and has the following chemical structure

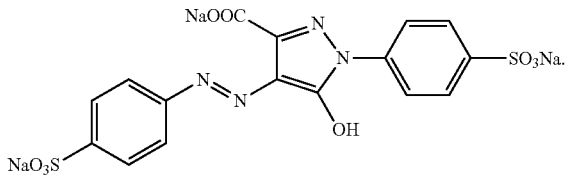

In yet other embodiments, the chromophore may be a triarylmethane compound. Triarylmethane compounds within the scope of the present disclosure may have the following formula.

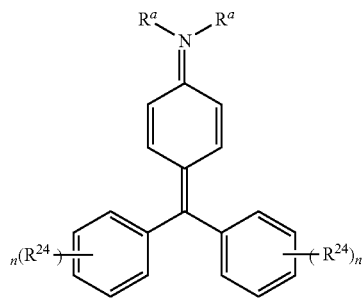

Formula 4

With respect to Formula 4, each $R^a$ independently may be selected from hydrogen, aliphatic, aryl, and alkyl aryl; and each $R^{24}$ may be selected from amine, substituted amine, hydroxyl, alkoxy, and combinations thereof; each n independently may range from zero to 5. Exemplary chromophores are provided below:

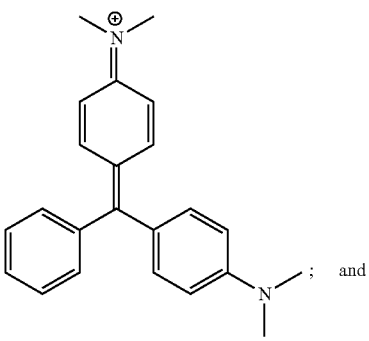

and

-continued

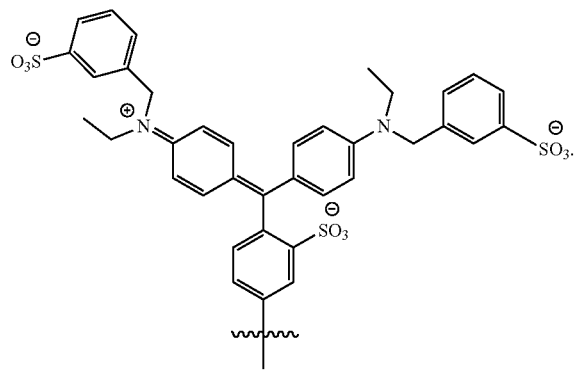

In other disclosed embodiments, the chromophore moiety may have the following formula

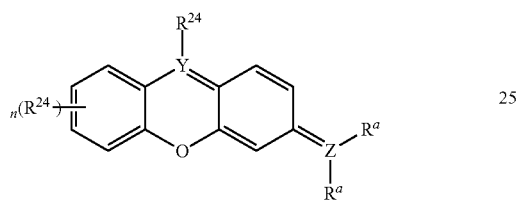

wherein each $R^a$ independently may be selected from hydrogen, aliphatic, aryl, and alkyl aryl; each $R^{24}$ independently may be selected from the groups provided herein, including substituted aryl, which comprises an aryl group substituted with one or more groups selected from any one of $R^1$-$R^{23}$, which are disclosed herein; Y may be nitrogen or carbon; Z may be nitrogen or oxygen; and n may range from zero to $\lambda_{max}$ In particular disclosed embodiments, Z is nitrogen and each $R^a$ may be aliphatic and fused with a carbon atom of the ring to which the amine comprising $R^a$ is attached, or each Ra may join together to form a 4 or 6-membered aliphatic or aromatic ring, which may be further substituted. Exemplary embodiments are provided as follows:

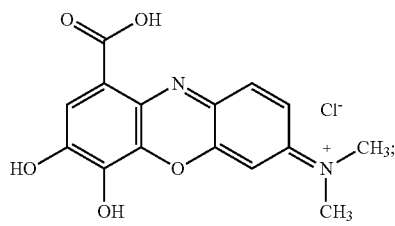

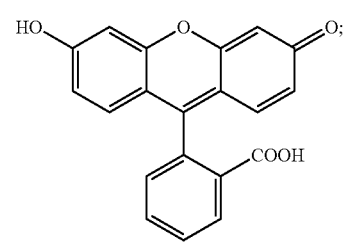

-continued

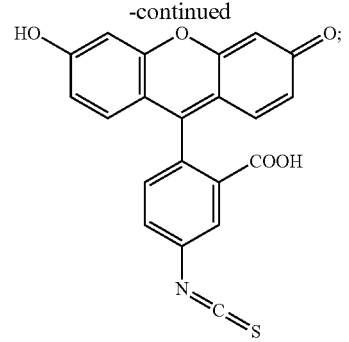

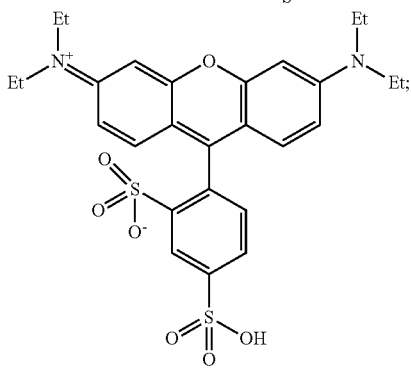

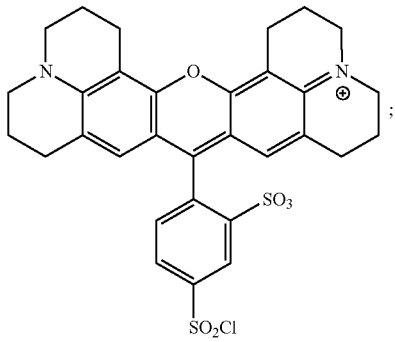

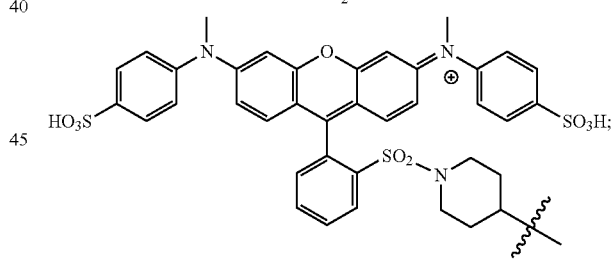

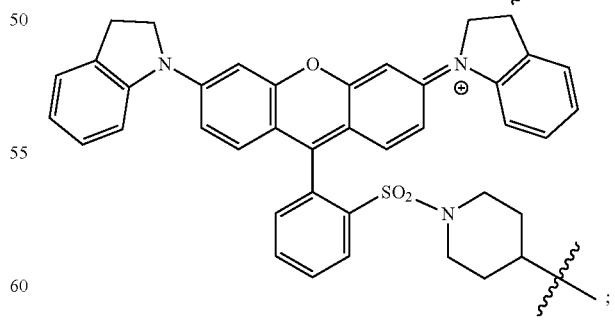

and other rhodamine derivatives, such as tetramethylrhodamines (including TMR, TAMRA, and reactive isothiocyanate derivatives), and diarylrhodamine derivatives, such as the QSY 7, QSY 9, and QSY 21 dyes.

Exemplary chromophores are selected from the group consisting of DAB; AEC; CN; BCIP/NBT; fast red; fast blue; fuchsin; NBT; ALK GOLD; Cascade Blue acetyl azide; Dapoxylsulfonic acid/carboxylic acid succinimidyl ester; DY-405; Alexa Fluor 405 succinimidyl ester; Cascade Yellow succinimidyl ester; pyridyloxazole succinimidyl ester (PyMPO); Pacific Blue succinimidyl ester; DY-415; 7-hydroxycoumarin-3-carboxylic acid succinimidyl ester; DYQ-425; 6-FAM phosphoramidite; Lucifer Yellow; iodoacetamide; Alexa Fluor 430 succinimidyl ester; Dabcyl succinimidyl ester; NBD chloride/fluoride; QSY 35 succinimidyl ester; DY-485XL; Cy2 succinimidyl ester; DY-490; Oregon Green 488 carboxylic acid succinimidyl ester; Alexa Fluor 488 succinimidyl ester; BODIPY 493/503 C3 succinimidyl ester; DY-480XL; BODIPY FL C3 succinimidyl ester; BODIPY FL C5 succinimidyl ester; BODIPY FL-X succinimidyl ester; DYQ-505; Oregon Green 514 carboxylic acid succinimidyl ester; DY-510XL; DY-481XL; 6-carboxy-4',5'-dichloro-2',7'-dimethoxyfluorescein succinimidyl ester (JOE); DY-520XL; DY-521XL; BODIPY R6G C3 succinimidyl ester; erythrosin isothiocyanate; 5-carboxy-2',4',5',7'-tetrabromosulfonefluorescein succinimidyl ester; Alexa Fluor 532 succinimidyl ester; 6-carboxy-2',4,4',5'7,7'-hexachlorofluorescein succinimidyl ester (HEX); BODIPY 530/550 C3 succinimidyl ester; DY-530; BODIPY TMR-X succinimidyl ester; DY-555; DYQ-1; DY-556; Cy3 succinimidyl ester; DY-547; DY-549; DY-550; Alexa Fluor 555 succinimidyl ester; Alexa Fluor 546 succinimidyl ester; DY-548; BODIPY 558/568 C3 succinimidyl ester; Rhodamine red-X succinimidyl ester; QSY 7 succinimidyl ester; BODIPY 564/570 C3 succinimidyl ester; BODIPY 576/589 C3 succinimidyl ester; carboxy-X-rhodamine (ROX); succinimidyl ester; Alexa Fluor 568 succinimidyl ester; DY-590; BODIPY 581/591 C3 succinimidyl ester; DY-591; BODIPY TR-X succinimidyl ester; Alexa Fluor 594 succinimidyl ester; DY-594; carboxynaphthofluorescein succinimidyl ester; DY-605; DY-610; Alexa Fluor 610 succinimidyl ester; DY-615; BODIPY 630/650-X succinimidyl ester; erioglaucine; Alexa Fluor 633 succinimidyl ester; Alexa Fluor 635 succinimidyl ester; DY-634; DY-630; DY-631; DY-632; DY-633; DYQ-2; DY-636; BODIPY 650/665-X succinimidyl ester; DY-635; Cy5 succinimidyl ester; Alexa Fluor 647 succinimidyl ester; DY-647; DY-648; DY-650; DY-654; DY-652; DY-649; DY-651; DYQ-660; DYQ-661; Alexa Fluor 660 succinimidyl ester; Cy5.5 succinimidyl ester; DY-677; DY-675; DY-676; DY-678; Alexa Fluor 680 succinimidyl ester; DY-679; DY-680; DY-682; DY-681; DYQ-3; DYQ-700; Alexa Fluor 700 succinimidyl ester; DY-703; DY-701; DY-704; DY-700; DY-730; DY-731; DY-732; DY-734; DY-750; Cy7 succinimidyl ester; DY-749; DYQ-4; and Cy7.5 succinimidyl ester.

In particular disclosed embodiments, the chromophore moiety may be selected from tartrazine, 7-diethylaminocoumarin-3-carboxylic acid, succinimidyl ester, Dabsyl sulfonyl chloride, fluorescein isothiocyanate (FITC) carboxy succinimidyl ester (DY-495), Rhodamine Green carboxylic acid succinimidyl ester (DY-505), eosin isothiocyanate (EITC), 6-carboxy-2',4,7,7'-tetrachlorofluorescein succinimidyl ester (TET), carboxyrhodamine 6G succinimidyl ester, carboxytetramethylrhodamine succinimidyl ester (TMR, TAMRA) (DY-554), QSY 9 succinimidyl ester, sulforhodamine B sulfonyl chloride (DY-560), Texas Red (sulforhodamine 101), gallocyanine, Fast Green FCF, Malachite Green, isothiocyanate, and QSY 21 succinimidyl ester. In certain disclosed embodiments, the chromophore moiety of the signaling conjugate is other than Dabsyl sulfonyl chloride, FITC, 7-diethylaminocoumarin-3-carboxylic acid, succinimidyl ester, Rhodamine Green carboxylic acid succinimidyl ester (DY-505), eosin isothiocyanate (EITC), 6-carboxy-2',4,7,7'-tetrachlorofluorescein succinimidyl ester (TET), carboxytetramethylrhodamine succinimidyl ester (TMR, TAMRA) (DY-554), sulforhodamine B sulfonyl chloride (DY-560), Texas Red (sulforhodamine 101), and gallocyanine.

Further exemplary chromogenic moieties that are used for the signaling conjugate are provided below:

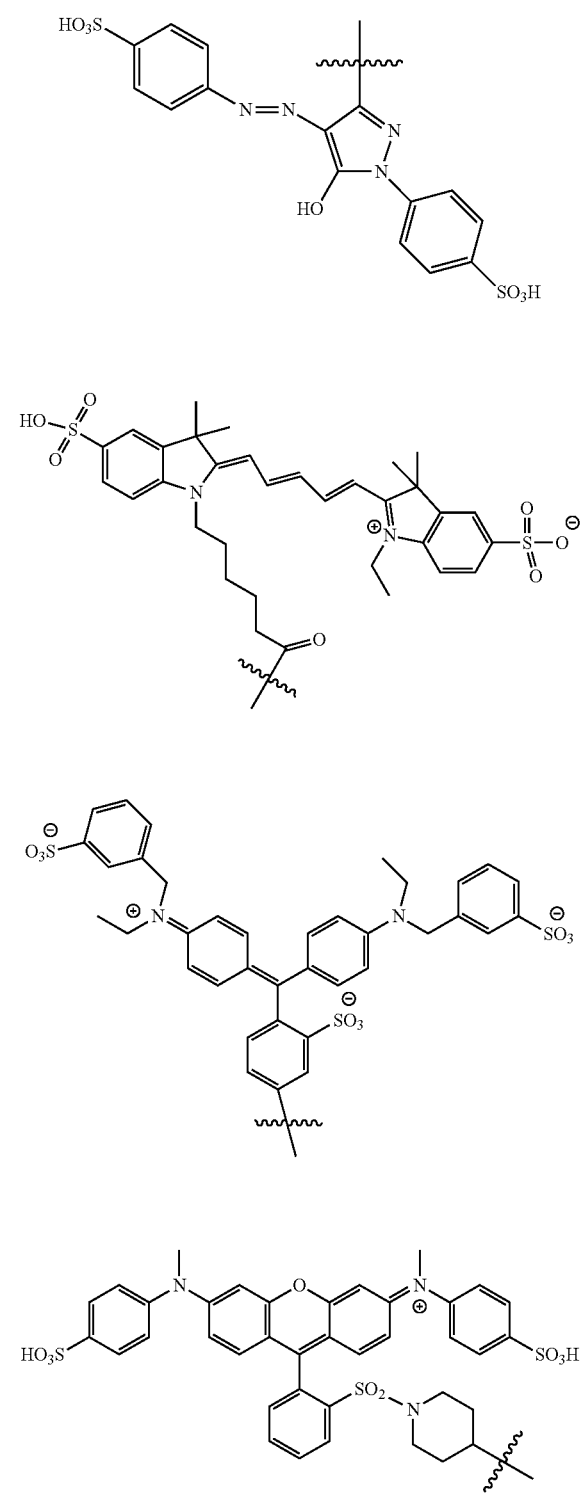

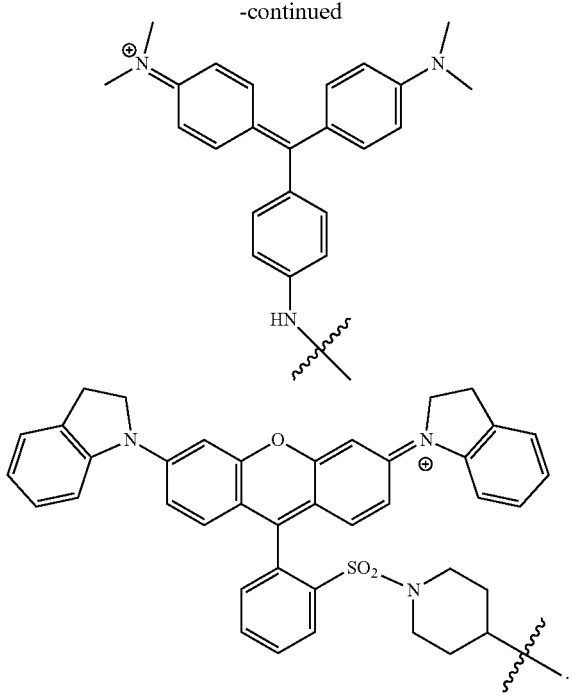

In illustrative embodiments of the present disclosure, the signaling conjugate has absorption maxima and absorption breadths particularly suited for bright-field imaging of targets in biological samples. In one embodiment, a signaling conjugate is configured to provide an absorbance peak having a $\lambda_{max}$ of between about 350 nm and about 800 nm, between about 400 nm and about 750 nm, or between about 400 nm and about 700 nm. These wavelength ranges are of particular interest because they translate into colors visible to humans. However, the approaches described herein could also be applied to chromophore moieties useful for near infrared (NIR), infrared (IR), or ultraviolet (UV) diagnostic methodologies.

In one embodiment the signaling conjugate is configured to produce a colored signal selected from the group consisting of red, orange, yellow, green, indigo, violet, or mixtures thereof. In one embodiment, a signaling conjugate has a $\lambda_{max}$ of between about 400 nm and 430 nm. In another embodiment, the signaling conjugate produces a yellow signal. In one embodiment, a signaling conjugate has a $\lambda_{max}$ of between about 430 nm and 490 nm. In another embodiment, the signaling conjugate produces an orange signal. In one embodiment, a signaling conjugate has a $\lambda_{max}$ of between about 490 nm and 560 nm. In another embodiment, the signaling conjugate produces a red signal. In one embodiment, a signaling conjugate has a $\lambda_{max}$ of between about 560 nm and 570 nm. In another embodiment, the signaling conjugate produces a violet signal. In one embodiment, a signaling conjugate has a $\lambda_{max}$ of between about 570 nm and 580 nm. In another embodiment, the signaling conjugate produces an indigo signal. In one embodiment, a signaling conjugate has a $\lambda_{max}$ of between about 580 nm and 620 nm. In another embodiment, the signaling conjugate produces a blue signal. In one embodiment, a signaling conjugate has a $\lambda_{max}$ of between about 620 nm and about 800 nm. In another embodiment, the signaling conjugate produces a green signal.

In one embodiment, the signaling conjugate is configured to have a full-width half-max (FWHM) of between about 20 nm and about 60 nm, between about 30 and about 100 nm, between about 30 and about 150 nm, or between about 30 and about 250 nm. In particular disclosed embodiments, the FWHM is less than about 300 nm, less than about 250 nm, less than about 200 nm, less than about 150 nm, less than about 100 nm, less than about 50 nm. In illustrative embodiments, a signaling conjugate having a FWHM of less than about 150 nm is described. In one embodiment, the FWHM is less than about 150 nm, less than about 120 nm, less than about 100 nm, less than about 80 nm, less than about 60 nm, less than about 50 nm, less than about 40 nm, less than about 30 nm, between about 10 nm and 150 nm, between about 10 nm and 120 nm, between about 10 nm and 100 nm, between about 10 nm and 80 nm, between about 10 nm and 60 nm, between about 10 nm and 50 nm, or between about 10 nm and 40 nm.

In another embodiment, the signaling conjugate has an average molar absorptivity of greater than about 5,000 $M^{-1}$ $cm^{-1}$ to about 90,000 $M^{-1}$ $cm^{-1}$. For example, an average molar absorptivity of greater than about 5,000 $M^{-1}$ $cm^{-1}$, greater than about 10,000 $M^{-1}$ $cm^{-1}$, greater than about 20,000 $M^{-1}$ $cm^{-1}$, greater than about 40,000 $M^{-1}$ $cm^{-1}$, or greater than about 80,000 $M^{-1}$ $cm^{-1}$. In yet another embodiment, the signaling conjugate has a solubility in water of at least about 0.1 mM to about 1 M. For example, the signaling conjugate has a solubility in water of at least about 0.1 mM, at least about 1 mM, at least about 10 mM, at least about 100 mM, or at least about 1 M. In one embodiment, the signaling conjugate is stable against precipitation in an aqueous buffered solution for greater than about 1 month to about 30 months. For example, the signaling conjugate is stable against precipitation in an aqueous buffered solution for greater than about 1 month, greater than about 3 months, greater than about 6 months, greater than about 12 months, greater than about 18 months, or greater than about 24 months.

Figures 15A, 15B:
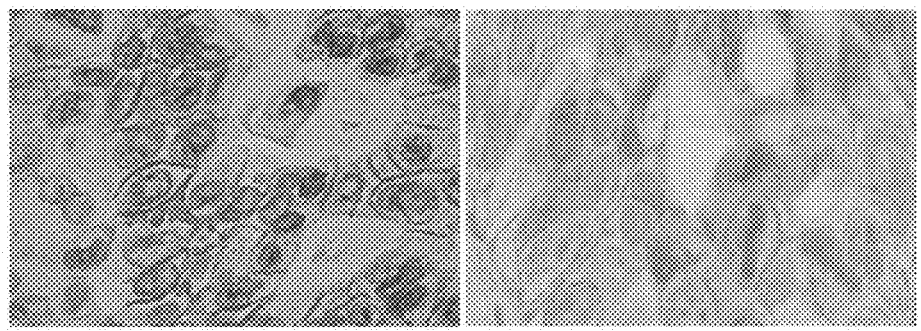
FIGS. 15(A-B) are photomicrographs showing a HER2 (4B5) IHC in Calu-3 xenografts stained with two different signaling conjugate having the absorption spectra shown in FIG. 16.
Figure 16:
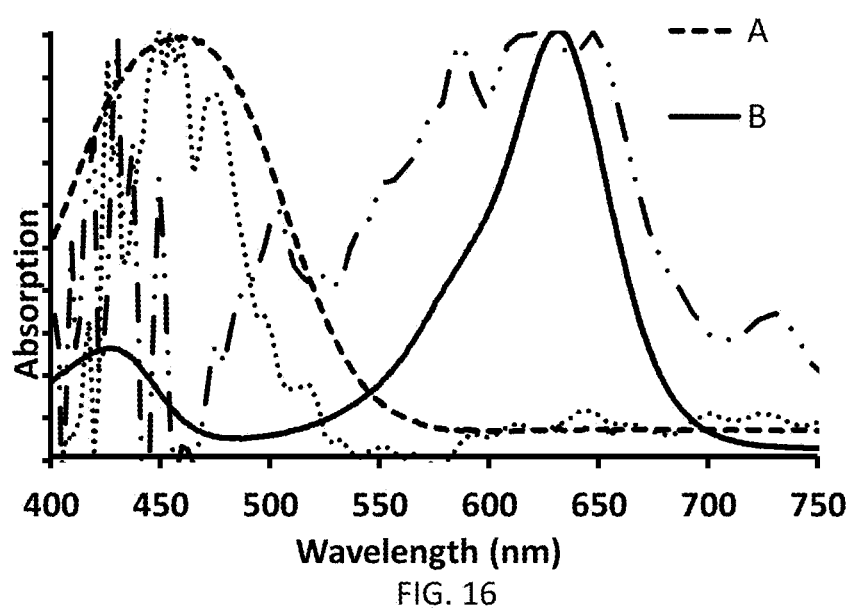
FIG. 16 illustrates absorbance spectra of two signaling conjugates in solution and as used to stain the samples shown in FIGS. 15(A-B).

As described herein, the FWHM of the absorption peak significantly contributes to the observed color of the signaling conjugate. Referring to FIG. 6(A-B), several colors are observed for light observed over a relatively small span of wavelengths. In particular, yellow light is only apparent across a relatively narrow span of 20 nm. To impart a yellow color on a substance, a relatively narrow span of visible wavelengths should be absorbed (400-430 nm). Referring to FIGS. 7(A) and 7(B), the signaling conjugate shown therein has a FWHM of approximately 40 nm. FIG. 15(A) is a first photomicrograph and FIG. 15(B) is a second photomicrograph of a protein stained (HER2 (4B5) IHC in Calu-3 xenografts) using the signaling conjugate having the absorption spectra shown in FIG. 16. Trace A corresponds to the signaling conjugate used for FIG. 15(A) and trace B corresponds to the signaling conjugated used for FIG. 15(B); note that each signaling conjugate was analyzed with spectrometry in solution prior to staining and on the slide subsequent to having detected the HER2 (the dashed traces representing the spectra obtained on the tissue). The signaling conjugate used to stain the tissue shown in FIG. 15(A) has a $\lambda_{max}$ of about 456 nm and a FWHM of about 111 nm. The signaling conjugate used to stain the tissue shown in FIG. 15(B) has a $\lambda_{max}$ of about 628 nm and a FWHM of about 70 nm.

Table 1 shows a classification system for the spectral properties of various signaling conjugates according to illustrative embodiments of the present disclosure. According to the classification system, there are six different colors, which a particular chromogen could be classified as, the series numbered roman numerals one through six (i.e., I-VI). For each color classification, there are five band-width classifications, those band-width classifications being made according to broader FWHM measurements. Accordingly, band-width classification (a) is the narrowest and includes those signaling conjugates that have FWHM widths of between about 10 and about 40 nm. Band-width classification (e) is the broadest and includes those signaling conjugates that have FWHM widths of between about 130-160 nm. A red signaling conjugate having a $\lambda_{max}$ of about 530 nm and a FWHM of about 115 nm could be classified as a series III(d) signaling conjugate.

TABLE 1

Classification system for signaling conjugates spectral properties.

| | | FWHM (nm) | | | | |
|---|---|---|---|---|---|---|
| color | $\lambda_{max}$ (nm) | 10-40 | 40-70 | 70-100 | 100-130 | 130-160 |
| I. yellow | 350-430 | (a) | (b) | (c) | (d) | (e) |
| II. orange | 430-490 | (a) | (b) | (c) | (d) | (e) |
| III. red | 490-560 | (a) | (b) | (c) | (d) | (e) |
| IV. indigo/violet | 560-580 | (a) | (b) | (c) | (d) | (e) |
| V. blue | 580-620 | (a) | (b) | (c) | (d) | (e) |
| VI. green | 620-800 | (a) | (b) | (c) | (d) | (e) |

FIGS. 17(A-D) are photomicrographs of tissues stained with signaling conjugates having different chromogenic moieties. FIG. 17(E) shows UV-Vis spectra with traces corresponding to the absorbance of the signaling conjugates, the traces corresponding to the associated photomicrograph. As such, trace (A) of FIG. 17(E) corresponds to the signaling conjugate shown in FIG. 17(A). The other traces are similarly associated with the corresponding photomicrographs. The blue color apparent in the slide is a commercially available bluing solution. FIG. 17(A) and trace "A" of FIG. 17(E) shows a malachite green signaling conjugate. It is classifiable as a I(b) signaling conjugate according to Table 1. FIG. 17(B) and trace "B" of FIG. 17(E) shows a tartrazine signaling conjugate. It is classifiable as a I(c) signaling conjugate according to Table 1. FIG. 17(C) and trace "C" of FIG. 17(E) shows a sulforhodamine B signaling conjugate. It is classifiable as a IV(b) signaling conjugate according to Table 1. FIG. 17(D) and trace "D" of FIG. 17(E) shows a Victoria Blue signaling conjugate. It is classifiable as a VI(c) signaling conjugate according to Table 1.

FIG. 18(A-D) are photomicrographs of tissues stained with signaling conjugates having different chromogenic moieties. FIG. 18(E) shows UV-Vis spectra with traces corresponding to the absorbance of the signaling conjugates, the traces corresponding to the associated photomicrograph. FIG. 18(A) and trace "A" of FIG. 18(E) shows a coumarin (4-(diethylamino)-2-oxo-2H-chromene-3-carboxylic acid) signaling conjugate. It is classifiable as a I(b) signaling conjugate according to Table 1. FIG. 18(B) and trace "B" of FIG. 18(E) show a Dabsyl (dimethylaminoazobenzenesulfonic acid) signaling conjugate. It is classifiable as a II(b) signaling conjugate according to Table 1. FIG. 18(C) and trace "C" of FIG. 18(E) shows a TAMRA signaling conjugate. It is classifiable as a III(b) signaling conjugate according to Table 1. FIG. 18(D) and trace "D" of FIG. 18(E) shows a 5-(and-6)-carboxyrhodamine 110 signaling conjugate. It is classifiable as a V(a) signaling conjugate according to Table 1.

FIGS. 19(AD) are photomicrographs of tissues stained with signaling conjugates having different chromogenic moieties. FIG. 19(E) shows UV-Vis spectra with traces corresponding to the absorbance of the signaling conjugates, the traces corresponding to the associated photomicrograph. FIG. 19(A) and trace "A" of FIG. 19(E) shows a FITC (1-(3',6'-dihydroxy-3-oxospiro(isobenzofuran-1(3H),9'-(9H)xanthen-5-yl) signaling conjugate. It is classifiable as a III(b) signaling conjugate according to Table 1. FIG. 19(B) and trace "B" of FIG. 19(E) shows a Rhodamine 6G signaling conjugate. It is classifiable as a III(c) signaling conjugate according to Table 1. FIG. 19(C) and trace "C" of FIG. 19(E) shows a Texas Red (sulforhodamine 101) signaling conjugate. It is classifiable as a IV(c) signaling conjugate according to Table 1. FIG. 19(D) and trace "D" of FIG. 19(E) shows a cy5 signaling conjugate. It is classifiable as a VI(c) signaling conjugate according to Table 1.

FIGS. 20(AD) are photomicrographs of tissues stained with signaling conjugates having different chromogenic moieties. FIG. 20(E) shows UV-Vis spectra with traces corresponding to the absorbance of the signaling conjugates, the traces corresponding to the associated photomicrograph. FIG. 20(A) and trace "A" of FIG. 20(E) shows a Rhodamine 110 signaling conjugate. It is classifiable as a III(b) signaling conjugate according to Table 1. FIG. 20(B) and trace "B" of FIG. 20(E) shows a JOE (6-Carboxy-4',5'-dichloro-2',7'-dimethoxyfluorescein, succinimidyl ester) signaling conjugate. It is classifiable as a III(c) signaling conjugate according to Table 1. FIG. 20(C) and trace "C" of FIG. 20(E) shows a gallocyanine signaling conjugate. It is classifiable as a III(c) signaling conjugate according to Table 1. FIG. 19(D) and trace "D" of FIG. 19(E) shows a carboxyrhodamine B signaling conjugate. It is also classifiable as a III(c) signaling conjugate according to Table 1.

In illustrative embodiments, a method is disclosed for detecting multiple targets in a sample using spectrally distinct signaling conjugates. In one embodiment, the method includes using two or more signaling conjugates selected from those classifications shown in Table 1. In another embodiment, the method includes using three or more signaling conjugates selected from those classifications shown in Table 1. In another embodiment, the method includes using a first signaling conjugate from a first classification I-VI and a second signaling conjugate selected from a second classification I-VI, wherein the first and second classifications are not the same. In another embodiment, the method includes using a first signaling conjugate from a first classification I-VI, a second signaling conjugate from a second classification I-VI, and a third signaling conjugate from a third classification I-VI, wherein the first, second, and third classifications are not the same. In another embodiment, at least one of the signaling conjugates has a FWHM classification of (e) or narrower. In another embodiment, at least one of the signaling conjugates has a FWHM classification of (d) or narrower. In another embodiment, at least one of the signaling conjugates has a FWHM classification of (c) or narrower. In another embodiment, at least one of the signaling conjugates has a FWHM classification of (b) or narrower. In another embodiment, at least two signaling conjugates have FWHM classification of (e) or narrower. In another embodiment, at least three signaling conjugates have FWHM classification of (e) or narrower.

2. Latent Reactive Moiety

The latent reactive moiety is configured to undergo catalytic activation to form a reactive species that can covalently bond with the sample or to other detection components. The catalytic activation is driven by one or more enzymes (e.g., oxidoreductase enzymes and peroxidase enzymes, like horseradish peroxidase). In the presence of peroxide, these enzymes can catalyze the formation of reactive species. These reactive species, e.g., free radicals, are capable of reacting with phenolic compounds proximal to their generation, i.e., near the enzyme. The phenolic compounds available in the sample are most often tyrosyl residues within proteins. As such, the latent reactive moiety can be added to a protein-containing sample in the presence of a peroxidase enzyme and a peroxide (e.g., hydrogen peroxide), which can catalyze radical formation and subsequently cause the reactive moiety to form a covalent bond with the biological sample.

In particular disclosed embodiments, the latent reactive moiety comprises at least one aromatic moiety. In exemplary embodiments, the latent reactive moiety comprises a phenolic moiety and binds to a phenol group of a tyrosine amino acid. It is desirable, however, to specifically bind the labeling conjugate via the latent reactive moiety at, or in close proximity to, a desired target with the sample. This objective can be achieved by immobilizing the enzyme on the target region, as described herein. Only latent reactive moieties in close proximity to the immobilized enzyme will react and form bonds with tyrosine residues in the vicinity of, or proximal to, the immobilized enzyme, including tyrosine residues in the enzyme itself, tyrosine residues in the antibody to which the enzyme is conjugated, and/or tyrosine residues in the sample that are proximal to the immobilized enzyme. In particular disclosed embodiments, the labeling conjugate can be bound proximally, such as within about 100 nm, within about 50 nm, within about 10 nm, or within about 5 nm of the immobilized enzyme. For example, the tyrosine residue may be within a distance of about 10 angstroms to about 100 nm, about 10 angstroms to about 50 nm, about 10 angstroms to about 10 nm, or about 10 angstroms to about 5 nm from the immobilized enzyme. Such proximal binding allows the target to be detected with at least the same degree of specificity as conventional staining methods used with the detection methods disclosed herein. For example, embodiments of the disclosed method allow sub cellular structures to be distinguished, e.g., nuclear membrane versus the nuclear region, cellular membrane versus the cytoplasmic region, etc.

In particular disclosed embodiments, the latent reactive moiety has the general formula illustrated below.

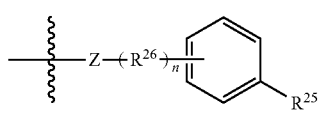

Formula 5

With reference to Formula 5, $R^{25}$ is selected from the group consisting of hydroxyl, ether, amine, and substituted amine; $R^{26}$ is selected from the group consisting of alkyl, alkenyl, alkynyl, aryl, heteroaryl, —$OR_m$, —$NR_m$, and —$SR_m$, where m is 1-20; n is 1-20; Z is selected from the group consisting of oxygen, sulfur, and $NR^a$ where $R^a$ is selected from the group consisting of hydrogen, aliphatic, aryl, and alkyl aryl. An exemplary embodiment of the latent reactive moiety is tyramine (or tyramide, which is the name given to a tyramine molecule conjugated with the detectable label and/or optional linker), or a derivative thereof.

In particular disclosed embodiments, the signaling conjugate has a minimum concentration, when covalently deposited on the sample, of greater than about $1 \times 10^{11}$ molecules per $cm^2 \cdot \mu m$ or greater than about to about $1 \times 10^{13}$ molecules per $cm^2 \cdot \mu m$ within the biological sample. In particular disclosed embodiments, the concentration of signaling conjugate deposited ranges from about to about $1 \times 10^{11}$ molecules per $cm^2 \cdot \mu m$ to about to about $1 \times 10^{16}$ molecules per $cm^2 \cdot \mu m$.

Embodiments of the disclosed signaling conjugate can be made using the general procedure illustrated in Scheme 1. In particular disclosed embodiments, the conjugate is formed without an optional linker. For example, a carboxylic acid moiety of the chromophore may be coupled with a tyramine molecule or tyramine derivative by first converting the carboxylic acid to an activated ester and then forming an amide bond between the chromophore and the tyramine molecule or tyramine derivative. An exemplary method for making a signaling conjugate without a linker is illustrated below in Scheme 1.

Scheme 1

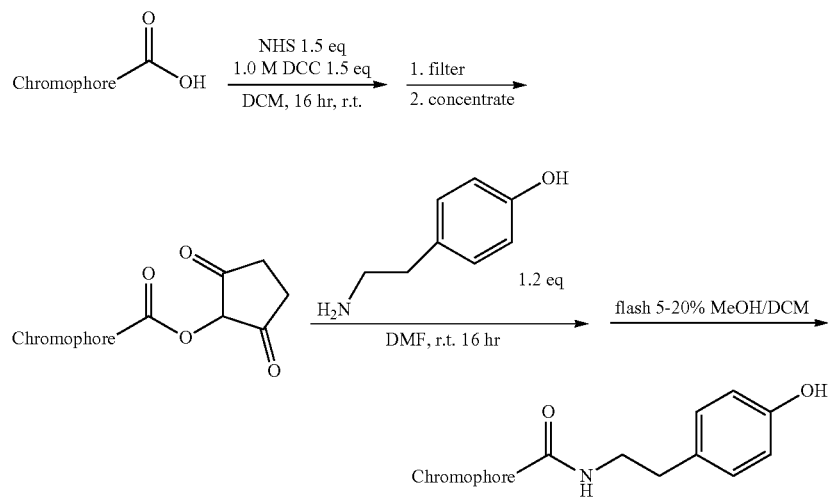

In embodiments wherein the linker is present, the carboxylic acid moiety of the chromophore may be coupled with an amine-terminated linker (e.g., an alkylene oxide) by first converting the carboxylic acid to an activated ester and then forming an amide bond between the chromophore and the amine-terminated linker. The remaining terminus of the linker may then be activated and subsequently coupled with a tyramine molecule or tyramine derivative. An exemplary method for making the signaling conjugate is provided below in Scheme 2.

Scheme 2
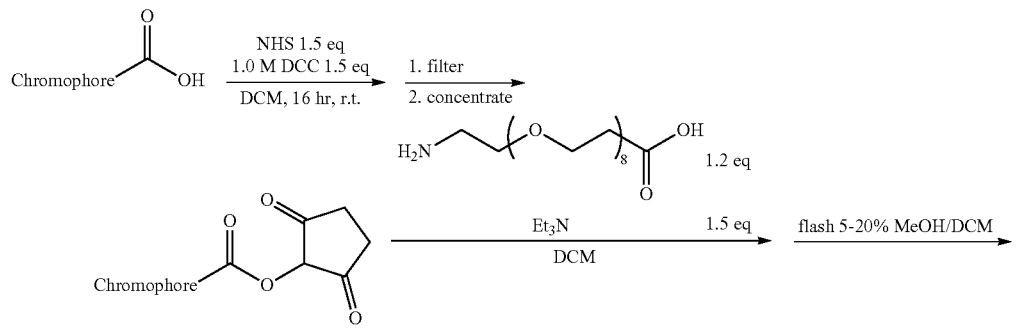
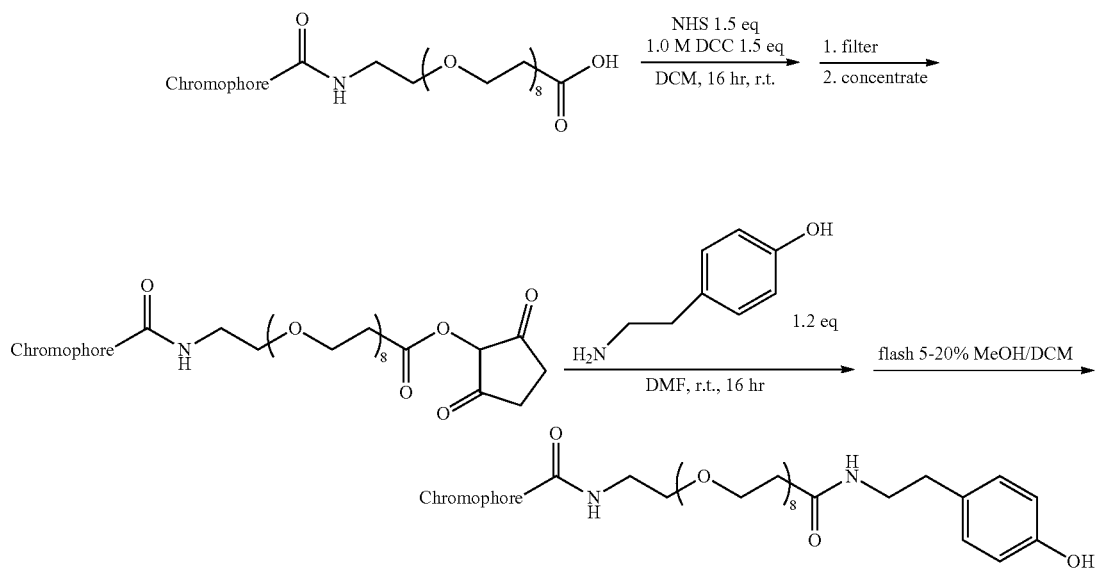
Exemplary signaling conjugates are provided below.
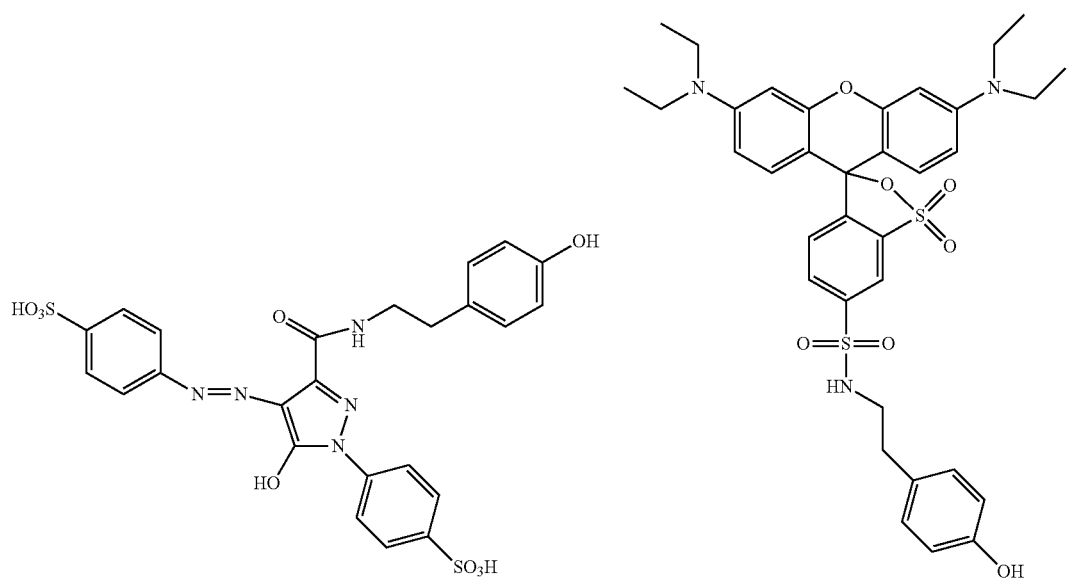

-continued
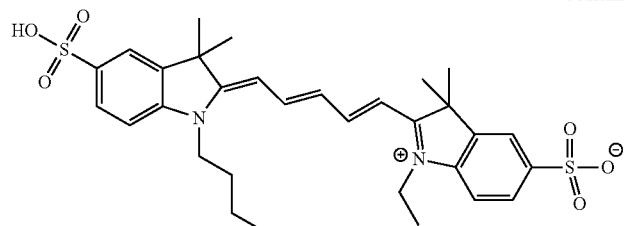
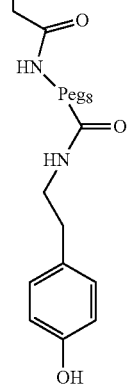
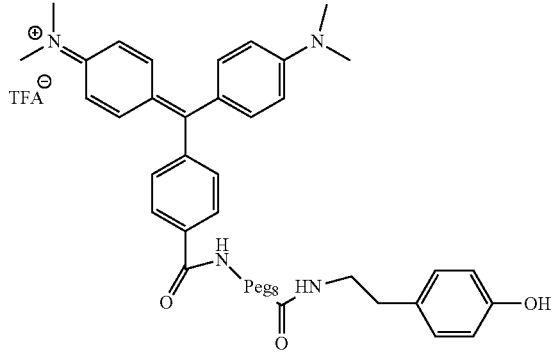
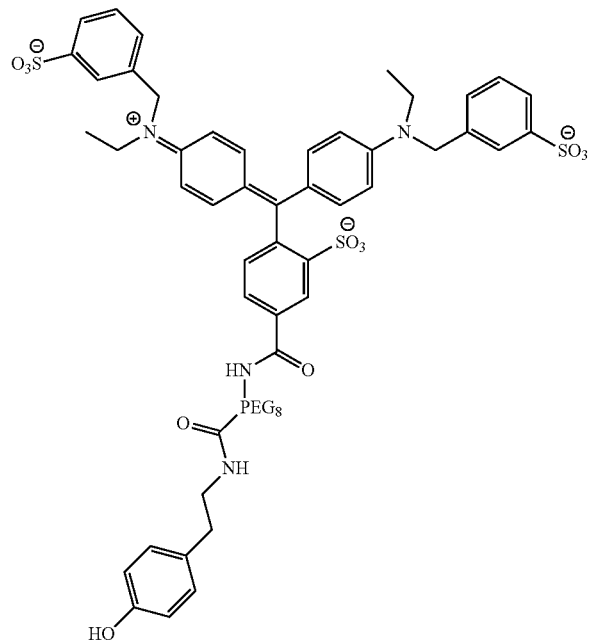
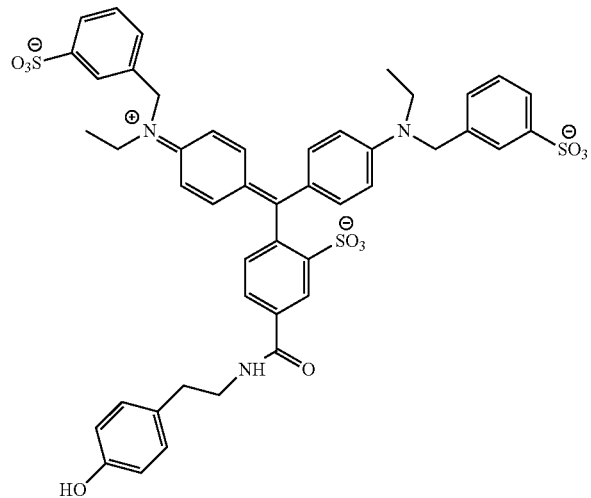

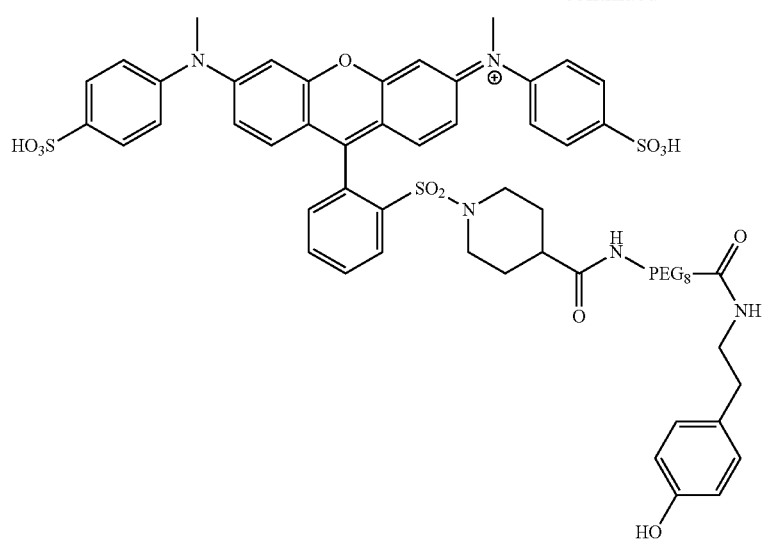
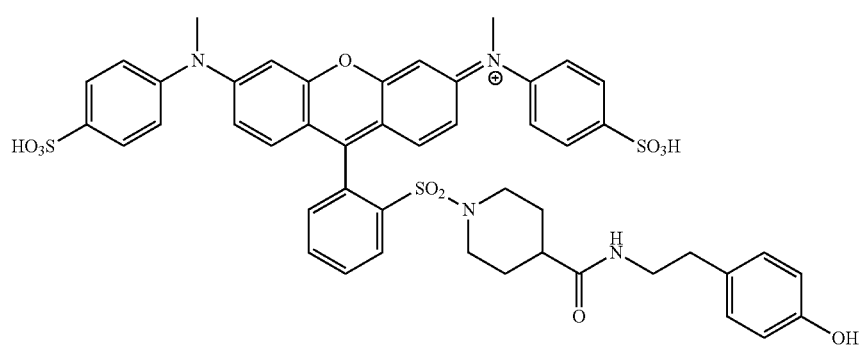
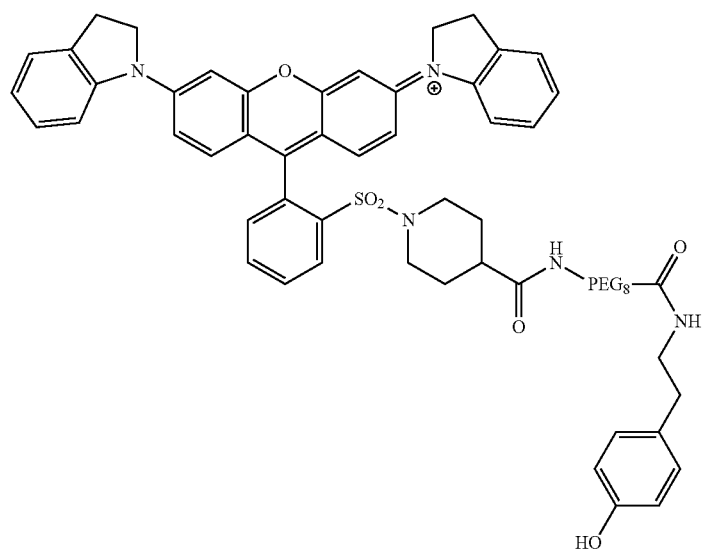

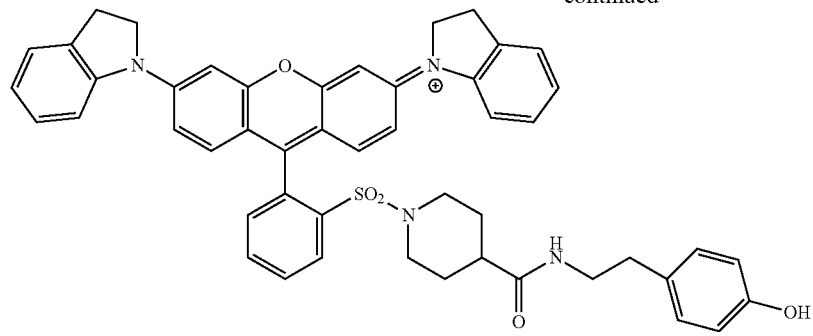
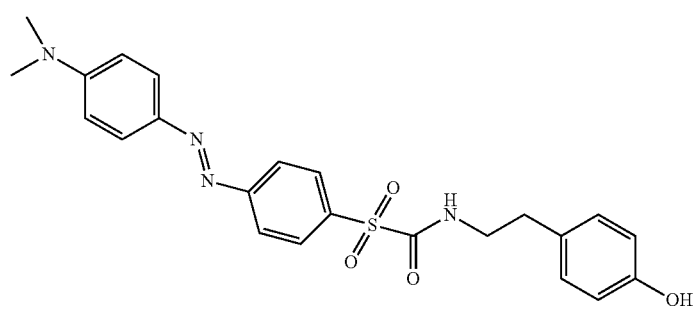
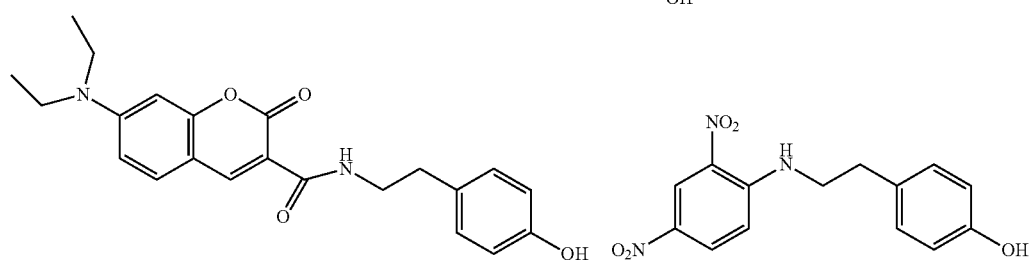
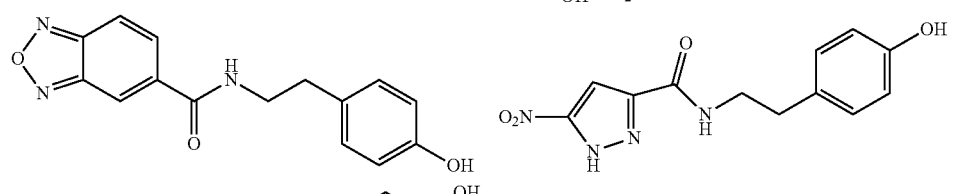
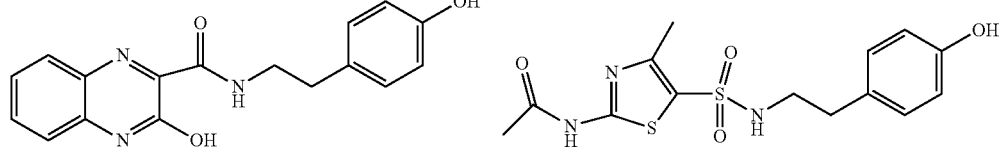
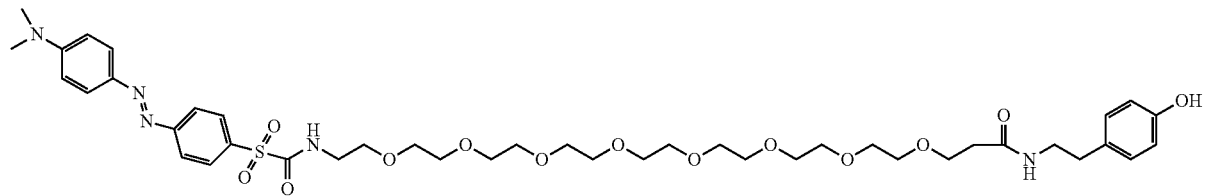
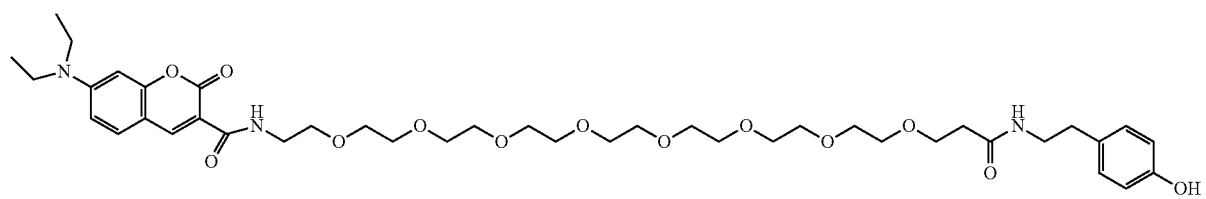

-continued
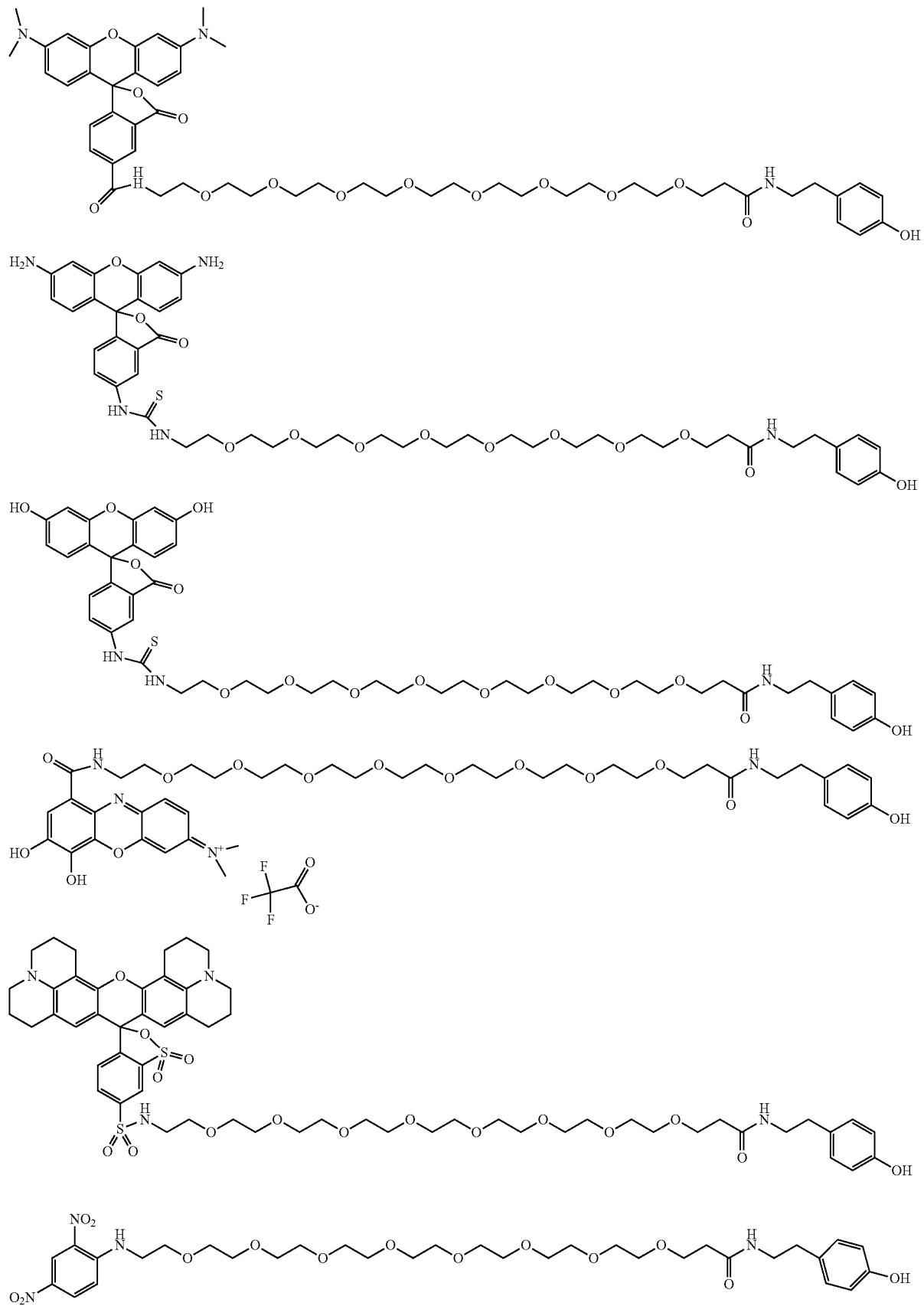

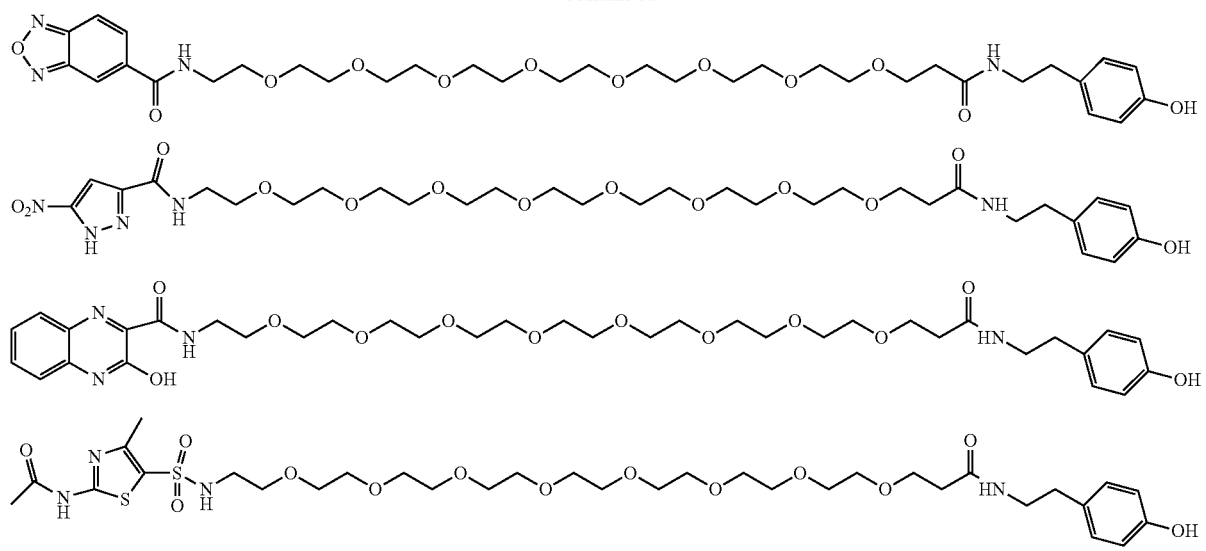
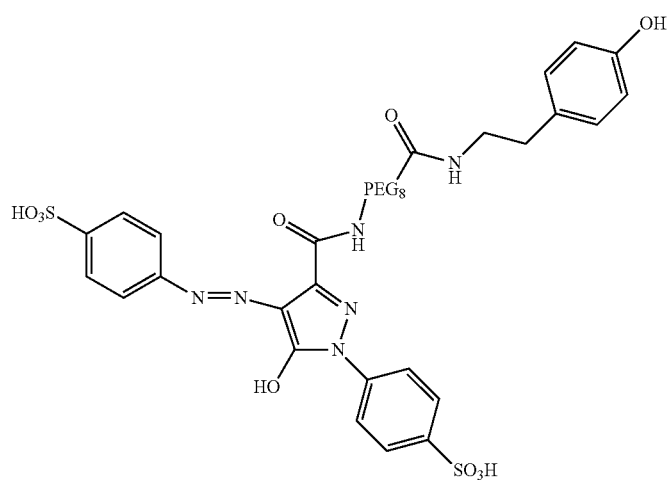
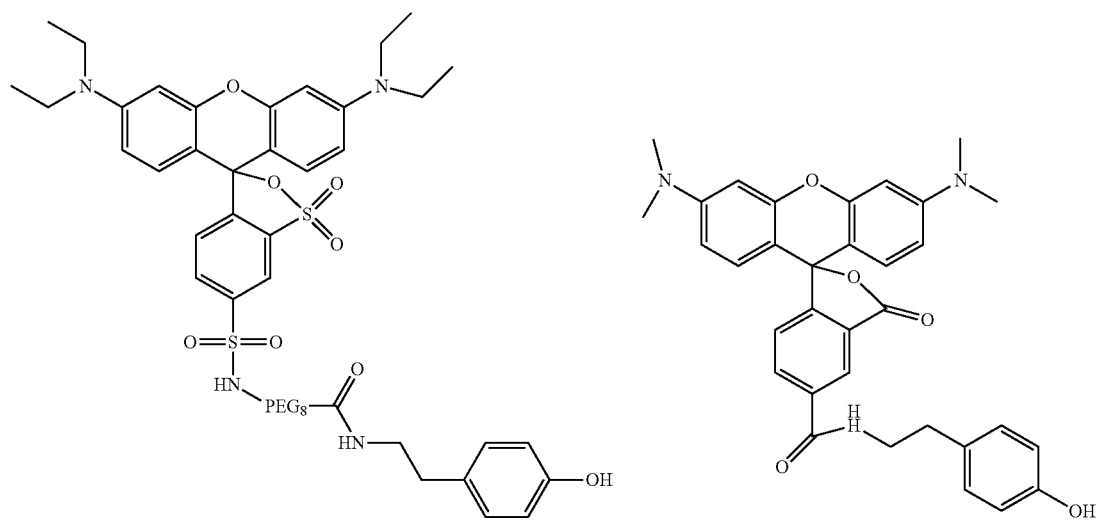

59
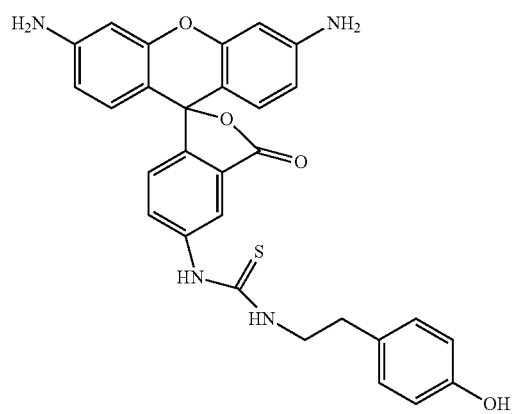
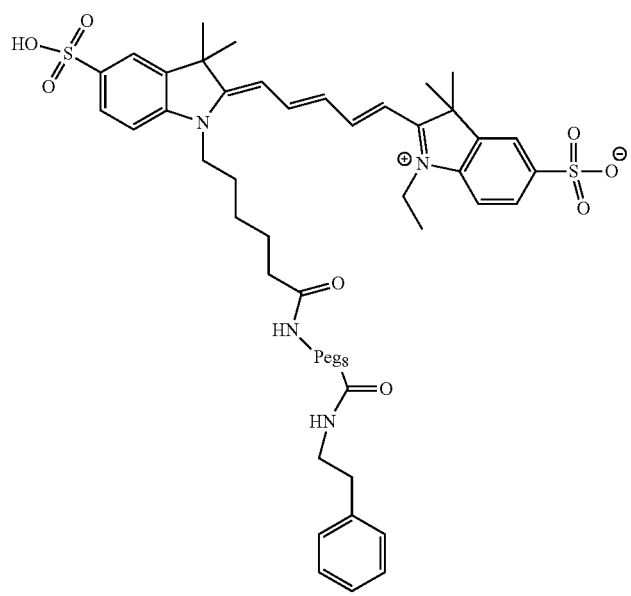
60
-continued
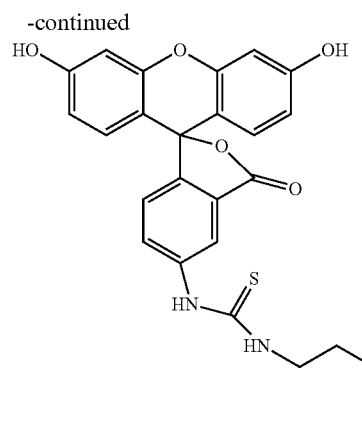
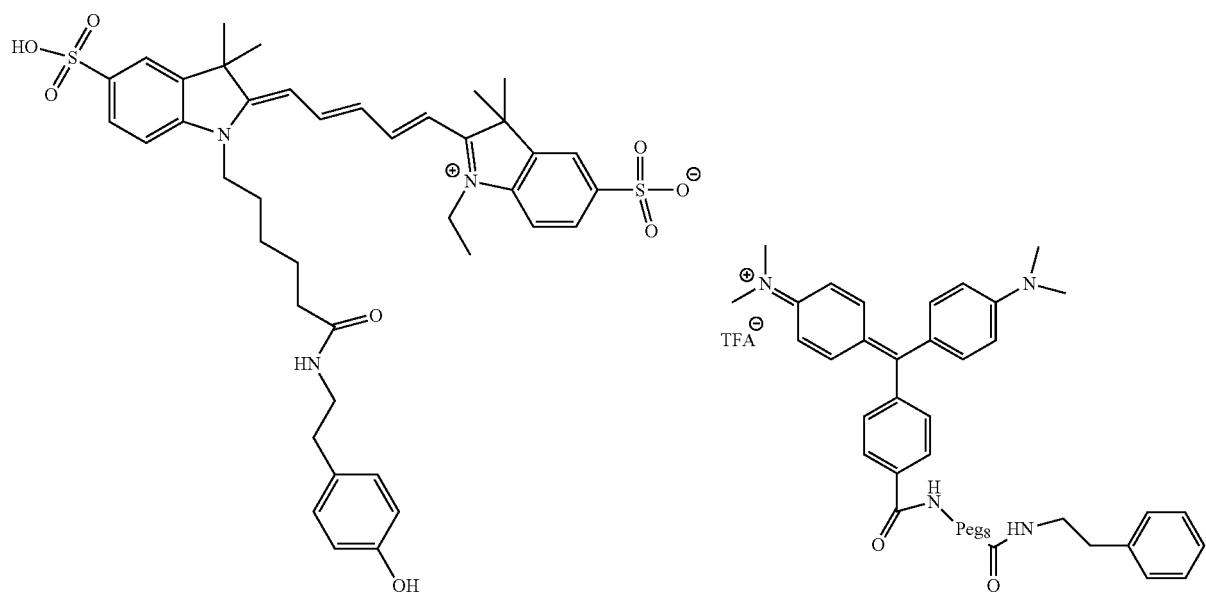

-continued

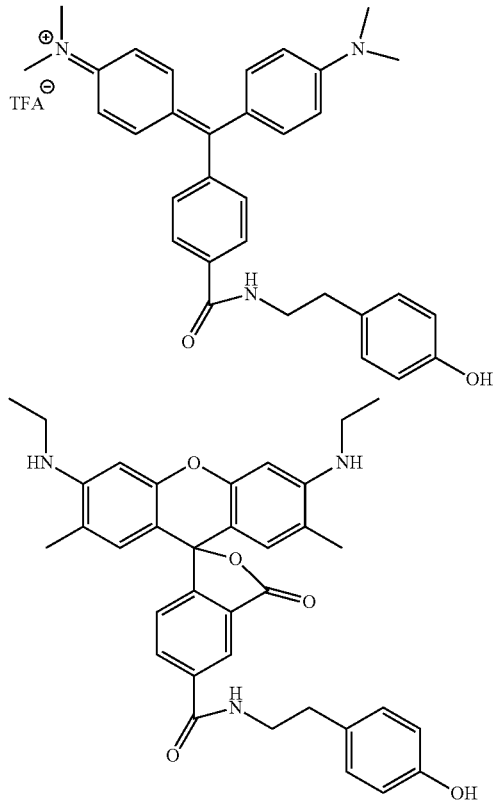
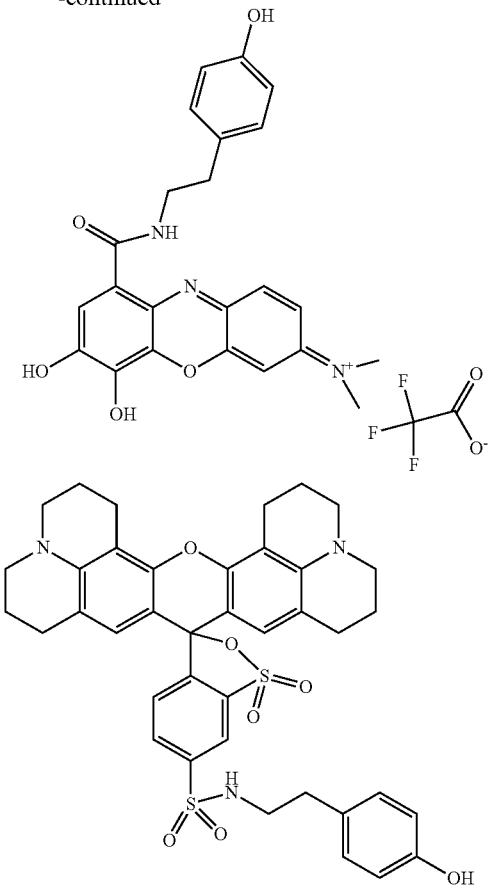

D. Amplifying Conjugates

Also disclosed herein are conjugates suitable for amplifying a signal obtained from carrying out the method disclosed herein. The amplifying conjugates typically comprise a latent reactive moiety, a detectable label, and an optional linker.

The detectable label of the amplifying conjugate may be any detectable label provided herein. In particular disclosed embodiments, the detectable label is a hapten, such as any of the haptens disclosed herein. U.S. Pat. No. 7,695,929 is hereby incorporated by reference herein in its entirety for disclosure related to the structures and synthetic approaches to making amplifying conjugates and their corresponding specific antibodies. In particular disclosed embodiments, a hapten having an electrophilic functional group (or having a functional group capable of being converted to an electrophilic functional group) is conjugated to the latent reactive moiety or to a linker, (e.g., an aliphatic or poly(alkylene oxide) linker). In certain embodiments, the hapten includes a carboxylic acid functional group, which is converted to an activated, electrophilic carbonyl-containing functional group, such as, but not limited to, an acyl halide, an ester (e.g., a N-hydroxysuccinimide ester), or an anhydride. The latent reactive moiety includes a nucleophilic functional group (e.g., amino, hydroxyl, thiol, or anions formed therefrom) capable of reacting with the hapten's activated electrophilic functional group. The hapten's electrophilic group can be coupled to the latent reactive moiety's nucleophilic group using organic coupling techniques known to a person of ordinary skill in the art of organic chemistry synthesis. In embodiments where the conjugate includes a linker, the linker typically has a nucleophilic functional group at one end and an electrophilic functional group at the other end. The linker's nucleophilic group can be coupled to the hapten's electrophilic group, and the linker's electrophilic group can be activated and coupled to the latent reactive moiety's nucleophilic group using organic coupling techniques known to a person of ordinary skill in the art of organic chemical synthesis.

In further illustrative embodiments, the signaling conjugate is used as an amplifying conjugate. The signaling conjugate can be used as an amplifying conjugate where the chromophore moiety is an effective labeling moiety. In illustrative embodiments, an antibody specific to a chromophore moiety enables that chromophore moiety to serve as a signaling and labeling conjugate. From another perspective, a hapten which possesses physical attributes, as disclosed herein, for effective chromophore moieties, may be used as both a chromophore moiety and as a hapten. There are particular benefits of using a signaling conjugate as an amplifying conjugate. In particular, the amplifying step would result in the deposition of significant, e.g., potentially detectable, amounts of the chromophore moiety. As such, the subsequent chromogenic detection could be stronger. Similarly, as described herein with respect to mixing chromogens from different classifications, a unique color could be generated using the overlap of absorbances from two or more chromophore moieties.

IV. Compositions

An illustrative composition according to the present disclosure comprises a biological sample and a plurality of signaling conjugates. In particular disclosed embodiments, the composition comprises a biological sample that comprises one or more enzyme-labeled targets. The enzyme used to label the target may originate from a labeling conjugate, such as an enzyme conjugate. The composition also may further comprise one or more detection probes. The plurality of signaling conjugates are as disclosed herein and are configured to provide a bright-field signal. The plurality of signaling conjugates are covalently bound proximally to or directly on the one or more targets. In particular disclosed embodiments, configured to provide a bright-field signal comprises choosing a particular chromogenic moiety for the signaling conjugate that is capable of absorbing about 5% or more of incident light. In particular disclosed embodiments, about 20% of the incident light may be absorbed.

In additional disclosed embodiments, the composition comprises a signaling conjugate that has been configured to provide the particular wavelength maxima disclosed herein for the chromogenic moieties of the signaling conjugates. Solely by way of example, the signaling conjugate is configured to provide a bright-field signal such that an absorbance peak having a $\lambda_{max}$ as is disclosed herein. Two different absorbance peaks also may be obtained by configuring different signaling conjugates to comprise different chromogenic moieties that have absorbance peaks of differing values, as disclosed herein. The composition also may comprise a plurality of signaling conjugates configured to provide a bright-field signal by being selected as having a particular FWHM value. Suitable FWHM values are disclosed herein. In other disclosed embodiments, at least a portion of the plurality of signaling conjugates has an average molar absorptivity selected from the particular values provided herein.

Particular disclosed embodiments of the composition also concern a plurality of signaling conjugates that have a particular solubility in water, such as those values provided herein. Also, the plurality of signaling conjugates also may be stable in an aqueous buffer solution for the period of time provided herein.

In particular disclosed embodiments, the composition comprises a plurality of signaling conjugates that are configured to impart an optically apparent color under bright-field illumination, such as red, orange, yellow, green, indigo, or violet. The optically apparent color may also be a mixture, such as that a first optically distinct color, a second optically distinct color, a third optically distinct color, a fourth optically distinct color, and even a fifth optically distinct color may be obtained and visualized.

The biological sample present in the disclosed composition can be a tissue or cytology sample as is disclosed herein. In particular disclosed embodiments, the biological sample may comprise two targets, a first target and a second target and the composition may further comprise a first detection probe that is specific for the first target and a second detection probe that is specific for the second target.

V. Kits

Also disclosed herein are embodiments of a kit comprising the signaling conjugate disclosed herein. In another embodiment, the kit includes a detection probe. In another embodiment, the kit includes a labeling conjugate. In another embodiment, the kit includes a amplifying conjugate and a secondary labeling conjugate. In another embodiment, the kit may further comprise a peroxide solution. In illustrative embodiments, the kit includes a detection probe. In illustrative embodiments, the reagents of the kit are packaged in containers configured for use on an automated slide staining platform. For example, the containers may be dispensers configured for use and a BENCHMARK Series automated slide stainer.

In illustrative embodiments, the kit includes a series of reagents contained in different containers configured to work together to perform a particular assay. In one embodiment, the kit includes a labeling conjugate in a buffer solution in a first container. The buffer solution is configured to maintain stability and to maintain the specific binding capability of the labeling conjugate while the reagent is stored in a refrigerated environment and as placed on the instrument. In another embodiment, the kit includes a signaling conjugate in an aqueous solution in a second container. In another embodiment, the kit includes a hydrogen peroxide solution in a third container for concomitant use on the sample with the signaling conjugate. In the second or third container, various enhancers (e.g., pyrimidine) may be found for increasing the efficiency by which the enzyme activates the latent reactive species into the reactive species. In a further embodiment, the kit includes an amplifying conjugate.

VI. Working Embodiments

General Procedures and Preparation

All ISH detection was performed on a Ventana Benchmark XT. DNP or DIG labeled (0.25 ng/ml final concentration) probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of the signaling conjugate (12.5 µM final concentration) was catalyzed by the addition of $H_2O_2$ (final percentage of 0.003%).

For assays utilizing an intermediate amplification step, the HRP conjugated anti-DNP or anti-DIG monoclonal antibody bound to the probe catalyzes the deposition of the amplifying conjugate (6.25 µM final concentration) by the addition of $H_2O_2$. The covalently bound amplifying conjugates in the tissue served as binding sites for monoclonal enzyme conjugates (2.5 ng/ml final concentration), and deposition of the signaling conjugate was catalyzed by the addition of the signaling conjugate (25 µM final concentration) and $H_2O_2$.

Signaling Conjugate Testing:

Each tyramide dye solution was tested for functionality at a range of micromolar to millimolar concentrations using an immunohistochemistry model against Her2 protein on formalin-fixed, paraffin embedded Calu-3, ZR75-1 and MCF-7 xenograft tissues mounted on Superfrost slides. Tissues were stained using a Benchmark XT Ventana automated slide staining instrument. Reagents necessary for the testing include VMSI Her2 (4B5) Primary Antibody VMSI product #790-2991, UltraMap anti-Rb HRP #760-4315, AmpMap Detection Kit with TSA #760-121, Hematoxylin II #790-2208 and Bluing Reagent #760-2037. Slides were de-paraffinized then antigen retrieved using cell conditioning 1 solution (#950-124), followed by the addition of the primary antibody for 16 minutes at 37° C., secondary antibody for 16 minutes at 37° C. and amplification using a single tyramide solution in TSA Diluent (#60900) or phosphate buffered saline with the addition of TSA-$H_2O_2$ (VMSI #760-4141) and incubating the reaction for 20 min. Each slide was counterstained with 4 minute incubation of Hematoxylin followed by a 4 minute incubation of Bluing solution and dehydrated using gradient alcohols and coverslipped.

Signaling Conjugate Evaluation:

Evaluation of the tyramide signal was visualized by use of a bright-field white light microscope. Each slide comprised of a positive control for Her2 protein of high expression (Calu-3 xenograft) an intermediate protein level control (ZR75-1 xenograft) and negative control for Her2 protein expression (MCF7 xenograft). Tyramide solutions that had specific staining were further tested for optimal dye intensity in the above assay before tissue staining was performed for nucleotide targets.

Signaling Conjugate Solubility and pH:

Solubility and pH proved to be variables unique to each tyramide dye. For instance, malachite green tyramide proved to be insoluble in the basic, pH 8.5, TSA Diluent (VMSI product #60900) but using a neutral pH of 7.4, phosphate buffered saline showed better solubility and no alteration of color properties. Any pH range less than 6.0 for malachite green tyramide turned the original green solution to a yellow color which was undesired. It was also found that for the tyramide dyes to be visualized in a bright-field white light manner, very high concentrations, on the order of 10 to 20 fold higher than used for fluorescence, needed to be achieved to generate enough colored material on the tissue slide. Stock solutions were formulated at millimolar or greater concentrations and the working solution was diluted in an aqueous buffer at optimal pH and solubility for each unique tyramide dye.

Example 1

Interrogation of gene expression in tissue sections using PCR or microarrays has been successfully used to classify patients' likelihood of tumor recurrence and identify those who may benefit from specific therapies. However, tissue specificity and cellular context, which improve the value of tissue based assays are lost during mRNA extraction. Moreover, false positive or negative results may be generated from the presence of "contaminating" non-tumor cells in the section. As such, there is a need for automated in situ hybridization assays which target mRNA (mRNA-ISH) that enables robust and reproducible evaluation of biomarker expression while preserving tissue context and specificity, as well as cell-cell relationships. Preservation of context and the ability to minimize cell-cell nucleic acid (RNA) contamination is desired for tests that interrogate cell clonality in which a cell expresses either one of two biomarkers but never both.

Methods for analyzing a sample for expression of an mRNA target are described. In illustrative embodiments the methods include contacting the sample with a labeled nucleic acid probe. Detection of the labeled probe creates a signal that corresponds to the expression of the mRNA target. This disclosure further describes compositions, kits, and methods for determination of cell clonality in human cancer samples. Specifically, B cell lymphomas resulting from clonal expansion of a specific B cell population expressing either KAPPA or LAMBDA mRNA are described.

In illustrative embodiments, a method for simultaneously analyzing a sample for expression of two mRNA targets includes contacting the sample with a mRNA target probe, wherein the mRNA target probe is labeled with a first hapten, contacting the sample with an internal mRNA standard probe, wherein the internal mRNA standard probe is labeled with a second hapten, contacting the sample with a first chromogenic detection reagent, contacting the sample with a second chromogenic detection reagent, detecting a second signal from the second chromogenic detection reagent, the second signal providing the expression of the internal mRNA standard, and detecting a first signal from the first chromogenic detection reagent, the first signal providing the expression of the mRNA target. In one embodiment, detecting the second signal below a predetermined signal level indicates the sample lacks integrity for analysis of the mRNA target.

Figure 21A:
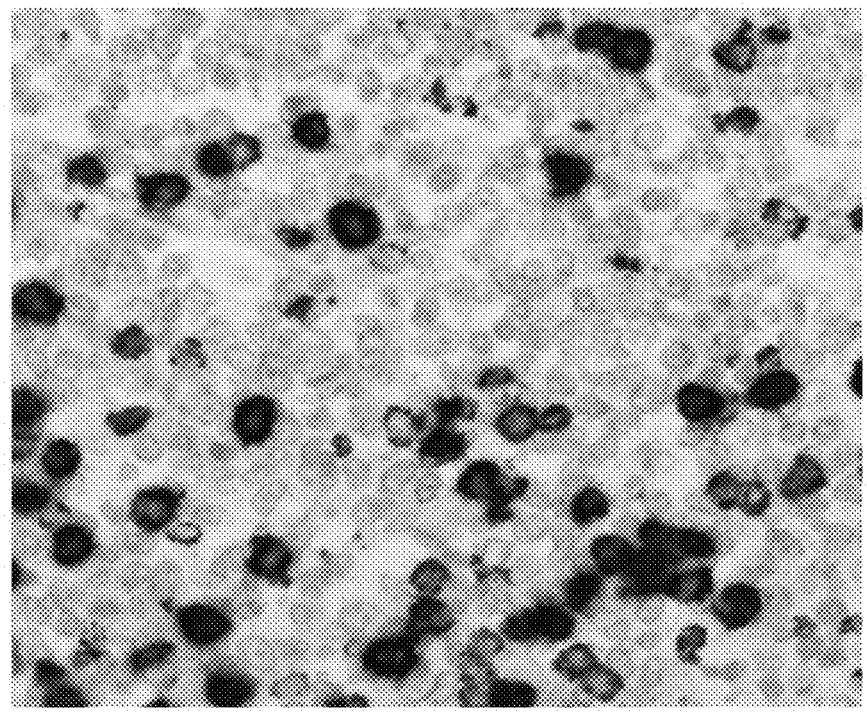
FIG. 21(A) is a 40× magnified view of a positive staining for KAPPA (brown) and LAMBDA (purple) mRNA.
Figure 21B:
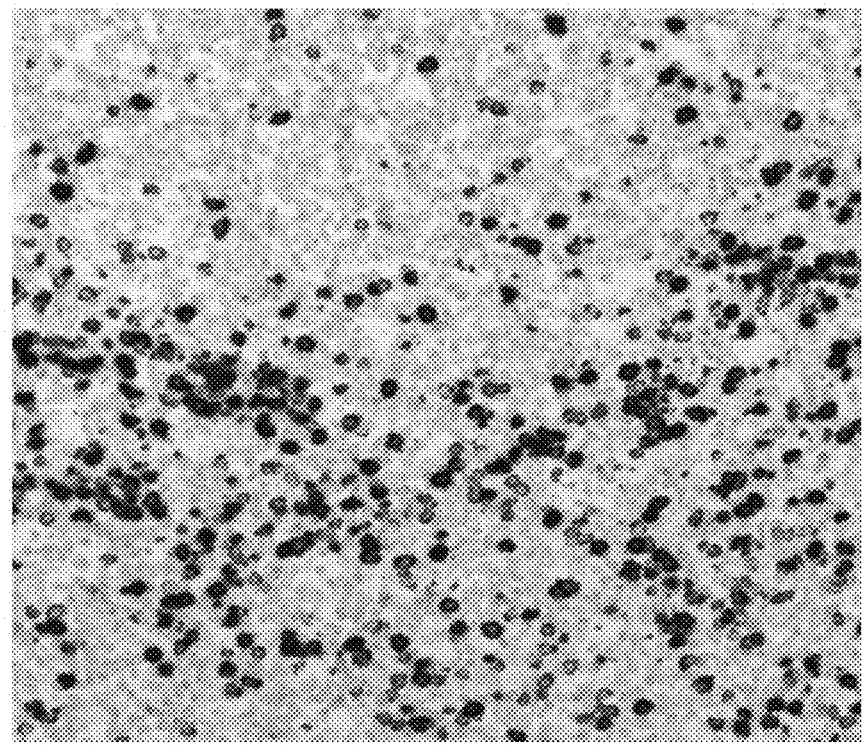
FIG. 21(B) is a 20× magnified view of the same.

Cancer results from uncontrolled growth of a cell population; this population may arise from a single mutant parent cell and, therefore, comprise a clonal population. An example of cancer derived from a clonal population is B-cell non-Hodgkin lymphomas (B-NHL) which arise from monoclonal proliferation of B cells. Clonal expansion of a specific B cell population can be detected by sole expression of either Kappa or Lambda light chain mRNA and protein as part of their B cell receptor antibody. One approach for the identification of monoclonal proliferation of B cells is chromogenic dual staining of Kappa and Lambda mRNA. Referring to FIG. 21(A-B), shown is an exemplary chromogenic dual staining approach.

Figure 22:
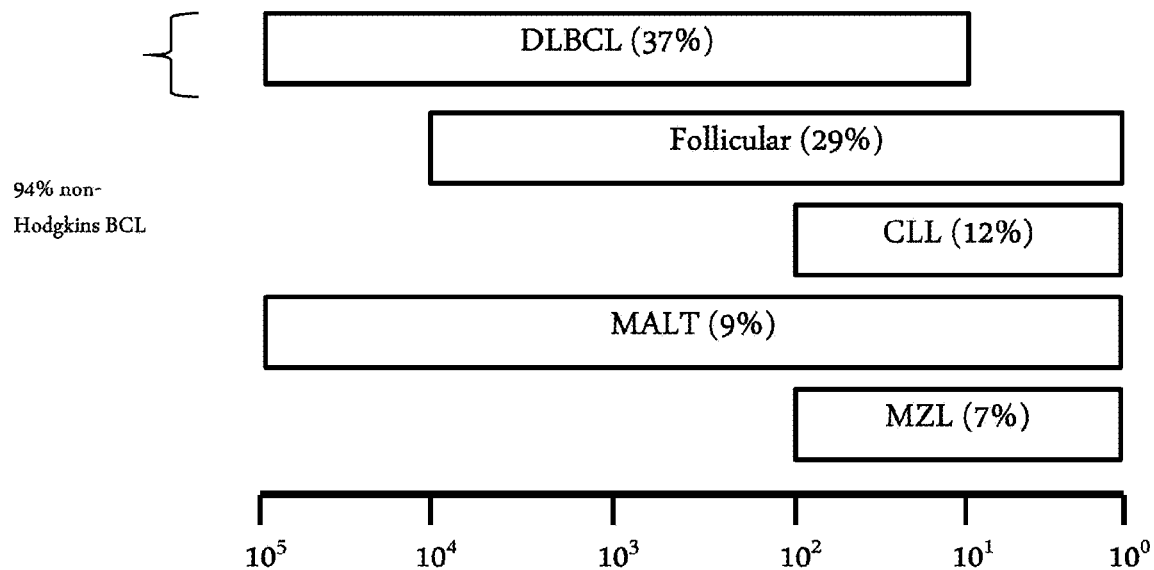
FIG. 22 is a schematic showing expected Kappa/Lambda copy numbers associated with different types of non-Hodgkins B-cell lymphomas.

Uniform expression of either light chain by malignant B cells enables differentiation of monoclonal B cell lymphomas from polyclonal Kappa and Lambda light chain expressing B cell populations that result during the normal immune response. Determination of light chain mRNA expression patterns is complicated by the copy number range of light chain mRNA and antibody protein expressed by B cell neoplasms derived from a variety of B cell stages (naïve and memory cells:10-100 copies per cell; plasma cells: ~100 thousand copies per cell). FIG. 22 is a schematic showing expected Kappa/Lambda copy numbers associated with different types of non-Hodgkins B-cell lymphomas.

While the present disclosure describes, in particularity, sensitive methods of analyzing a sample using KAPPA and LAMBDA mRNA in tissue samples expressing a range of light chain mRNA copy numbers, the approaches described herein are general and applicable to various useful biomarkers expressed uniquely by specific cell populations. The application of the disclosed technology to additional target and standard mRNA probes is within the scope of the present disclosure. By so applying the disclosed technology, the present method enables the interrogation of additional disease states and development of improved predictive and prognostic analyses for cancer patients as well as novel companion diagnostics. Furthermore, while the disclosure describes two-color mRNA ISH analysis, the scope of the present disclosure includes additional colors (e.g., three-color, four-color, etc.).

In illustrative embodiments, a method for determining cell clonality by analyzing a sample for expression of mRNA targets which are uniquely expressed by a specific cell population comprises contacting the sample with a first mRNA target probe, wherein the first mRNA target probe is labeled with a first hapten, contacting the sample with a second mRNA target probe, wherein the second mRNA target probe is labeled with a second hapten, contacting the sample with a first chromogenic detection reagent, contacting the sample with a second chromogenic detection reagent, detecting a first signal from the first chromogenic detection reagent, the first signal providing the expression of the first mRNA target, detecting a second signal from the second chromogenic detection reagent, the second signal providing the expression of the second mRNA target. In one embodiment, the first and the second signal indicate cell clonality for the sample. In another embodiment, the sample is a specific B cell population and the first and the second signal correspond to KAPPA or LAMBDA mRNA.

Probe Preparation and Formulation: Complementary (antisense) and non-complementary (sense) KAPPA and LAMBDA riboprobes were in vitro transcribed from PCR amplified dsDNA templates containing the T7 promoter. The nucleic acids were chemically labeled with different haptens (DIG, DNP) using linker arms prepared as directed by the manufacturer (Label IT® Technology, Minis Bio LLC, Madison, Wis.) and NHS-PEGS-haptens. Twenty-five nanograms of each probe was suspended in one mL of a hybridization buffer (Ribohybe™, VMSI #760-104) and placed into a dispenser (VMSI, #760-205) compatible with an automated slide staining instrument (VMSI, Discovery XT # F-DISXT-750000).

mRNA in situ hybridizations and detection: Samples were stained using mRNA ISH reagents (RiboMap, VMSI #760-102). Formalin-fixed, paraffin-embedded clinical tonsil and lymphoma tissue samples were mounted on slides (Super-Frost Ultra Plus®, Menzel-Gläser) were de-paraffined and antigen retrieved using cell conditioning reagents (Cell Conditioning 1, VMSI #950-124 and protease 3, VMSI #760-2020). Following retrieval, one drop (100 µL) of cocktailed hapten-labeled HER2 and ACTB anti-sense strand probes were dispensed onto the slide, denatured at 80° C. for 8 min, and hybridized at 65° C. for 6 hrs. Following hybridization, the slides were washed 3 times using a stringency buffer (0.1×SSC VMSI #950-110) at 75° C. for 8 minutes to remove non-specifically hybridized probe.

A two-tiered amplification procedure was used to amplify the signal for each of the binding events. Reagents included (1) an HRP-conjugated anti-hapten antibody to catalyze deposition of (2) a tyramide-hapten conjugate which was then bound by (3) a second HRP-conjugated anti-hapten antibody. The HRP was used to catalyze deposition of a chromophore and tyramide conjugate for LAMBDA and DAB for KAPPA.

Endogenous tissue peroxidase activity was inactivated by dispensing one drop an inhibitor (PO inhibitor, VMSI #760-4143) and incubating the reaction for 12 min. Following several washes, one drop of a second amplification blocking reagent (TSA block, VMSI #760-4142) was dispensed onto the slide and incubated 4 min. Next, a drop of HRP-conjugated anti-hapten monoclonal antibody solution was dispensed (2.5 µg/ml conjugate prepared in avidin diluent plus B5 blocker, VMSI #90040); the mixture was incubated for 28 min. Tyramide-mediated hapten amplification was accomplished by dispensing one drop of tyramide-hapten conjugate on the slide followed by one drop of a hydrogen peroxide solution (TSA-H2O2, VMSI #760-4141) and allowing the reaction to incubate for 20 min.

The procedure was repeated to direct tyramide-mediated amplification of the second hapten in the probe cocktail. Control studies demonstrated the use of three successive applications of the peroxide inhibitor to inactivate the previous HRP-conjugated anti-hapten antibody was preferred. Omission of the inactivation step resulted in co-localization of signals and non-specific mRNA signals. The LAMBDA amplified hapten was then sequentially detected using a similar amplification strategy which included three applications of the peroxide inhibitor, application of a cognate anti-hapten monoclonal antibody and application of a tyramide-chromophore conjugate and peroxide. The hapten designating KAPPA was detecting using a DAB detection reagent (OptiView DAB, VMSI #760-700).

Tissue nuclei were then stained using a hematoxylin solution and bluing reagent (VMSI, Hematoxylin II, #790-2208 Bluing Reagent, #760-2037). Slides were then dehydrated using gradient alcohols and coverslipped.

Figures 23A, 23B:
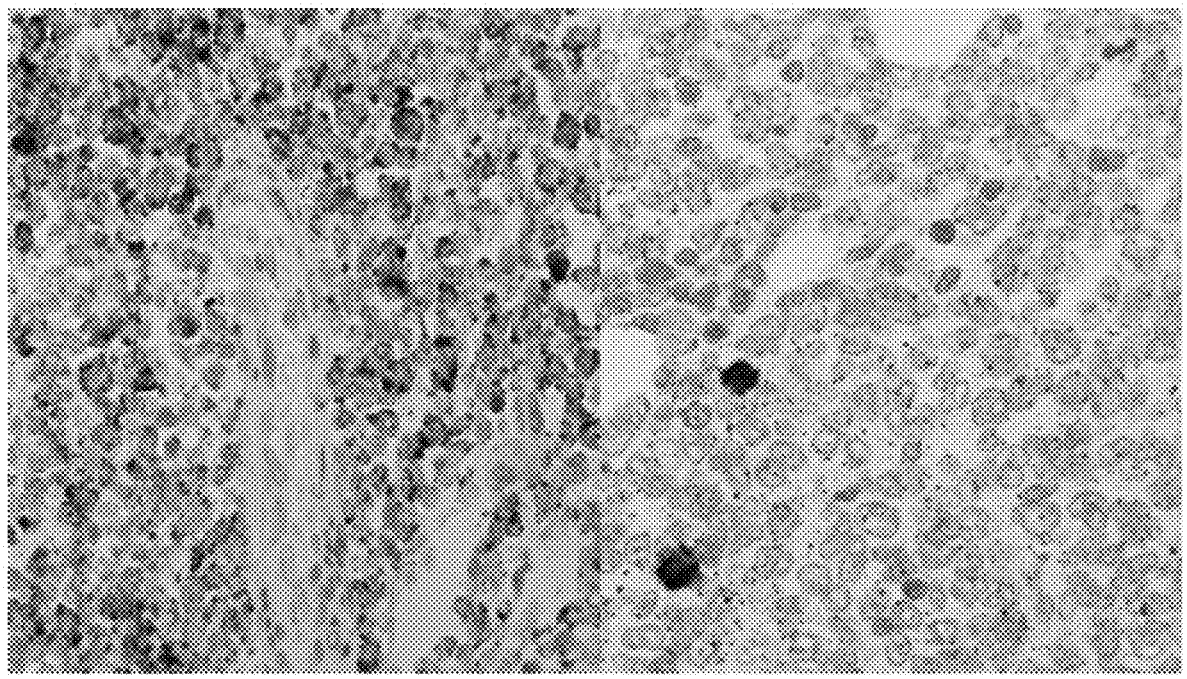
FIG. 23(A) is a first lymphoma tissue sample showing a dual staining of KAPPA mRNA (brown) and LAMBDA mRNA (purple, minimally observed), showing very few cells expressing LAMBDA mRNA, and FIG. 23(B) a second lymphoma tissue sample showing a dual staining for KAPPA mRNA (brown, minimally observed) and LAMBDA mRNA (purple), showing very few cells expressing KAPPA mRNA.

Exemplary photomicrographs of tissue samples treated according the above procedures are shown in FIGS. 23(A-B), which are photomicrographs of (A) a first lymphoma tissue sample showing a dual staining of KAPPA mRNA (brown) and LAMBDA mRNA (purple, minimally observed), showing very few cells expressing LAMBDA mRNA and (B) a second lymphoma tissue sample showing a dual staining for KAPPA mRNA (brown, minimally observed) and LAMBDA mRNA (purple), showing very few cells expressing KAPPA mRNA. The nearly monoclonal populations observed are indicative of a cancer.

Figure 24A:
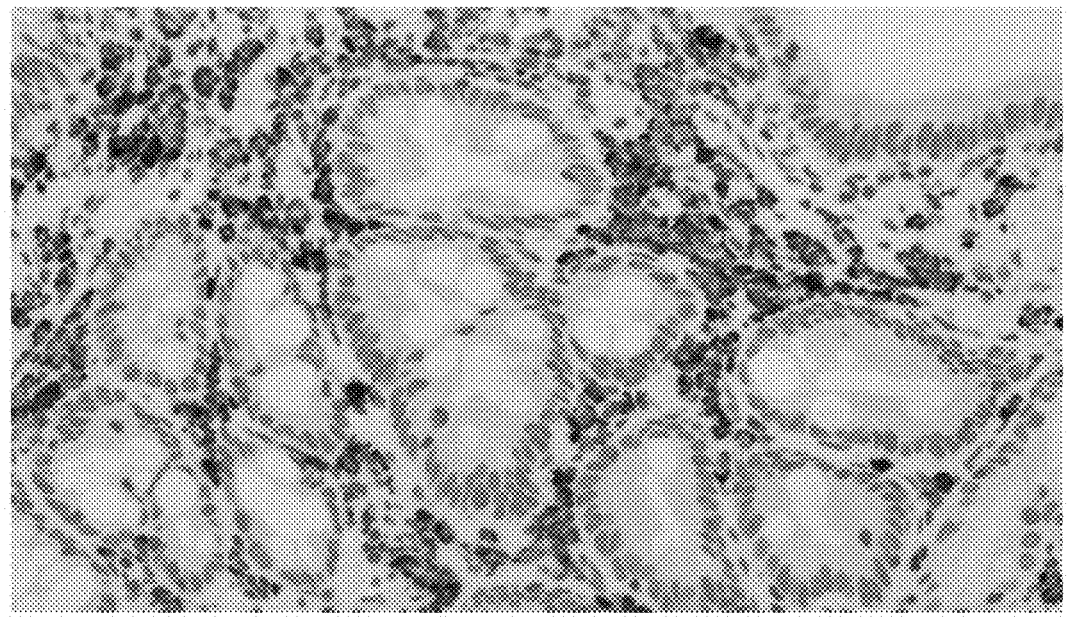
FIGS. 24(A-B) are photomicrographs which demonstrate dual chromogenic mRNA ISH for a sample that would confound molecular methods of diagnosis.
Figure 24B:
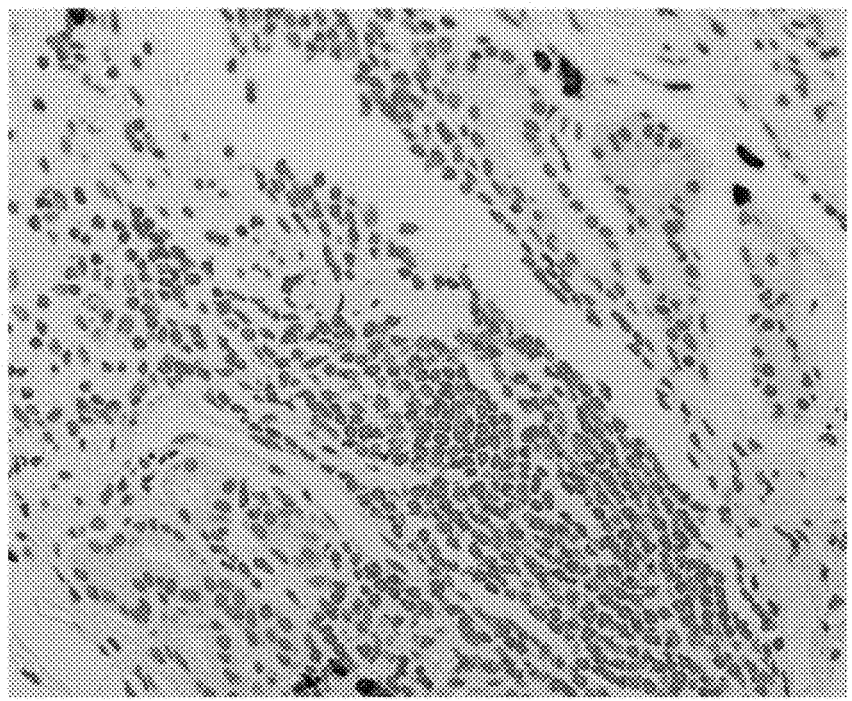

FIG. 24(A-B) are photomicrographs of a dual-color mRNA-ISH KAPPA (brown) and LAMBDA (purple) assay for a tissue. In FIG. 24(A), the polyclonal B cell population is clearly stained with either purple or brown indicating the cells are expressing either LAMBDA or KAPPA mRNA. The sample exhibits high levels of expression for both KAPPA and LAMBDA mRNA. FIG. 24(B) shows a portion of the sample exhibiting a monoclonal cellular population indicative of cancer. The high expressions of KAPPA and LAMBDA mRNA expression in the sample, as a whole, would confound a molecular analysis of the sample as the difference between the KAPPA and LAMBDA mRNA expression is minimal. However, because the expression of KAPPA and LAMBDA mRNA is visualized through a histopathological analysis, the dual-staining approach described herein enables detection of the monoclonal population.

Two-color mRNA-ISH is technically feasible for a large majority of samples as a replacement or as a complement to existing and yet undiscovered ISH and IHC analyses. Differentiation of clonal lymphoma samples from non-clonal reactive processes was empowered by the two-color detection system. Moreover, the assay's utility for sensitive detection and discrimination of low copy mRNA targets in various lymphoma cases was demonstrated. Collectively, these observations indicate that the approach is useful for determination of cell clonality using mRNA biomarkers expressed uniquely by a specific population.

Furthermore, the use of chromophore and tyramide conjugates enables a new class of two-color chromogenic analysis. The conjugates are amenable to multiplexing due to their narrow band-widths (e.g., FWHM). The conjugates are stable as reagents for extended periods of time. The conjugates are covalently bound to the tissue as opposed to traditional chromogen systems which precipitate, thus the conjugates are not adversely affected by post-staining processing or subsequent staining steps. The dramatic amplification of the target enables bright-field detection and significant concentrations of the chromophore localized proximally to the target. These high concentrations overcome many concerns associated with photo-bleaching, especially as compared to the concentrations appropriate for fluorescent detection. Use of the new chromophore and tyramide conjugates has enabled an important new class of analytical methodologies—chromogenic mRNA ISH.

Example 2

Obstacles to mRNA-ISH assay utility in biological samples (e.g., formalin-fixed paraffin embedded tissues, "FFPE tissues") include variation in sample preparation (e.g., tissue fixation) which influences sample mRNA integrity/accessibility and assay performance. One aspect of the present disclosure is that automated mRNA-ISH assays for FFPE samples have been developed which enable simultaneous analysis of biomarker expression and an internal control gene expression to monitor assay performance and sample integrity. According to one specific example, clinical breast cancer FFPE tissue blocks were characterized for HER2 gene copy number and Her2 protein expression using INFORM HER2 Dual ISH and IHC assays (Ventana Medical Systems, Inc.), respectively. HER2 mRNA expression levels relative to ACTB ((3-actin) were determined using qPCR according to known methods. Results of the gene copy, protein expression, and qPCR analyses were compared to results obtained through mRNA-ISH detection of HER2 and ACTB mRNA in FFPE samples (FIG. 27). Varied tissue retrieval conditions were used to test the utility of an internal mRNA standard to identify samples for which mRNA integrity is compromised.

While the present disclosure describes, in particularity, methods of analyzing a sample using HER2 and ACTB mRNA, the approaches described herein are general and applicable to various useful biomarkers. The application of the disclosed technology to additional target and standard mRNA probes is within the scope of the present disclosure.

In illustrative embodiments, a method for analyzing a sample for expression of an mRNA target and an internal mRNA standard includes contacting the sample with a mRNA target probe, wherein the mRNA target probe is labeled with a first hapten, contacting the sample with an internal mRNA standard probe, wherein the internal mRNA standard probe is labeled with a second hapten, contacting the sample with a first signaling conjugate, contacting the sample with a second signaling conjugate, detecting a second signal from the second signaling conjugate, the second signal providing the expression of the internal mRNA standard, and detecting a first signal from the first signaling conjugate, the first signal providing the expression of the mRNA target. In one embodiment, detecting the second signal below a predetermined signal level indicates the sample lacks suitability for analysis of the mRNA target. In another embodiment, detecting the first signal includes determining the expression of the mRNA semi-quantitatively.

In illustrative embodiments, contacting the sample with the first signaling conjugate includes contacting the sample with a first anti-hapten antibody and enzyme conjugate, the first anti-hapten antibody and enzyme conjugate being specific to the first hapten, contacting the sample with a third hapten and tyramide derivative conjugate, contacting the sample with a third anti-hapten antibody and enzyme conjugate, the third anti-hapten antibody and enzyme conjugate being specific to the third hapten, and contacting the sample with a first chromogen. In further illustrative embodiments, contacting the sample with the second signaling conjugate includes contacting the sample with a second anti-hapten antibody and enzyme conjugate, the second anti-hapten antibody and enzyme conjugate being specific to the second hapten, contacting the sample with a fourth hapten and tyramide conjugate, contacting the sample with a fourth anti-hapten antibody and enzyme conjugate, the fourth anti-hapten antibody being specific to the fourth hapten, and contacting the sample with a second chromogen. In one embodiment, the first chromogen is selected from the group consisting of DAB, AEC, CN, BCIP/NBT, fast red, fast blue, fuchsin, NBT, and ALK GOLD. In another embodiment, the second chromogen comprises a chromophore and tyramide conjugate. In one embodiment, the second chromogen is selected from the group consisting of DAB, AEC, CN, BCIP/NBT, fast red, fast blue, fuchsin, NBT, and ALK GOLD. In yet another embodiment, the first chromogen comprises a chromophore and tyramide conjugate.

Probe Preparation and Formulation: Complementary (antisense) and non-complementary (sense) HER2 and ACTB riboprobes were in vitro transcribed from PCR amplified dsDNA templates containing the T7 promoter. The nucleic acids were chemically labeled with different haptens (DIG, DNP) using linker arms prepared as directed by the manufacturer (Label IT® Technology, Mirus Bio LLC, Madison, Wis.) and NHS-PEGS-haptens. Twenty-five nanograms of each probe was suspended in one mL of a hybridization buffer (Ribohybe™, VMSI #760-104) and placed into a dispenser (VMSI, #760-205) compatible with an automated slide staining instrument (VMSI, Discovery XT # F-DISXT-750000).

mRNA in situ hybridizations and detection: Samples were stained using mRNA ISH reagents (RiboMap, VMSI #760-102). Formalin-fixed, paraffin-embedded clinical breast tissue samples were mounted on slides (SuperFrost Ultra Plus®, Menzel-Glaser) were de-paraffined and antigen retrieved using cell conditioning reagents (Cell Conditioning 1, VMSI #950-124 and protease 3, VMSI #760-2020). Following retrieval, one drop (100 µL) of cocktailed hapten-labeled HER2 and ACTB anti-sense strand probes were dispensed onto the slide, denatured at 80° C. for 8 minutes, and hybridized at 65° C. for 6 hrs. Following hybridization, the slides were washed 3 times using a stringency buffer (0.1×SSC VMSI #950-110) at 75° C. for 8 minutes to remove non-specifically hybridized probe.

A two-tiered amplification procedure was used to amplify the signal for each of the binding events. Reagents included (1) an HRP-conjugated anti-hapten antibody to catalyze deposition of (2) a tyramide-hapten conjugate which was then bound by (3) a second HRP-conjugated anti-hapten antibody. The HRP was used to catalyze deposition of a chromophore and tyramide conjugate for ACTB and DAB for HER2.

Endogenous tissue peroxidase activity was inactivated by dispensing one drop an inhibitor (PO inhibitor, VMSI #760-4143) and incubating the reaction for 12 min. Following several washes, one drop of a second amplification blocking reagent (TSA block, VMSI #760-4142) was dispensed onto the slide and incubated 4 min. Next, a drop of HRP-conjugated anti-hapten monoclonal antibody solution was dispensed (2.5 µg/ml conjugate prepared in avidin diluent plus B5 blocker, VMSI #90040); the mixture was incubated for 28 min. Tyramide-mediated hapten amplification was accomplished by dispensing one drop of tyramide-hapten conjugate on the slide followed by one drop of a hydrogen peroxide solution (TSA-H2O2, VMSI #760-4141) and allowing the reaction to incubate for 20 min.

The procedure was repeated to direct tyramide-mediated amplification of the second hapten in the probe cocktail. Control studies demonstrated the use of three successive applications of the peroxide inhibitor to inactivate the previous HRP-conjugated anti-hapten antibody was preferred. Omission of the inactivation step resulted in co-localization of signals and non-specific mRNA signals. The ACTB amplified hapten was then sequentially detected using a similar amplification strategy which included three applications of the peroxide inhibitor, application of a cognate anti-hapten monoclonal antibody and application of a tyramide-chromophore conjugate and peroxide. The hapten designating HER2 was detecting using a DAB detection reagent (OptiView DAB, VMSI #760-700).

Tissue nuclei were then stained using a hematoxylin solution and bluing reagent (VMSI, Hematoxylin II, #790-2208 Bluing Reagent, #760-2037). Slides were then dehydrated using gradient alcohols and coverslipped.

Figure 25A:
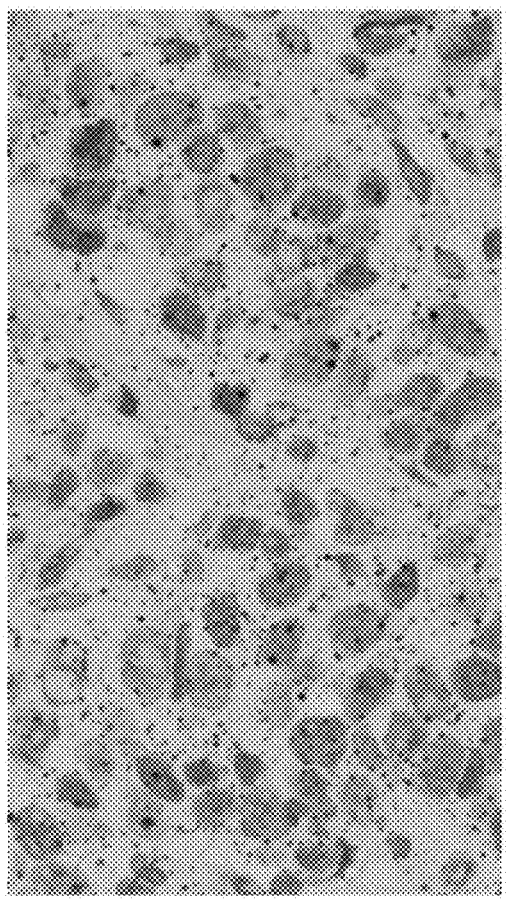
FIG. 25(A) is a negative staining for ACTB mRNA.
Figure 25B:
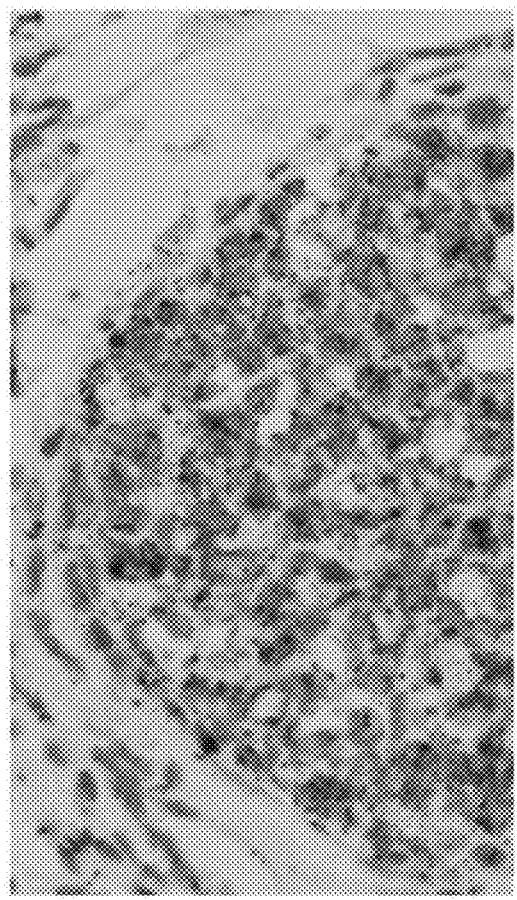
FIG. 25(B) is positive staining for ACTB mRNA.
Figure 26A:
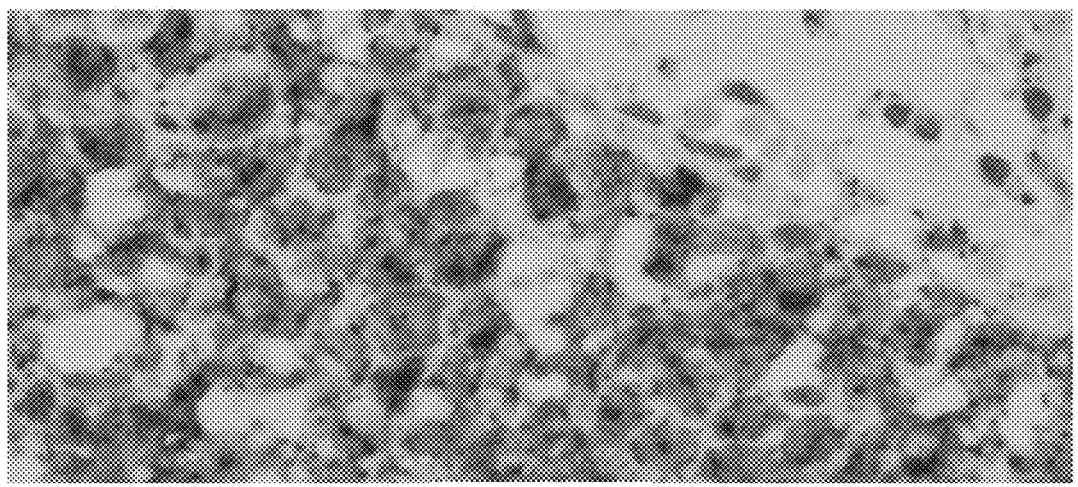
FIG. 26(A) is a negative (0+) staining for HER2 mRNA.
Figure 26B:
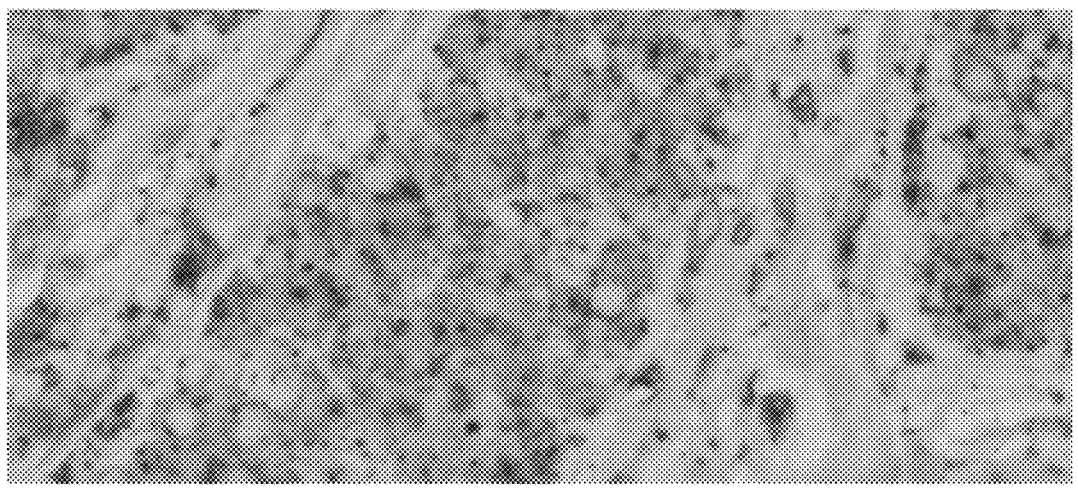
FIG. 26(B) is a positive (½+) staining for HER2 mRNA.
Figure 26C:
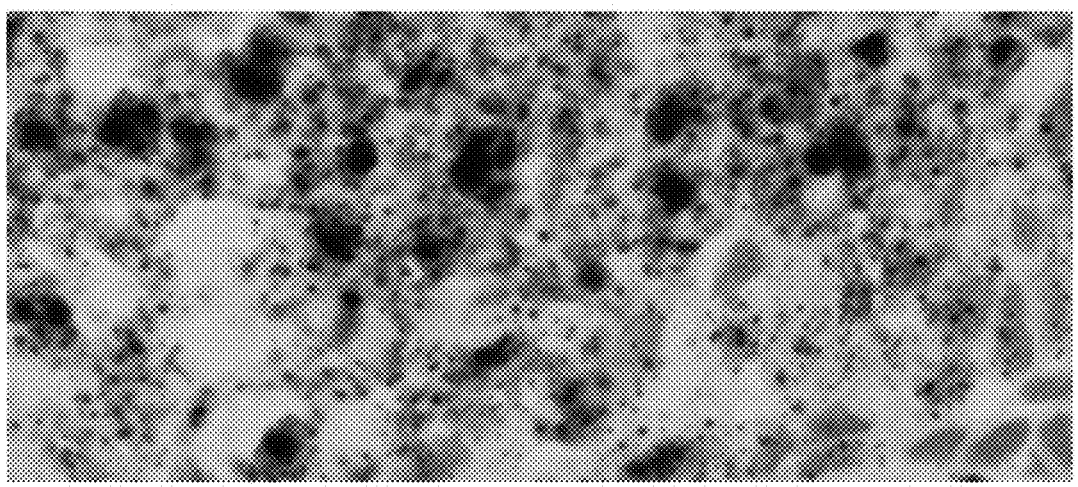
FIG. 26(C) is a positive (3+) staining for HER2 mRNA.

Exemplary photomicrographs of tissue samples treated according the above procedures are shown in FIGS. 25(A-B). FIG. 25(A) shows a photomicrograph of (A) an ACTB analysis performed on a tissue sample fixed for 4 hours and (B) a tissue sample fixed for 24 hours. The first sample (FIG. 25(A)) includes weak ACTB staining which was classified as lacking sample integrity due to the improper fixing conditions. The second sample (FIG. 25(B)) includes strong ACTB staining and was classified as suitable for HER2 evaluation (FIGS. 25(A-B) include only a single color). FIGS. 26(A-C) show examples of clinical tissue sample exhibiting two-color mRNA ISH staining of ACTB mRNA and (A) negative (0+) HER2 mRNA ISH staining, (B) positive (½+) HER2 mRNA ISH staining, and (C) positive (3+) HER2 mRNA ISH staining. FIG. 28 is data from 20 tissue blocks including the results of HER2 ISH analysis (VENTANA INFORM HER2 Dual ISH assay, VMSI), HER2 IHC analysis (PATHWAY HER-2/neu, OptiView DAB, VMSI), and HER2 mRNA two-color ISH.

It was discovered that mRNA ACTB signals were influenced by assay pre-hybridization treatment and, therefore, useful for evaluation of assay performance and determination of appropriate assay conditions. HER2 mRNA-ISH signals predominantly correlated with copy number and protein expression in samples with concordant copy number and protein levels; in discordant samples (normal copy number with increased protein expression or increased copy number with little detectable protein expression) HER2 mRNA-ISH signals were largely elevated. Collectively, these observations suggest that the mRNA-ISH assay may serve as a companion assay to clarify samples harboring discordant HER2 gene copy number and protein levels. Moreover, these studies demonstrate utility of an accessible bright-field assay platform for gene expression that preserves cellular context in FFPE tissues.

From the above and the data included in FIG. 4, the following conclusions were drawn. Two-color mRNA-ISH is technically feasible for a large majority of samples as a replacement or as a complement to existing and yet undiscovered ISH and IHC analyses. The inclusion of an ACTB internal control, or a like internal control, enables identification of tissues not suitable for analysis and/or assay failures. Accordingly, the present disclosure describes new approaches to diminishing false negative rates due to unsuitability of the sample or from assay failure. HER2 mRNA-ISH signals may be classified into three expression patterns largely concordant with established conventional Her2 protein levels. Where HER2 DNA-ISH and IHC are discordant in 10% and 5% of samples, respectively. Gene expression analyses (qPCR and mRNA-ISH) correlate with either DNA copy number or protein levels in discordant samples. Two-color bright-field HER2/ACTB mRNA-ISH assay may serve as a companion test to clarify discordant samples.

Furthermore, the use of chromophore and tyramide conjugates enables a new class of two-color chromogenic analysis. The conjugates are amenable to multiplexing due to their narrow band-widths (e.g., FWHM). The conjugates are stable as reagents for extended periods of time. The conjugates are covalently bound to the tissue as opposed to traditional chromogen systems which precipitate, thus the conjugates are not adversely affected by post-staining processing or subsequent staining steps. The dramatic amplification of the target enables bright-field detection and significant concentrations of the chromophore localized proximally to the target. These high concentrations overcome many concerns associated with photo-bleaching, especially as compared to the concentrations appropriate for fluorescent detection. Use of the new chromophore and tyramide conjugates has enabled an important new class of analytical methodologies—chromogenic mRNA ISH.

Example 3

Figures 28A, 28B:
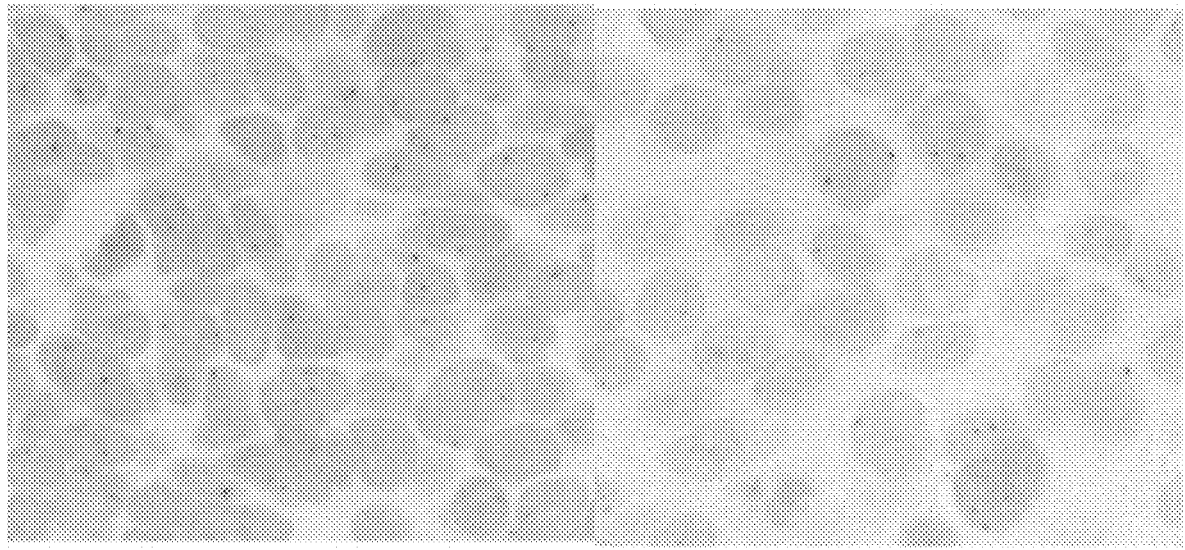
FIG. 28(A) is a photomicrograph at 40× magnification and FIG. 28(B) is a photomicrograph of a separate area at 63× magnification.

DNP or DIG labeled (0.25 ng/ml final concentration) PTEN DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Rhodamine-tyramide (12.5 µM final concentration) was catalyzed by the addition of $H_2O_2$ (final percentage of 0.003%). FIGS. 28(A-B) show results obtained from using this embodiment to detect a PTEN DNA ISH probe in VCAP xenograft tumor cells. FIG. 28(A) is an image taken at 40× magnification, and FIG. 28(B) is an image of a separate area of the tissue taken at 63× magnification.

Example 4

DNP or DIG labeled (0.25 ng/ml final concentration) ERG5' DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Rhodamine-tyramide (12.5 µM final concentration) was catalyzed by the addition of $H_2O_2$ (final percentage of 0.003%).

Additionally, an HRP conjugated anti-DNP or anti-DIG monoclonal antibody bound to the probe is used to catalyze tyramide-BF deposition (6.25 µM final concentration) by the addition of $H_2O_2$. The covalently bound amplifying conjugate in the tissue served as binding sites for monoclonal anti-BF antibodies conjugated to HRP (2.5 ng/ml final concentration), and deposition of the signaling conjugate was catalyzed by the addition of the signaling conjugate (25 µM final concentration) and $H_2O_2$.

Figures 29, 30:
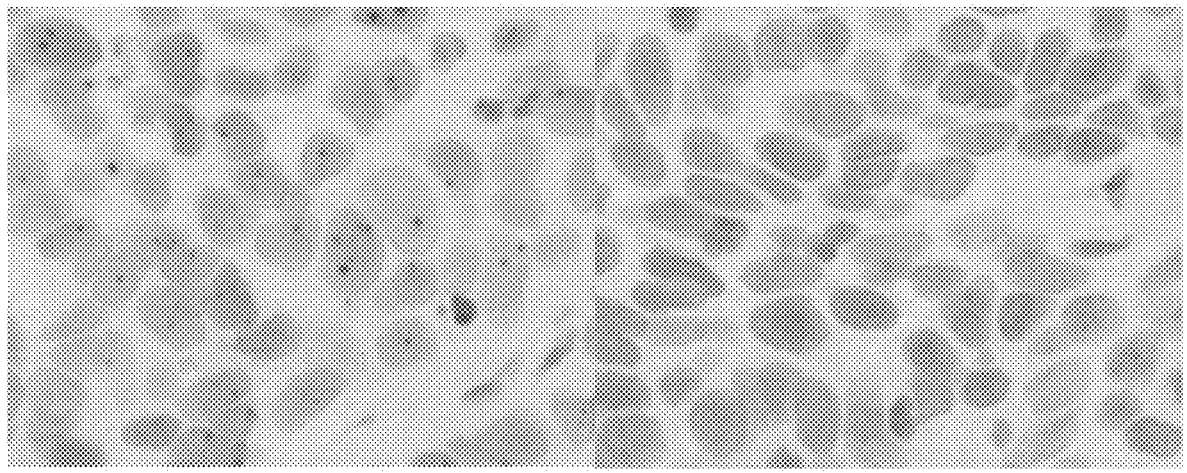
FIG. 29 is a photomicrograph illustrating direct detection of an ERG5' target in MCF-7 human breast adenocarcinoma cells using a DNA ISH assay with a Rhod-tyramide signaling conjugate.
FIG. 30 is a photomicrograph illustrating direct detection of an ERG3' target in MCF-7 human breast adenocarcinoma cells using a DNA ISH assay with a DABSYL-tyramide signaling conjugate.

FIG. 29 shows results obtained from using this embodiment to detect an ERG5' DNA ISH probe in MCF7 xenograft tumor cells.

Example 5

DNP or DIG labeled (0.25 ng/ml final concentration) ERG3' DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Dabsyl-tyramide (12.5 µM final concentration) was catalyzed by the addition of $H_2O_2$ (final percentage of 0.003%).

Additionally, an HRP conjugated anti-DNP or anti-DIG monoclonal antibody bound to the probe is used to catalyze amplifying conjugate deposition (6.25 µM final concentration) by the addition of $H_2O_2$. The covalently bound amplifying conjugate in the tissue served as binding sites for monoclonal anti-NP antibodies conjugated to HRP (2.5 ng/ml final concentration), and deposition of the signaling conjugate was catalyzed by the addition of the signaling conjugate (25 μM final concentration) and H$_2$O$_2$.

FIG. 30 illustrates results obtained from using this embodiment to detect an ERG3' DNA ISH probe in MCF7 xenograft tumor cells.

Example 6

DNP or DIG labeled (0.25 ng/ml final concentration) ERG3' and ERG5' DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Rhodamine-tyramide and Dabsyl-tyramide conjugates (12.5 μM final concentration) was catalyzed by the addition of H$_2$O$_2$ (final percentage of 0.003%).

Additionally, an HRP conjugated anti-DNP or anti-DIG monoclonal antibody bound to the probe is used to catalyze amplifying conjugate deposition (6.25 μM final concentration) by the addition of H$_2$O$_2$. The covalently bound amplifying conjugate in the tissue served as binding sites for monoclonal anti-BF and anti-NP antibodies conjugated to HRP (2.5 ng/ml final concentration), and deposition of the signaling conjugates was catalyzed by the addition of the signaling conjugate (25 μM final concentration) and H$_2$O$_2$.

Figure 31:
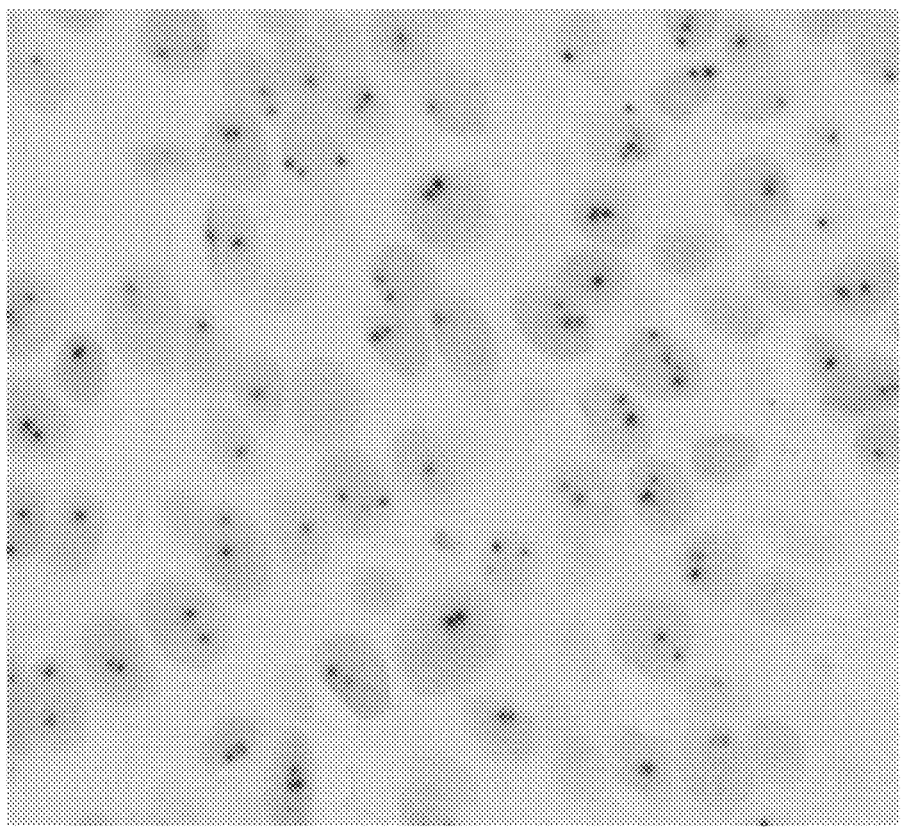
FIG. 31 is photomicrograph illustrating amplified detection of both ERG3' and ERG5' gene targets in MCF-7 human breast adenocarcinoma cells using a DNA ISH assay with a Rhod-tyramide signaling conjugate and a DABSYL-tyramide signaling conjugate.

FIG. 31 shows results obtained from using this embodiment to detect both ERG3' and ERG5' DNA ISH probes in MCF7 xenograft tumor cells. The red probe signals are generated from combined detection of the ERG5'-rhodamine signal, and the ERG3' Dabsyl signal.

Example 7

This embodiment concerns detecting an ERG gene rearrangement in prostate carcinoma cells using multiple signaling conjugates.

DNP or DIG labeled (0.25 ng/ml final concentration) ERG3' and ERG5' DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Rhodamine-tyramide and Dabsyl-tyramide conjugates (12.5 μM final concentration) was catalyzed by the addition of H$_2$O$_2$ (final percentage of 0.003%).

Additionally, an HRP conjugated anti-DNP or anti-DIG monoclonal antibody bound to the probe is used to catalyze amplifying conjugate deposition (6.25 μM final concentration) by the addition of H$_2$O$_2$. The covalently bound amplifying conjugate in the tissue served as binding sites for monoclonal anti-BF and anti-NP antibodies conjugated to HRP (2.5 ng/ml final concentration), and deposition of the signaling conjugates was catalyzed by the addition of the signaling conjugate (25 μM final concentration) and H$_2$O$_2$.

Figure 32:
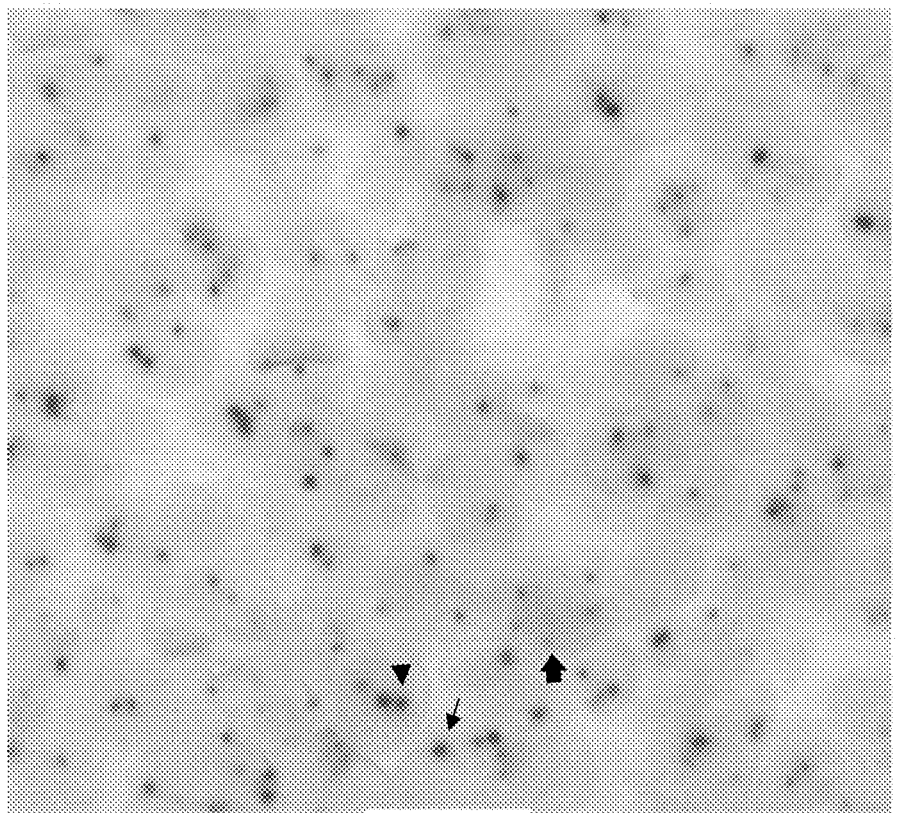
FIG. 32 is a photomicrograph obtained using a multiplexed DNA ISH assay showing rearrangement of the ERG gene in VCaP prostate cancer epithelial cells.

FIG. 32 illustrates results obtained from using this embodiment to detect both ERG3' and ERG5' DNA ISH probes in VCAP xenograft tumor cells. Individual and fused probe signals are indicated with arrows: the fused ERG5'-Rhodamine and ERG3'-Dabsyl signal (red signal at arrow) splitting into a separate purple ERG5'-Rhodamine signal (at arrow head) and a separate yellow ERG3'-Dabsyl signal (at thick, block arrow).

Example 8

This embodiment concerns detecting an ALK gene rearrangement in the CARPUS carcinoma cells using multiple signaling conjugates.

DNP or DIG labeled (0.25 ng/ml final concentration) Alk3' and Alk5' DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Rhodamine-tyramide and Dabsyl-tyramide conjugates (12.5 μM final concentration) was catalyzed by the addition of H$_2$O$_2$ (final percentage of 0.003%).

Additionally, an HRP conjugated anti-DNP or anti-DIG monoclonal antibody bound to the probe is used to catalyze amplifying conjugate deposition (6.25 μM final concentration) by the addition of H$_2$O$_2$. The covalently bound amplifying conjugate in the tissue served as binding sites for monoclonal anti-BF and anti-NP antibodies conjugated to HRP (2.5 ng/ml final concentration), and deposition of the signaling conjugates was catalyzed by the addition of the signaling conjugate (25 μNI final concentration) and H$_2$O$_2$.

Figure 33:
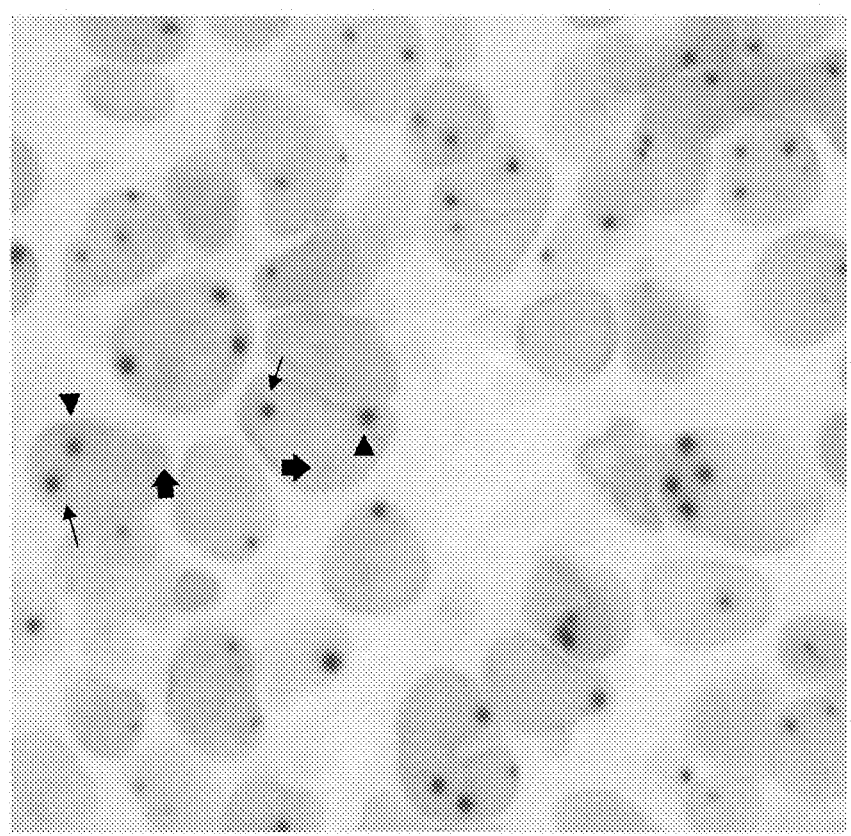
FIG. 33 is a photomicrograph obtained using a multiplexed DNA ISH assay illustrating rearrangement of the gene coding for anaplastic lymphoma kinase in a CARPUS cell pellet.

FIG. 33 illustrates results obtained from using this embodiment to detect both Alk3' and Alk5' DNA ISH probes in a CARPUS cell pellet. Probe signals in two cells with the ALK gene rearrangement have been indicated with arrows; the fused Alk5'-Rhodamine and Alk3'-Dabsyl signal (red signal at arrow) splitting into a separate purple Alk5'-Rhodamine signal (at arrow head) and a separate yellow Alk3'-Dabsyl signal (at thick, block arrow).

Example 9

This embodiment concerns detecting an ALK gene rearrangement in human lung cancer tissue using multiple signaling conjugates.

DNP or DIG labeled (0.25 ng/ml final concentration) Alk3' and Alk5' DNA ISH probes were hybridized for one to three hours in a formamide containing buffer, followed by stringency washing in 2×SSC. Probe detection was mediated by an anti-DNP or anti-DIG monoclonal antibody (2.5 ng/ml final concentration) that had been conjugated to horseradish peroxidase. Deposition of Rhodamine-tyramide and Dabsyl-tyramide conjugates (12.5 μM final concentration) was catalyzed by the addition of H$_2$O$_2$ (final percentage of 0.003%).

Additionally, an HRP conjugated anti-DNP or anti-DIG monoclonal antibody bound to the probe is used to catalyze amplifying conjugate deposition (6.25 μM final concentration) by the addition of H$_2$O$_2$. The covalently bound amplifying conjugate in the tissue served as binding sites for monoclonal anti-BF and anti-NP antibodies conjugated to HRP (2.5 ng/ml final concentration), and deposition of the signaling conjugates was catalyzed by the addition of the signaling conjugate (25 μM final concentration) and H$_2$O$_2$.

Figure 34:
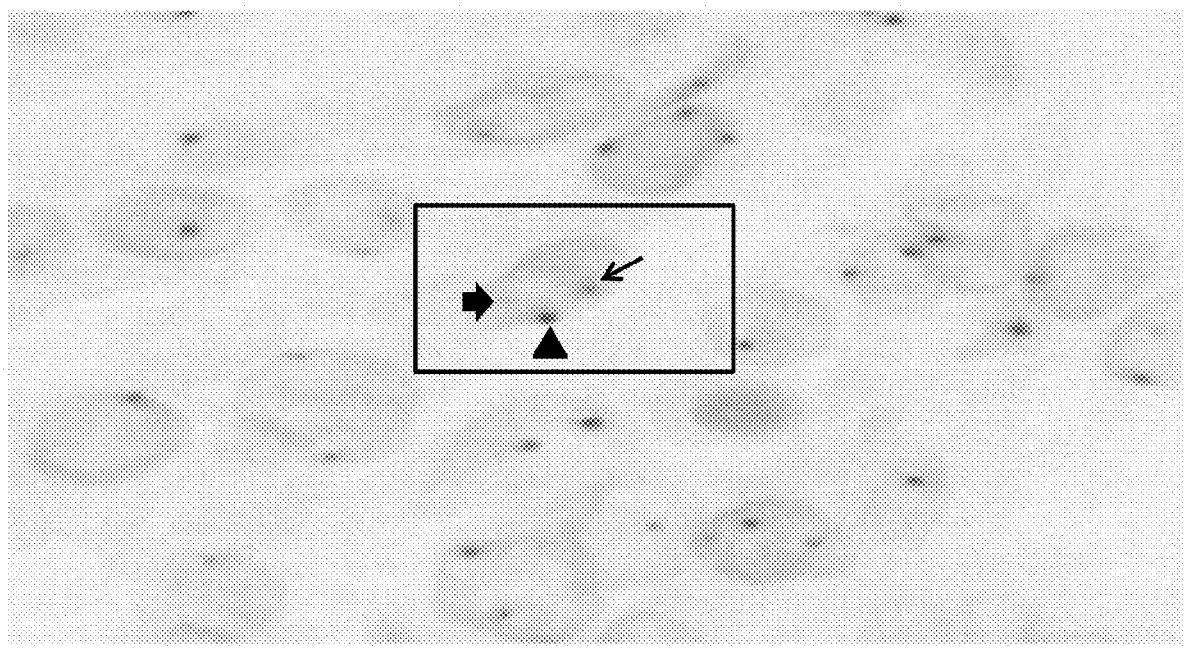
FIG. 34 is a photomicrograph obtained using a multiplexed DNA ISH assay illustrating rearrangement of the gene coding for anaplastic lymphoma kinase in a section of lung adenocarcinoma.

FIG. 34 illustrates results obtained from using this embodiment to detect both Alk3' and Alk5' DNA ISH probes in a 4 micron section of lung adenocarcinoma. The area within the box indicates a tumor cell where one copy of the ALK gene has rearranged, splitting the combined Alk5'-Rhodamine and Alk3'-Dabsyl signal (red signal at arrow) into a separate purple Alk5'-Rhodamine signal (at arrow head) and a separate yellow Alk3'-Dabsyl signal (at thick, block arrow).

Example 10

Figures 35A, 35B:
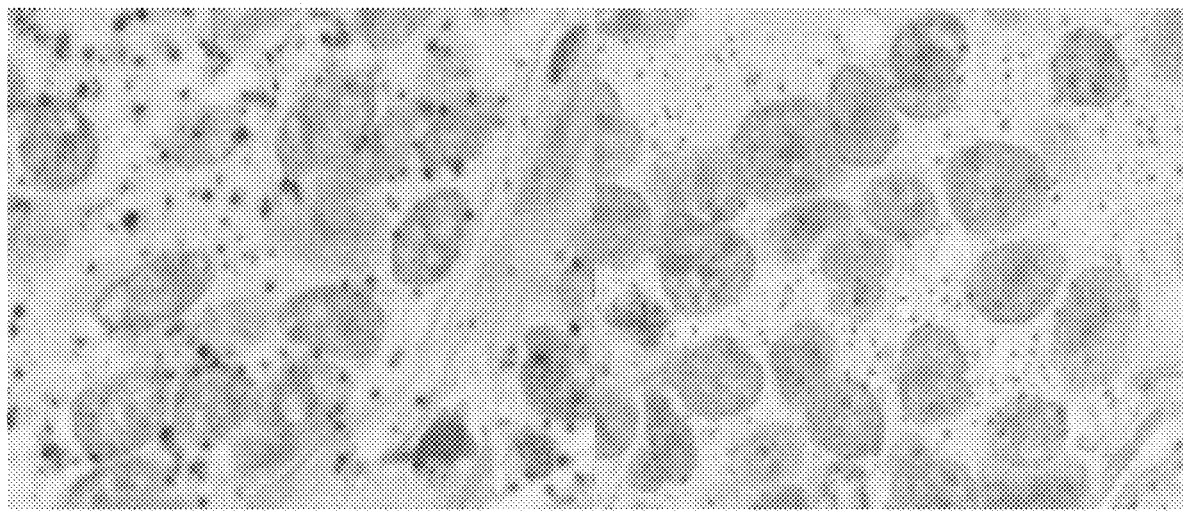
FIG. 35(A) shows detection of 18S RNA target using a Rhod-tyramide conjugate.
FIG. 35(B) shows detection of 18S RNA target using direct deposition of a DABSYL-tyramide conjugate.
Figures 35C, 36:
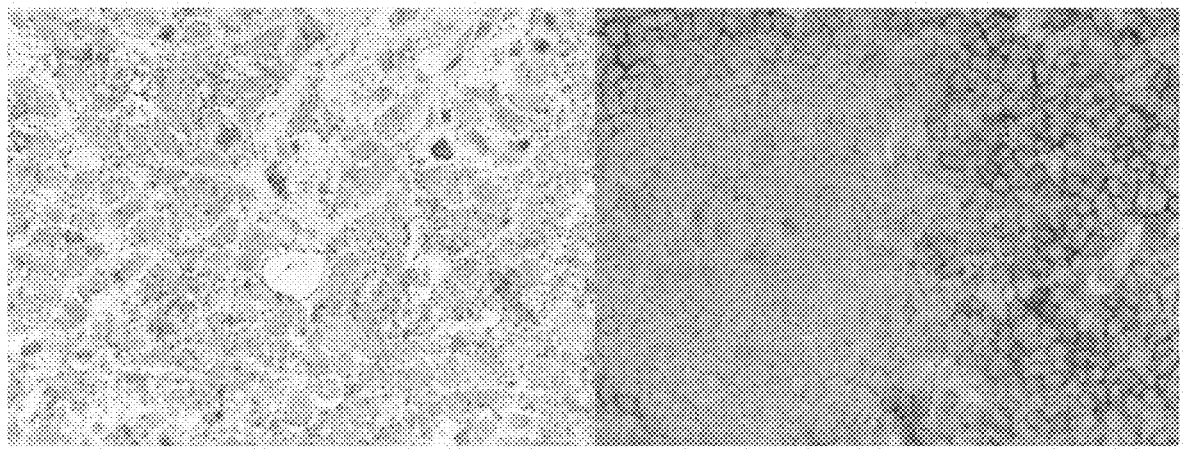
FIG. 35(C) illustrates a dual assay using the DABSYL-tyramide conjugate and the Rhod-tyramide conjugate.
FIG. 36 is a photomicrograph illustrating detecting, directly, HER2 and P53 proteins in Calu-3 cells using a multiplexed IHC assay. HER2 is detected by direct deposition of DABSYL-tyramide conjugate. P53 is detected by direct deposition of Rhodamine-tyramide conjugate.

This embodiment concerns detecting 18S RNA targets using two different colors of signaling conjugates simultaneously so as to create a third color. FIGS. 35(A-C) are photomicrographs illustrating direct detection of gene targets in Calu-3 cells using an mRNA ISH assay. FIG. 35(A) shows detection of 18S RNA target using a Rhodamine-tyramide conjugate. FIG. 35(B) shows detection of 18S RNA target using direct deposition of a DABSYL-tyramide conjugate. FIG. 35(C) illustrates a detection with both the DABSYL-tyramide conjugate and the Rhod-tyramide conjugate. The signal observed in FIG. 35(A) appears purple, the signal in FIG. 35(B) appears orange, and the signal in FIG. 35(C) appears red. FIG. 36 is a photomicrograph illustrating detecting, directly, HER2 and P53 proteins in Calu-3 cells using a multiplexed IHC assay. HER2 is detected by direct deposition of DABSYL-tyramide conjugate. P53 is detected by direct deposition of Rhodamine-tyramide conjugate. While the two signaling conjugates shown in FIGS. 35(A-B) can be used together to generate a third, combination, color, these two chromogens can also be used in a multiplexed format in which each color is assignable to a particular target.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of producing a stained biological sample comprising a first signaling complex on a solid support, comprising:
   (a) contacting a biological sample immobilized on a solid support with a first detection probe and a first enzyme conjugate comprising an enzyme, wherein the first detection probe specifically binds to a first target if said first target is present in said biological sample, and the first enzyme conjugate binds to the first detection probe, thereby forming a first binding complex comprising the first target, the first detection probe, and the first enzyme conjugate, wherein the first target comprises a polypeptide, nucleic acid, or a tyrosine-containing moiety, and the enzyme of the first enzyme conjugate is a peroxidase;
   (b) after step (a), contacting the first binding complex with a first amplifying conjugate comprising a phenolic moiety and a first hapten, such that, if said first target is present in said biological sample, the first amplifying conjugate contacts the enzyme of the first binding complex, and the enzyme of the first binding complex catalyzes conversion of the phenolic moiety of the first amplifying conjugate into a reactive species, thereby forming a modified form of the first amplifying conjugate, which comprises the reactive species and the first hapten, that covalently binds to at least one of:
      (1) a location on the first binding complex proximate to or directly on the first enzyme conjugate of the first binding complex;
      (2) a location on the first binding complex proximate to or directly on the first target of the first binding complex; and
      (3) a location on the biological sample proximate to the first target;
   whereby, if said first target is present in said biological sample, a first amplifying complex is formed, said first amplifying complex comprising the modified form of the first amplifying conjugate covalently bonded to the first binding complex and/or covalently bonded to the biological sample proximate to the first target;
   (c) after step (b), contacting the first amplifying complex with a first labeling conjugate comprising an antibody against said first hapten, which said antibody against said first hapten is conjugated to an enzyme, wherein the enzyme of said first labeling conjugate is a peroxidase, such that, if said first target is present in said biological sample, said first labeling conjugate becomes bound to said first amplifying complex, thereby forming a first deposited complex comprising said first labeling conjugate hound to said first amplifying complex;
   (d) after step (c), contacting the first deposited complex with a first signaling conjugate comprising a phenolic moiety and a first chromogenic moiety, such that, if said first target is present in said biological sample, the first signaling conjugate contacts the enzyme of said first deposited complex, and the enzyme of said first deposited complex catalyzes conversion of the phenolic moiety of the first signaling conjugate into a reactive species, thereby forming a modified form of the first signaling conjugate, which comprises the reactive species and the first chromogenic moiety, that covalently binds to at least one of:
      (1) a location on the first amplifying complex proximate to or directly on the modified form of the first amplifying conjugate of the first amplifying complex;
      (2) a location on the first labeling conjugate that is bound to said first amplifying complex; and
      (3) a location on the biological sample proximate to the first amplifying complex; whereby, if said first target is present in said biological sample, said first signaling complex is formed, said first signaling complex comprising the modified form of the first signaling conjugate covalently bonded to the first amplifying complex, covalently bonded to the first labeling conjugate, or covalently bonded to a location on the biological sample proximate to the first amplifying complex; and
   (e) after step (d), removing the first signaling conjugate unbound to the first signaling complex by washing the solid support, thereby, if said first target is present in said biological sample, producing the stained biological sample comprising the first signaling complex on the solid support;
   wherein, if said first target is present in said biological sample, the first chromogenic moiety of the first signaling complex of the stained biological sample produces a colored signal when the solid support is exposed to light that provides for the detection of said first target after step (e), wherein said light comprises one or more of visible light, infrared light, or near infrared light.

2. The method of claim 1, further comprising:
   (f) contacting said stained biological sample with a second detection probe and a second enzyme conjugate comprising an enzyme, wherein the second detection probe specifically binds to a second target if said second target is present in said stained biological sample, and the second enzyme conjugate binds to the second detection probe, thereby forming a second binding complex comprising the second target, the second detection probe, and the second enzyme conjugate, wherein the second target comprises a polypeptide, nucleic acid, or a tyrosine-containing moiety, and the enzyme of the second enzyme conjugate is a peroxidase;

(g) after step (f), contacting the second binding complex with a second amplifying conjugate comprising a phenolic moiety and a second hapten, such that, if said second target is present in said stained biological sample, the second amplifying conjugate contacts the enzyme of the second binding complex, and the enzyme of the second binding complex catalyzes conversion of the phenolic moiety of the second amplifying conjugate into a reactive species, thereby forming a modified form of the second amplifying conjugate, which comprises the reactive species and the second hapten, that covalently binds to at least one of:

(1) a location on the second binding complex proximate to or directly on the second enzyme conjugate of the second binding complex;

(2) a location on the second binding complex proximate to or directly on the second target of the second binding complex; and (3) a location on the stained biological sample proximate to the second target; Whereby, if said second target is present in said biological sample, a second amplifying complex is formed, said second amplifying complex comprising the modified form of the second amplifying conjugate covalently bonded to the second binding complex and/or covalently bonded to the stained biological sample proximate to the second target;

(h) after step (g), contacting the second amplifying complex with a second labeling conjugate comprising an antibody against said second hapten, which said antibody against said second hapten is conjugated to an enzyme, wherein the enzyme of said second labeling conjugate is a peroxidase, such that, if said second target is present in said stained biological sample, said second labeling conjugate becomes bound to said second amplifying complex, thereby forming a second deposited complex comprising said second labeling conjugate bound to said second amplifying complex;

(i) after step (h), contacting said second labeling conjugate of said second deposited complex with hydrogen peroxide and a second chromogen that is a chromogenic substrate of said enzyme of said second deposited complex, whereby, if said second target is present in said stained biological sample, said enzyme of said second deposited complex catalyzes conversion of the chromogenic substrate into a colored product deposited in a position proximate to said second labeling conjugate; and (j) after step (i), washing the solid support.

3. The method of claim 2, wherein said second chromogen is selected from 3, 3'diamino-benzidine (DAB), 3-amino-9-ethylcarbazole (AEC), and 4-chloro-1-naphthol (CN).

4. The method of claim 2, wherein said second chromogen is 3, 3' diaminobenzidine tetrahydrochloride (DAB).

5. The method of claim 4, wherein said first target comprises a KAPPA light chain mRNA or a LAMBDA light chain mRNA.

6. The method of claim 4, wherein said second target comprises a KAPPA light chain mRNA or a LAMBDA light chain mRNA.

7. The method of claim 4, wherein said first target comprises a KAPPA light chain mRNA and said second target comprises a LAMBDA light chain mRNA.

8. The method of claim 4, wherein said first target comprises a LAMBDA light chain mRNA and said second target comprises a KAPPA light chain mRNA.

9. The method of claim 2, wherein said first target comprises a KAPPA light chain mRNA or a LAMBDA light chain mRNA.

10. The method of claim 2, wherein said second target comprises a KAPPA light chain mRNA or a LAMBDA light chain mRNA.

11. The method of claim 2, wherein said first target comprises a KAPPA light chain mRNA and said second target comprises a LAMBDA light chain mRNA.

12. The method of claim 2, wherein said first target comprises a LAMBDA light chain mRNA and said second target comprises a KAPPA light chain mRNA.

13. The method of claim 1, further comprising:

(f) contacting said stained biological sample with a second detection probe and a second enzyme conjugate comprising an enzyme, wherein the second detection probe specifically binds to a second target if said second target is present in said stained biological sample, and the second enzyme conjugate binds to the second detection probe, thereby forming a second binding complex comprising the second target, the second detection probe, and the second enzyme conjugate, wherein the second target comprises a polypeptide, nucleic acid, or a tyrosine-containing moiety, and the enzyme of the second enzyme conjugate is a peroxidase;

(g) after step (f), contacting the second binding complex with a second amplifying conjugate comprising a phenolic moiety and a second hapten, such that, if said second target is present in said stained biological sample, the second amplifying conjugate contacts the enzyme of the second binding complex, and the enzyme of the second binding complex catalyzes conversion of the phenolic moiety of the second amplifying conjugate into a reactive species, thereby forming a modified form of the second amplifying conjugate, which comprises the reactive species and the second hapten, that covalently binds to at least one of:

(1) a location on the second binding complex proximate to or directly on the second enzyme conjugate of the second binding complex;

(2) a location on the second binding complex proximate to or directly on the second target of the second binding complex; and (3) a location on the stained biological sample proximate to the second target; whereby, if said second target is present in said stained biological sample, a second amplifying complex is formed, said second amplifying complex comprising the modified form of the second amplifying conjugate covalently bonded to the second binding complex and/or covalently bonded to the stained biological sample proximate to the second target;

(h) after step (g), contacting the second amplifying complex with a second labeling conjugate comprising an antibody against said second hapten, which said antibody against said second hapten is conjugated to an enzyme, wherein the enzyme of said second labeling conjugate is a peroxidase, such that, if said second target is present in said stained biological sample, said second labeling conjugate becomes bound to said second amplifying complex, thereby forming a second deposited complex comprising said second labeling conjugate bound to said second amplifying complex;

(i) after step (h), contacting the second deposited complex with a second signaling conjugate comprising a phenolic moiety and a second chromogenic moiety, such that, if said second target is present in said stained biological sample, the second signaling conjugate contacts the enzyme of said second deposited complex, and the enzyme of said second deposited complex catalyzes conversion of the phenolic moiety of the second signaling conjugate into a reactive species, thereby forming a modified form of the second signaling conjugate, which comprises the reactive species and the second chromogenic moiety, that covalently binds to at least one of:

(1) a location on the second amplifying complex proximate to or directly on the modified form of the second amplifying conjugate of the second amplifying complex;

(2) a location on the second labeling conjugate that is bound to said second amplifying complex; and (3) a location on the stained biological sample proximate to the second amplifying complex;

whereby, if said second target is present in said stained biological sample, a second signaling complex is formed, said second signaling complex comprising the modified form of the second signaling conjugate covalently bonded to the second amplifying complex, covalently bonded to the second labeling conjugate, or covalently bonded to a location on the stained biological sample proximate to the second amplifying complex; and (j) after step (i), removing the second signal conjugate unbound to the second signaling complex by washing the solid support, thereby, if said second target is present in said stained biological sample, producing a doubly stained biological sample comprising the second signaling complex on the solid support;

wherein, if said second target is present in said stained biological sample, the second chromogenic moiety of the second signaling complex of the doubly stained biological sample produces a colored signal when the solid support is exposed to light that provides for the detection of said second target after step (j), wherein said light comprises one or more of visible light, infrared light, or near infrared light.

14. The method of claim 13, further comprising, prior to step (f), inactivating the enzyme of said first enzyme conjugate.

15. The method of claim 13, wherein said first target comprises a KAPPA light chain mRNA or a LAMBDA light chain mRNA.

16. The method of claim 13, wherein said second target comprises a KAPPA light chain mRNA or a LAMBDA light chain mRNA.

17. The method of claim 13, wherein said first target comprises a KAPPA light chain mRNA and said second target comprises a LAMBDA light chain mRNA.

18. The method of claim 13, wherein said first target comprises a LAMBDA light chain mRNA and said second target comprises a KAPPA light chain mRNA.

19. The method of claim 1, wherein said first target comprises a KAPPA light chain mRNA or a LAMBDA light chain mRNA.

* * * * *